(12) United States Patent
Wang et al.

(10) Patent No.: US 9,611,498 B2
(45) Date of Patent: Apr. 4, 2017

(54) METHOD FOR PRODUCING STEVIOSIDE COMPOUNDS BY MICROORGANISM

(71) Applicant: Shanghai Institutes for Biological Sciences, Shanghai (CN)

(72) Inventors: Yong Wang, Shanghai (CN); Jianfeng Wang, Shanghai (CN); Zhiqiang Xiong, Shanghai (CN); Shiyuan Li, Shanghai (CN)

(73) Assignee: Shanghai Institutes For Biological Sciences, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 14/432,147

(22) PCT Filed: Sep. 29, 2013

(86) PCT No.: PCT/CN2013/084618
§ 371 (c)(1),
(2) Date: Mar. 27, 2015

(87) PCT Pub. No.: WO2014/048392
PCT Pub. Date: Apr. 3, 2014

(65) Prior Publication Data
US 2015/0252401 A1    Sep. 10, 2015

(30) Foreign Application Priority Data

Sep. 29, 2012 (CN) .......................... 2012 1 0378341

(51) Int. Cl.
*C12P 19/56* (2006.01)
*C12N 9/10* (2006.01)

(52) U.S. Cl.
CPC ............ *C12P 19/56* (2013.01); *C12N 9/1051* (2013.01); *Y02P 20/52* (2015.11)

(58) Field of Classification Search
None
See application file for complete search history.

(56) References Cited

U.S. PATENT DOCUMENTS

| 2011/0061124 A1* | 3/2011 | Nadzan .............. C07K 14/415 800/275 |
| 2012/0164678 A1* | 6/2012 | Stephanopoulos ...... A01H 5/00 435/29 |
| 2013/0035403 A1 | 2/2013 | Schaffer et al. |

FOREIGN PATENT DOCUMENTS

| WO | WO2011061032 | 5/2011 |
| WO | WO2011153378 A1 | 12/2011 |
| WO | WO2011154523 A1 | 12/2011 |

OTHER PUBLICATIONS

Sang, H., Mechanisms of Development 121:1179-1186, 2004.*
Okada et al., Plant Physiol. 122:1045-1056, 2000.*
Hunter, W., J. Biol. Chem. 282:21573-21577, 2007.*
Genbank Accession No. ABL74480.1, Dec. 19, 2006, [search date Dec. 25, 2013], searched from: NCBI [online], 3 pages.
International Search Report from corresponding PCT patent application No. PCT/CN2013/084618, dated Jan. 2, 2014, 4 pages.
Saerens, et al., "Cloning and functional characterization of the UDP-glucosyltransferase UgtB1 involved in teh sophorolipid production by Candida bombicola and creation of a glucolipid-producting yeast strain", wileyonlinelibrary.com, Yeast 2011, vol. 28, pp. 279-292.
Wanchao et al., "Advances on the Steviol Glycoside Biosynthesis and Its Key Enzymes," Biotechnology Bulletin, Feb. 2008, 8 pages.
Written Opinion from corresponding PCT patent application No. PCT/CN2013/084618, dated Jan. 2, 2014, 7 pages.
Guo, B. and Zhang P., "Molecular Cloning of Sweet Potato (*Ipomoea batatas* L.) glucosyltransferase gene and its function in Anthocyanin Biosynthesis", Nov. 2006, 1 page.

* cited by examiner

*Primary Examiner* — David J Steadman
(74) *Attorney, Agent, or Firm* — Lee & Hayes, PLLC

(57) ABSTRACT

The present invention provides a method for producing stevioside compounds by microorganism, comprising carrying out heterologous biosynthesis of stevioside compounds from geranyl geranyl pyrophosphate synthase (GGPPS), Copalyl pyrophosphate synthase (CDPS), Kaurene synthase (KS), dual-function kaurene synthase (CPS/KS), kaurene oxidase (KO), a cytochrome P450 redox protein (CPR), kaurenoic acid-13[alpha]-hydroxylase, UGT85C2 glycosyltransferase and UGTB1/IBGT glycosyltransferase (optionally comprising UGT74G1 glycosyltransferase and/or UGT76G1 glycosyltransferase).

14 Claims, 15 Drawing Sheets

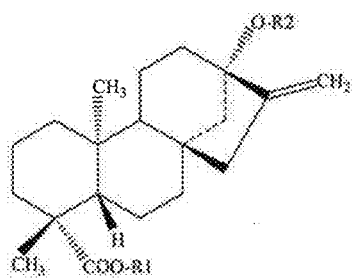
Fig. 1
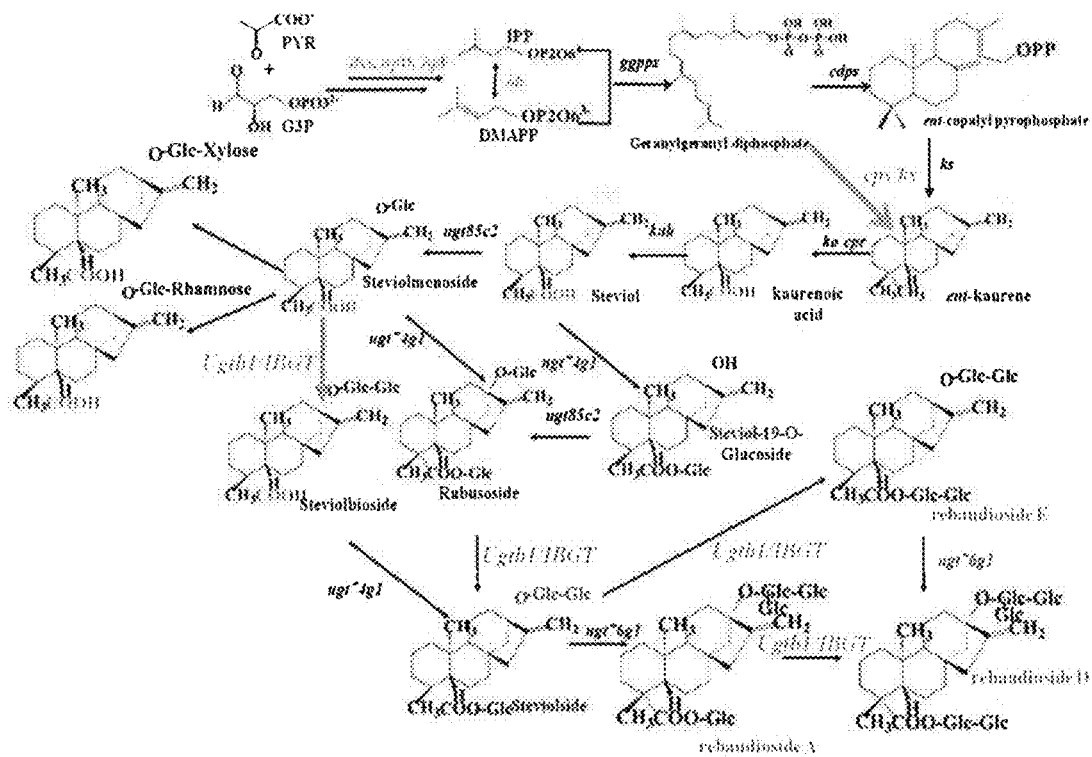
Fig. 2
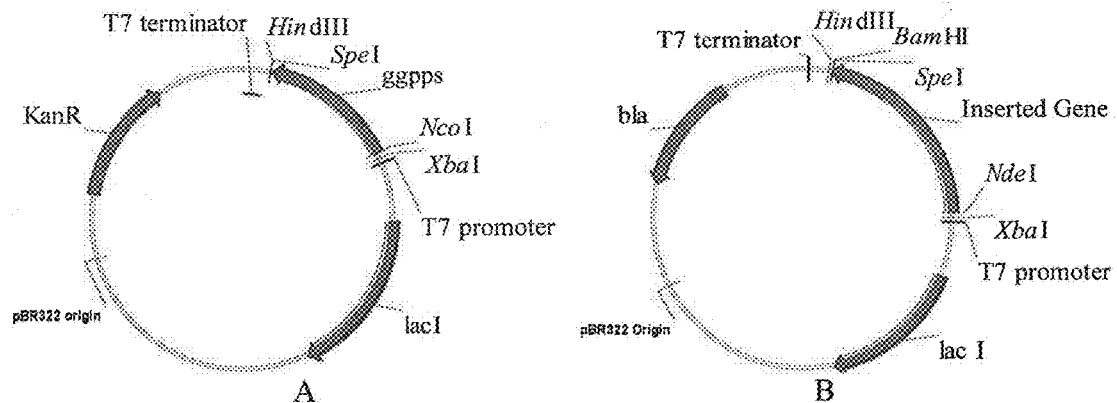

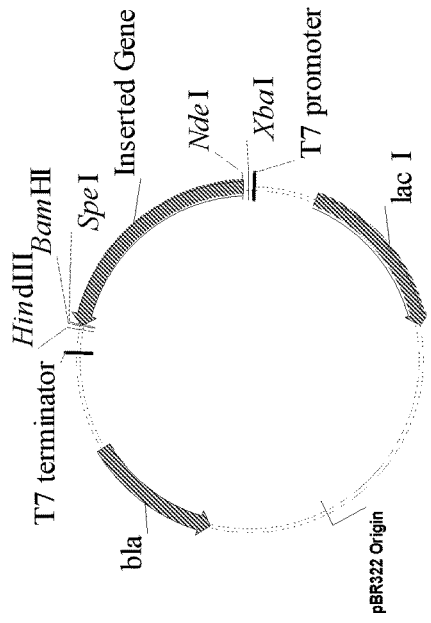
Fig. 3B
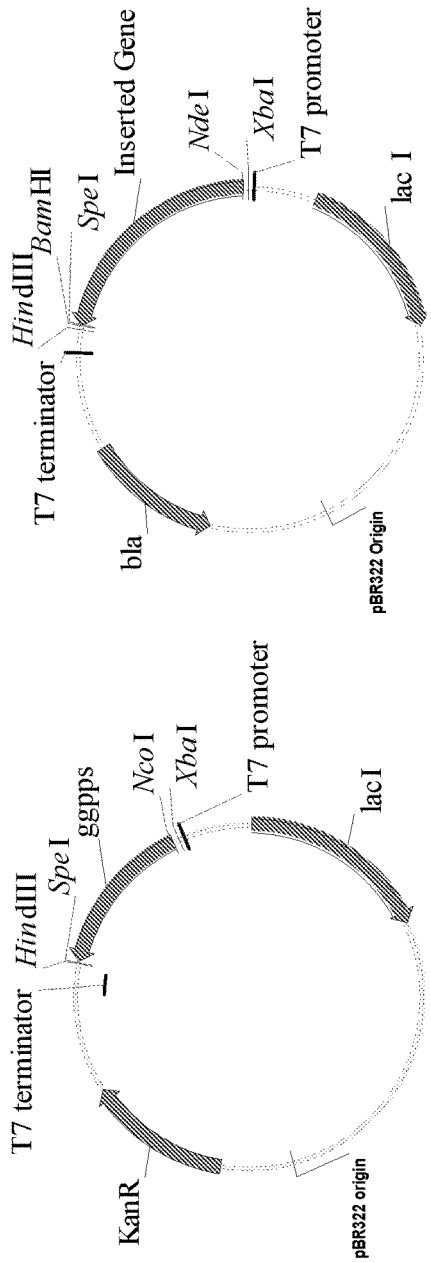
Fig. 3A
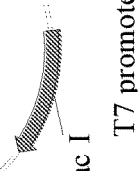
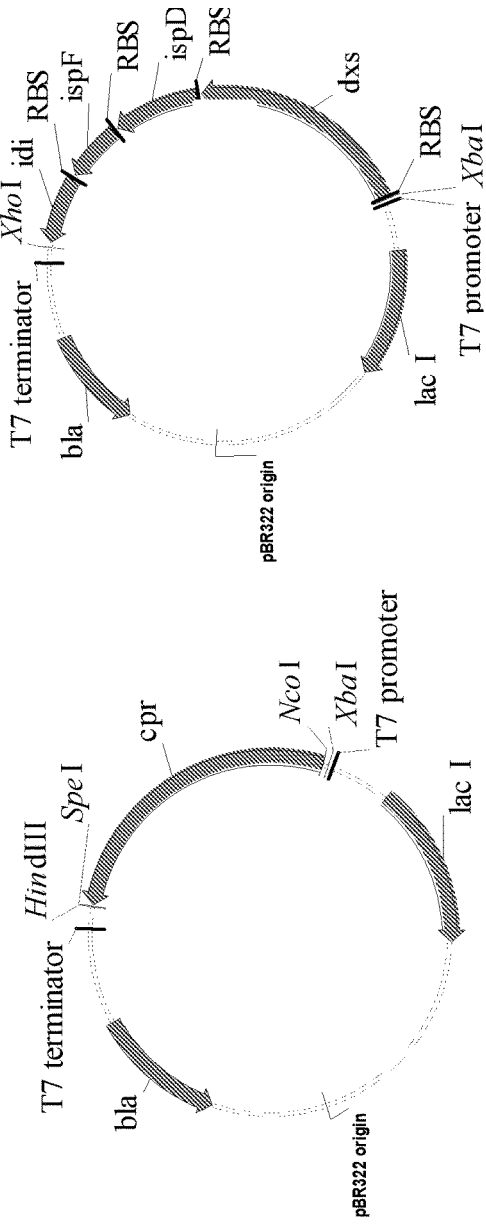
Fig. 3D
Fig. 3C

METHOD FOR PRODUCING STEVIOSIDE COMPOUNDS BY MICROORGANISM

SEQUENCE LISTING INFORMATION

A computer readable textfile, entitled "1 JV3897.txt (Sequence Listing.txt)" created on or about Aug. 26, 2016, with a file size of about 186 KB, contains the sequence listing for this application and is hereby incorporated by reference in its entirety.

This Application claims priority to and is a national phase of PCT/CN2013/084618, filed 29 Sep. 2013, entitled "METHOD FOR PRODUCING STEVIOSIDE COMPOUNDS BY MICROORGANISM," which claims priority to Chinese Patent Application No. 201210378341.3, filed 29 Sep. 2012, which are incorporated herein by reference.

TECHNICAL FIELD

The present invention belongs to the field of synthetic biology. Specifically, the present invention relates to a method for production of steviol glycosides by microorganisms.

BACKGROUND ART

Rebaudioside A (Reb A) is a new natural sweetener extracted from *Stevia rebaudiana* with intense sweetness, low calorific content and good stability, etc. Compared to the other main components of steviol glycosides, rebaudioside A (RebA) has the highest sweetness. The sweetness of rebaudioside A is at least 450 folds stronger than sucrose, but its calorific content is 300 folds less than sucrose. Besides, rebaudioside A has intense sweetness, white color, pure sweet taste and no peculiar smell. Therefore, it is the best nature alternative for sucrose and the chemically synthetic sweeteners, and it is called as "the third-generation sugar source" in the world.

FIG. 1 shows the structures of a portion of steviol glycosides extracted from *Stevia rebaudiana*, which has different side chain modifications due to their different R1 and R2 (see Table 1). *Stevia* sugar will have purer sweet taste if it contains more rebaudioside A and thus it will be accepted by more consumers. Therefore, the content of rebaudioside A in the product must be enhanced during production of *stevia* sugar.

TABLE 1

Steviol glycosides extracted from *Stevia rebaudiana*

| No. | Compound | R1 | R2 |
| --- | --- | --- | --- |
| 1 | Steviol | H | H |
| 2 | Steviolmonoside | H | β-Glc |
| 3 | Steviolbioside | H | β-Glc-β-Glc(2→1) |
| 4 | Rubusoside | β-Glc | β-Glc |
| 5 | Stevioside | β-Glc | β-Glc-β-Glc(2→1) |
| 6 | Rebaudioside A | β-Glc | β-Glc-β-Glc(2→1) β-Glc (3→1) |
| 7 | Rebaudioside B | H | β-Glc-β-Glc(2→1) β-Glc (3→1) |
| 8 | Rebaudioside C | β-Glc | β-Glc-α-Rha(2→1) β-Glc(3→1) |
| 9 | Rebaudioside D | β-Glc-β-Glc(2→1) | β-Glc-β-Glc(2→1) β-Glc (3→1) |
| 10 | Rebaudioside E | β-Glc-β-Glc(2→1) | β-Glc-β-Glc(2→1) |
| 11 | Rebaudioside F | β-Glc | β-Glc-α-Xly(2→1) β-Glc(3→1) |
| 12 | Dulcoside A | β-Glc | β-Glc-α-Rha(2→1) |

Currently, steviol glycosides have been widely used in food, beverage, medicine and cosmetic industries. The recent studies show that steviol glycosides can be used to prevent hypertension, diabetes and heart disease, etc. Therefore, there is a rapid need for steviol glycosides in the recent years.

Commercially available rebaudioside A currently is mainly extracted from the leaves of *Stevia rebaudiana*. The preparation process mainly includes the steps of drying and grinding the leaves of *Stevia rebaudiana*, extracting in a liquid phase, removing impurities, treating by resin, drying by spray and refining, etc. Generally, the leaves of *Stevia rebaudiana* may contain up to 4% to 20% of *stevia* sugar calculated by dried weight. However, there are many problems, including a great quantity of lands required for planting *Stevia rebaudiana*, different quantity of *Stevia rebaudiana* used for production of *stevia* sugar, low conversion efficiency of the raw material and low purity of the extracted product. Therefore, it is necessary to develop a production method for safely producing rebaudioside A in a large scale, with the raw material being readily obtained and the extraction method being simple.

As the development of techniques in synthetic biology during the last ten years, it is possible to produce various heterologous compounds by microorganisms. This synthesis has advantages of low cost, small production area and easy control of product quantity. However, synthesis of rebaudioside A by heterologous organisms is not reported to date. The key technical difficulty is that the glycosyltransferase used for converting steviolmonoside to steviolbioside was not known. Therefore, there is an urgent need to overcome the existing technical difficulty to achieve microbial synthesis of rebaudioside A.

CONTENTS OF INVENTION

The present invention aims to provide a method for producing steviol glycosides by microorganism.

In the first aspect of the present invention, an isolated polypeptide is provided, which is a glycosyltransferase obtained from the non-*Stevia rebaudiana* source and is used to catalyze transfer of an additional glucose to the C-2' of the O-glucosyl residue of steviol glycosides.

Preferably, the amino acid sequence of the polypeptide has a sequence identity no higher than 95%, preferably no higher than 80%, preferably, no higher than 70%, preferably no higher than 60%, preferably no higher than 50%, preferably no higher than 40%, preferably no higher than 30%, to the amino acid sequence of the enzyme having the same function and from *Stevia rebaudiana*.

In a preferred embodiment, the glycosyltransferase from the non-*Stevia rebaudiana* source is from *Starmerella bombicola* or *Ipomoea batatas*.

In another preferred embodiment, the glycosyltransferase from *Starmerella bombicola* has an amino acid sequence as set forth in SEQ ID NO: 41 (called as "UGTB1") or is a derivative protein having the same function and produced by substitution, deletion or addition of one or more amino acid residues in SEQ ID NO: 41.

In another preferred embodiment, the glycosyltransferase from *Ipomoea batatas* has an amino acid sequence as set forth in SEQ ID NO: 51 (called as "IBGT") or is a derivative protein having the same function and produced by substitution, deletion or addition of one or more amino acid residues in SEQ ID NO: 51.

In another aspect of the present invention, an isolated nucleotide sequence is provided, which encodes the glycosyltransferase from the non-*Stevia rebaudiana* source, and is used to catalyze transfer of an additional glycosyl unit to the C-2' of the O-glucosyl residue of steviol glycosides.

In a preferred embodiment, the nucleotide sequence has (1) a sequence shown in SEQ ID NO: 42, or a sequence having 70% or more, preferably 80% or more, preferably 90% or more, more preferably 95% or more, homology to SEQ ID NO: 42; (2) a sequence shown in SEQ ID NO: 52, or a sequence having 70% or more, preferably 80% or more, preferably 90% or more, more preferably 95% or more, homology to SEQ ID NO: 52.

In another preferred embodiment, the nucleotide sequence is (1) the sequence as set forth in SEQ ID NO: 42 or (2) the sequence as set forth in SEQ ID NO: 52.

In another aspect of the invention, use of the glycosyltransferase from the non-*Stevia rebaudiana* source, which could catalyze the transfer of an additional glucosyl unit to the C-2' of the O-glucosyl residue of steviol glycosides, for recombination expression in a host cell to prepare a steviol glycoside is provided.

In a preferred embodiment, the catalytic substrate of the glycosyltransferase includes, but is not limited to, steviol-13-O-glucoside (also called as steviolmonoside), rubusoside, Stevioside, and rebaudioside A. Preferably, steviolmonoside is catalyzed to produce steviolbioside.

In another aspect of the present invention, a method for synthesizing steviol glycosides is provided, which includes the step of recombinantly expressing the glycosyltransferase from the non-*Stevia rebaudiana* source in a host cell, which is capable of catalyzing transfer of an additional glucose to the C-2' of the O-glucose residue of the steviol glycosides.

In a preferred embodiment, the host cell further comprises one or more of:

(a) Geranylgeranyl diphosphate synthase;
(b) An enzyme selected from (I) ent-copalyl diphosphate synthase and ent-kaurene synthase and (II) bifunctional ent-kaurene synthase;
(c) Ent-kaurene oxidase;
(d) Cytochrome P450 redox protein;
(e) Kaurenoic acid-13α-hydroxylase;
(f) UGT85C2 glycosyltransferase;
(h) UGT74G1 glycosyltransferase; and
(i) UGT76G1 glycosyltransferase.

In another preferred embodiment, the host cell further contains gene expression cassette(s) of the following enzymes: 1-deoxy-D-xylulose-5-phosphate synthase, 2-C-methyl-D-erythritol 4-phosphate cytidylyltransferase, 2-C-methyl-D-erythritol 2,4-cyclodiphosphate synthase and isopentenyl-diphosphate delta-isomerase.

In another preferred embodiment, the host cell is a cell from prokaryotic microorganisms and eukaryotic microorganisms.

In another preferred embodiment, the prokaryotic microorganism is *Escherichia coli, Bacillus subtilis, Acetobacteria, Corynebacterium* or *Brevibacterium*. Preferably, the *E. coli* is selected from the group consisting of BL21, BLR, DH10B, HMS, C43, JM109, DH5a or Noveblue. The eukaryotic microorganism is yeast, mold, or basidiomycete. Yeast may be *Pichia pastoris, Saccharomyces cerevisiae*, or *Kluyveromyces lactis*. Preferably, *Pichia pastoris* may be selected from GS115, MC100-3, SMD1163, SMD1165, SMD1168 or KM71. Preferably, *Saccharomyces cerevisiae* may be selected from W303, CEN.PK2, S288c, FY834 or S1949. Preferably, *Kluyveromyces lactis* may be GG799.

In another aspect of the present invention, a method for synthesizing a steviol glycoside, comprising recombinantly, preferably heterologously, expressing in a cell the following enzymes:

(a) Geranylgeranyl diphosphate synthase (GGPPS);
(b) An enzyme selected from (I) or (II) as follows: (I) ent-copalyl diphosphate synthase (CDPS) and ent-kaurene synthase (KS) and (II) bifunctional ent-kaurene synthase (CPS/KS);
(c) Ent-kaurene oxidase (KO);
(d) Cytochrome P450 redox protein (CPR);
(e) Kaurenoic acid-13α-hydroxylase;
(f) UGT85C2 glycosyltransferase; and
(g) UGTB1/IBGT glycosyltransferase;

and culturing the cell to produce the steviol glycoside.

In a preferred embodiment, the method further contains recombinantly expressing:

(h) UGT74G1 glycosyltransferase; and/or
(i) UGT76G1 glycosyltransferase.

In another preferred embodiment, the geranylgeranyl diphosphate synthase, ent-copalyl diphosphate synthase, ent-kaurene synthase, ent-kaurene oxidase, kaurenoic acid-13α-hydroxylase, UGT85C2 glycosyltransferase and UGTB1/IBGT glycosyltransferase are recombinantly expressed to synthesize steviolbioside.

In another preferred embodiment, the geranylgeranyl diphosphate synthase, ent-copalyl diphosphate synthase, ent-kaurene synthase, ent-kaurene oxidase, kaurenoic acid-13α-hydroxylase, UGT85C2 glycosyltransferase, UGTB1/IBGT glycosyltransferase and UGT74G1 glycosyltransferase are recombinantly expressed to synthesize stevioside.

In another preferred embodiment, the geranylgeranyl diphosphate synthase, ent-copalyl diphosphate synthase, ent-kaurene synthase, ent-kaurene oxidase, kaurenoic acid-13α-hydroxylase, UGT85C2 glycosyltransferase, UGTB1/IBGT glycosyltransferase, UGT74G1 glycosyltransferase and UGT76G1 glycosyltransferase are recombinantly expressed to synthesize rebaudioside A.

In another preferred embodiment, in item (b), (II) bifunctional ent-kaurene synthase is used.

In another preferred embodiment, the geranylgeranyl diphosphate synthase used in the method can be obtained from *Taxus canadensis* or *Stevia rebaudiana*, preferably from *Taxus Canadensis*;

The ent-copalyl diphosphate synthase can be obtained from *Stevia rebaudiana* or *Bradyrhizobium japonicum*, preferably from *Stevia rebaudiana*;

The ent-kaurene synthase can be obtained from *Stevia rebaudiana* or *Bradyrhizobium japonicum*, preferably from *Stevia rebaudiana*;

The bifunctional ent-kaurene synthase can be obtained from *Physcomitrella patens* or *Gibberella fujikuroi*, preferably from *Physcomitrella patens*;

The ent-kaurene oxidase can be obtained from *Stevia rebaudiana, Gibberella fujikuroi, Arabidopsis thaliana*, or *Bradyrhizobium japonicum*, preferably from *Stevia rebaudiana*.

The kaurenoic acid-13α-hydroxylase can be obtained from *Stevia rebaudiana* or *Arabidopsis thaliana*, preferably from *Stevia rebaudiana*;

The UGT85C2 glycosyltransferase, UGT74G1 glycosyltransferase and UGT76G1 glycosyltransferase can be obtained from *Stevia rebaudiana*;

The UGTB1 glycosyltransferase can be obtained from *Starmerella bombicola*. The IBGT glycosyltransferase can be obtained from *Ipomoea batatas*. The cytochrome P450 redox protein can be obtained from *Artemisia annua, Phaeosphaeria* sp. L487, *Gibberella fujikuroi, Stevia rebaudiana*, or *Arabidopsis thaliana*, preferably from *Phaeosphaeria* sp.

In another preferred embodiment, in item (b), (II) bifunctional ent-kaurene synthase is used; the geranylgeranyl diphosphate synthase is obtained from *Taxus canadensis*, the bifunctional ent-kaurene synthase is obtained from *Physcomitrella patens*; the ent-kaurene oxidase, kaurenoic acid-13α-hydroxylase, UGT85C2 glycosyltransferase, UGT74G1 glycosyltransferase and UGT76G1 glycosyltransferase are from *Stevia rebaudiana*; the UGTB1 glycosyltransferase is from *Starmerella bombicola*; the cytochrome P450 redox protein is from *Phaeosphaeria*; and the IGBT glycosyltransferase is from *Ipomoea batatas*.

In another preferred embodiment, the geranylgeranyl diphosphate synthase from *Taxus canadensis* has its transit-peptide sequence removed from its N terminus in relative to the wild type sequence. Preferably, the 98 amino acid residues at the N terminus are truncated;

the cytochrome P450 redox protein from *Artemisia annua* has its transmembrane domain removed from its N terminus in relative to the wild type sequence. Preferably, the 66 amino acid residues at the N terminus are truncated.

In another preferred embodiment, the geranylgeranyl diphosphate synthase has an amino acid sequence as shown in SEQ ID NO: 1 or 45, or is a derivative protein having the same function and produced by substitution, deletion or addition of one or more (such as 1-30, preferably 1-20, more preferably 1-10, and more preferably 1-5) amino acid residues on SEQ ID NO: 1 or 45;

the ent-copalyl diphosphate synthase has an amino acid sequence as shown in SEQ ID NO: 3 or 25, or is a derivative protein having the same function and produced by substitution, deletion or addition of one or more (such as 1-30, preferably 1-20, more preferably 1-10, and more preferably 1-5) amino acid residues on SEQ ID NO: 3 or 25;

the ent-kaurene synthase has an amino acid sequence as shown in SEQ ID NO: 5 or 27, or is a derivative protein having the same function and produced by substitution, deletion or addition of one or more (such as 1-30, preferably 1-20, more preferably 1-10, and more preferably 1-5) amino acid residues on SEQ ID NO: 5 or 27;

the bifunctional ent-kaurene synthase has an amino acid sequence as shown in SEQ ID NO: 21 or 23, or is a derivative protein having the same function and produced by substitution, deletion or addition of one or more (such as 1-30, preferably 1-20, more preferably 1-10, and more preferably 1-5) amino acid residues on SEQ ID NO: 21 or 23;

the ent-kaurene oxidase has an amino acid sequence as shown in SEQ ID NO: 7, 31, 37 or 29, or is a derivative protein having the same function and produced by substitution, deletion or addition of one or more (such as 1-30, preferably 1-20, more preferably 1-10, and more preferably 1-5) amino acid residues on SEQ ID NO: 7, 31, 37 or 29;

the kaurenoic acid-13α-hydroxylase has an amino acid sequence as shown in SEQ ID NO: 9, 43, 47 or 49, or is a derivative protein having the same function and produced by substitution, deletion or addition of one or more (such as 1-30, preferably 1-20, more preferably 1-10, and more preferably 1-5) amino acid residues on SEQ ID NO: 9, 43, 47 or 49;

the UGT85C2 glycosyltransferase has an amino acid sequence as shown in SEQ ID NO: 11, or is a derivative protein having the same function and produced by substitution, deletion or addition of one or more (such as 1-30, preferably 1-20, more preferably 1-10, and more preferably 1-5) amino acid residues on SEQ ID NO: 11;

the UGT74G1 glycosyltransferase has an amino acid sequence as shown in SEQ ID NO: 13, or is a derivative protein having the same function and produced by substitution, deletion or addition of one or more (such as 1-30, preferably 1-20, more preferably 1-10, and more preferably 1-5) amino acid residues on SEQ ID NO: 13;

the UGT76G1 glycosyltransferase has an amino acid sequence as shown in SEQ ID NO: 15, or is a derivative protein having the same function and produced by substitution, deletion or addition of one or more (such as 1-30, preferably 1-20, more preferably 1-10, and more preferably 1-5) amino acid residues on SEQ ID NO: 15;

the UGTB1 glycosyltransferase has an amino acid sequence as shown in SEQ ID NO: 41, or is a derivative protein having the same function and produced by substitution, deletion or addition of one or more (such as 1-30, preferably 1-20, more preferably 1-10, and more preferably 1-5) amino acid residues on SEQ ID NO: 41;

the IBGT glycosyltransferase has an amino acid sequence as shown in SEQ ID NO: 51, or is a derivative protein having the same function and produced by substitution, deletion or addition of one or more (such as 1-30, preferably 1-20, more preferably 1-10, and more preferably 1-5) amino acid residues on SEQ ID NO: 51; or the cytochrome P450 redox protein has an amino acid sequence as shown in SEQ ID NO: 17, 19, 33, 35 or 39, or is a derivative protein having the same function and produced by substitution, deletion or addition of one or more (such as 1-30, preferably 1-20, more preferably 1-10, and more preferably 1-5) amino acid residues on SEQ ID NO: 17, 19, 33, 35 or 39.

In another preferred embodiment, the coding gene of the geranylgeranyl diphosphate synthase has a nucleotide sequence as shown in SEQ ID NO: 2 or 46, or a nucleotide sequence encoding a protein having the same function and having 70% or more, 80% or more, more preferably 90% or more, more preferably 93% or more, more preferably 95% or more, more preferably 97% or more, identity to SEQ ID NO: 2 or 46;

the coding gene of the ent-copalyl diphosphate synthase has a nucleotide sequence as shown in SEQ ID NO: 4 or 26, or a nucleotide sequence encoding a protein having the same function and having 70% or more, 80% or more, more preferably 90% or more, more preferably 93% or more, more preferably 95% or more, more preferably 97% or more, identity to SEQ ID NO: 4 or 26;

the coding gene of the ent-kaurene synthase has a nucleotide sequence as shown in SEQ ID NO: 6 or 28, or a nucleotide sequence encoding a protein having the same function and having 70% or more, 80% or more, more preferably 90% or more, more preferably 93% or more, more preferably 95% or more, more preferably 97% or more, identity to SEQ ID NO: 6 or 28;

the coding gene of the bifunctional ent-kaurene synthase has a nucleotide sequence as shown in SEQ ID NO: 22 or 24, or a nucleotide sequence encoding a protein having the same function and having 70% or more, 80% or more, more preferably 90% or more, more preferably 93% or more, more preferably 95% or more, more preferably 97% or more, identity to SEQ ID NO: 22 or 24;

the coding gene of the ent-kaurene oxidase has a nucleotide sequence as shown in SEQ ID NO: 8, 32, 38 or 30, or a nucleotide sequence encoding a protein having the same function and having 70% or more, 80% or more, more preferably 90% or more, more preferably 93% or more, more preferably 95% or more, more preferably 97% or more, identity to SEQ ID NO: 8, 32, 38 or 30;

the coding gene of the kaurenoic acid-13α-hydroxylase has a nucleotide sequence as shown in SEQ ID NO: 10, 44, 48 or 50, or a nucleotide sequence encoding a protein having the same function and having 70% or more, 80% or more, more preferably 90% or more, more preferably 93% or more, more preferably 95% or more, more preferably 97% or more, identity to SEQ ID NO: 10, 44, 48 or 50;

the coding gene of the UGT85C2 glycosyltransferase has a nucleotide sequence as shown in SEQ ID NO: 12, or a nucleotide sequence encoding a protein having the same function and having 70% or more, 80% or more, more preferably 90% or more, more preferably 93% or more, more preferably 95% or more, more preferably 97% or more, identity to SEQ ID NO: 12;

the coding gene of the UGT74G1 glycosyltransferase has a nucleotide sequence as shown in SEQ ID NO: 14, or a nucleotide sequence encoding a protein having the same function and having 70% or more, 80% or more, more preferably 90% or more, more preferably 93% or more, more preferably 95% or more, more preferably 97% or more, identity to SEQ ID NO: 14;

the coding gene of the UGT76G1 glycosyltransferase has a nucleotide sequence as shown in SEQ ID NO: 16, or a nucleotide sequence encoding a protein having the same function and having 70% or more, 80% or more, more preferably 90% or more, more preferably 93% or more, more preferably 95% or more, more preferably 97% or more, identity to SEQ ID NO: 16;

the coding gene of the UGTB1 glycosyltransferase has a nucleotide sequence as shown in SEQ ID NO: 42, or a nucleotide sequence encoding a protein having the same function and having 70% or more, 80% or more, more preferably 90% or more, more preferably 93% or more, more preferably 95% or more, more preferably 97% or more, identity to SEQ ID NO: 42;

the coding gene of the IBGT glycosyltransferase has a nucleotide sequence as shown in SEQ ID NO: 52, or a nucleotide sequence encoding a protein having the same function and having 70% or more, 80% or more, more preferably 90% or more, more preferably 93% or more, more preferably 95% or more, more preferably 97% or more, identity to SEQ ID NO: 52; or the coding gene of the cytochrome P450 redox protein has a nucleotide sequence as shown in SEQ ID NO: 18, 20, 34, 36 or 40, or a nucleotide sequence encoding a protein having the same function and having 70% or more, 80% or more, more preferably 90% or more, more preferably 93% or more, more preferably 95% or more, more preferably 97% or more, identity to SEQ ID NO: 18, 20, 34, 36 or 40.

In another preferred embodiment, the cell is selected from but is not limited to the cell from prokaryotic microorganisms and eukaryotic microorganisms.

In another preferred embodiment, the prokaryotic microorganism is *E. coli, Bacillus subtilis, Acetobacteria, Corynebacterium* and *Brevibacterium*. Preferably, the *E. coli* is selected from the group consisting of BL21, BLR, DH10B, HMS, C43, JM109, DH5α or Noveblue.

In another preferred embodiment, the eukaryotic microorganism is selected from, but is not limited to, yeast, mold, or basidiomycete. Yeast may be, but is not limited to, *Pichia pastoris, Saccharomyces cerevisiae,* or *Kluyveromyces lactis*. Preferably, *Pichia pastoris* may be selected from GS115, MC100-3, SMD1163, SMD1165, SMD1168 or KM71. Preferably, *Saccharomyces cerevisiae* may be selected from W303, CEN.PK2, S288c, FY834 or S1949. Preferably, *Kluyveromyces lactis* may be GG799.

In another preferred embodiment, the cell is a gram-negative strain and it uses pET, pBAD and pQE expression vectors, such as pET28a and pET21c, to recombinantly express each enzyme. Alternatively, when the cell is a yeast cell, pPIC expression vector, such as pPIC3.5, or pSY expression vector, such as pSY01, is used to recombinantly express each enzyme.

In another preferred embodiment, the method comprises the step of inserting the coding genes of (a)-(g) and optionally (h)-(i) into the recombinant expression vectors to construct gene expression cassette(s) for recombinantly expressing the enzymes.

In another aspect of the present invention, an expression construct, such as an expression vector, for synthesizing a steviol glycoside is provided, which comprises the gene expression cassette(s) of the following enzymes:
 (a) Geranylgeranyl diphosphate synthase (GGPPS);
 (b) An enzyme selected from (I) ent-copalyl diphosphate synthase (CDPS) and ent-kaurene synthase (KS) and (II) bifunctional ent-kaurene synthase (CPS/KS);
 (c) Ent-kaurene oxidase (KO);
 (d) Cytochrome P450 redox protein (CPR);
 (e) Kaurenoic acid-13α-hydroxylase;
 (f) UGT85C2 glycosyltransferase; and
 (g) UGTB1/IBGT glycosyltransferase.

In another preferred embodiment, the expression construct for synthesizing a steviol glycoside may further comprise the gene expression cassette(s) of the following enzymes:
 (h) UGT74G1 glycosyltransferase; and/or
 (i) UGT76G1 glycosyltransferase.

In another aspect of the present invention, an expression construct for strengthening the precursor pathway of a steviol glycoside is provided, which comprises the gene expression cassette(s) of the following enzymes: 1-deoxy-D-xylulose-5-phosphate synthase (DXS), 2-C-methyl-D-erythritol 4-phosphate cytidylyltransferase (CMS), 2-C-methyl-D-erythritol 2,4-cyclodiphosphate synthase (MCS) and isopentenyl-diphosphate delta-isomerase (IDI).

In another aspect of the present invention, a host cell for synthesizing a steviol glycoside is provided, which comprises the expression constructs for synthesizing the steviol glycoside.

In another preferred embodiment, the host cell for synthesizing a steviol glycoside is a non-generative material or a non-propagative material.

In another preferred embodiment, the cell used for synthesizing a steviol glycoside is selected from, but is not limited to, a cell from prokaryotic microorganisms and eukaryotic microorganisms.

In another preferred embodiment, the host cell for synthesizing a steviol glycoside may further comprise the expression construct for strengthening the precursor pathway of a steviol glycoside.

In another aspect of the present invention, a method for preparing ent-kaurene is provided, which comprises recombinantly, preferably heterologously, expressing in a cell from prokaryotic microorganisms and eukaryotic microorganisms (a) geranylgeranyl diphosphate synthase (GGPPS) and (b) bifunctional ent-kaurene synthase (CPS/KS).

In another preferred embodiment, the geranylgeranyl diphosphate synthase can be obtained from *Taxus canadensis* or *Stevia rebaudiana*, preferably from *Taxus Canadensis*; or the bifunctional ent-kaurene synthase can be obtained from *Physcomitrella patens* or *Gibberella fujikuroi*.

In another aspect of the present invention, an expression construct for preparing ent-kaurene is provided, which comprises the gene expression cassette(s) of the following enzymes: (a) Geranylgeranyl diphosphate synthase; and (b) bifunctional ent-kaurene synthase.

In another aspect of the present invention, a host cell for preparing ent-kaurene is provided, which comprises the expression construct for preparing ent-kaurene, and/or the expression construct for strengthening the precursor pathway of a steviol glycoside.

In another preferred embodiment, the host cell for preparing ent-kaurene is a gram negative DE3 lysogenic strain or a yeast cell.

In another aspect of the present invention, use of UGTB1/IBGT glycosyltransferase is provided for converting steviolmonoside into steviolbioside, preferably adding a glycosyl group at the C-2' of the C13 glucose of the steviolmonoside.

In another aspect of the present invention, use of bifunctional ent-kaurene synthase is provided for converting geranylgeranyl diphosphate to ent-kaurene.

In another aspect of the present invention, a combination of enzymes for preparing a steviol glycoside is provided, which comprises:
(a) Geranylgeranyl diphosphate synthase (GGPPS);
(b) An enzyme selected from (I) ent-copalyl diphosphate synthase (CDPS) and ent-kaurene synthase (KS) and (II) bifunctional ent-kaurene synthase (CPS/KS);
(c) Ent-kaurene oxidase (KO);
(d) Cytochrome P450 redox protein (CPR);
(e) Kaurenoic acid-13α-hydroxylase;
(f) UGT85C2 glycosyltransferase; and
(g) UGTB1/IBGT glycosyltransferase.

In another preferred embodiment, the combination of enzymes may further comprise:
(h) UGT74G1 glycosyltransferase;
(i) UGT76G1 glycosyltransferase.

In another aspect of the present invention, a kit for preparing a steviol glycoside is provided, which comprises the expression construct(s) for synthesizing the steviol glycoside. Preferably, the kit may further comprise the expression construct for strengthening the precursor pathway of the steviol glycoside. Alternatively, the kit may comprise the host cell for synthesizing the steviol glycoside.

In another aspect of the present invention, a combination for preparing ent-kaurene, such as a kit comprising enzymes, is provided, which comprises (a) geranylgeranyl diphosphate synthase (GGPPS) and (b) bifunctional ent-kaurene synthase (CPS/KS).

In another preferred embodiment, the combination for preparing ent-kaurene may further comprise 1-deoxy-D-xylulose-5-phosphate synthase, 2-C-methyl-D-erythritol 4-phosphate cytidylyltransferase, 2-C-methyl-D-erythritol 2,4-cyclodiphosphate synthase and isopentenyl-diphosphate delta-isomerase.

In another aspect of the present invention, a kit for preparing ent-kaurene is provided, which comprises the expression construct(s) for preparing ent-kaurene. Preferably, the kit may further comprise the expression construct for strengthening the precursor pathway of a steviol glycoside. Alternatively, the kit may comprise the host cell for synthesizing ent-kaurene.

The other aspects of the present invention will be apparent to the skilled artisan based on the above aspects of the present invention.

DESCRIPTION OF FIGURES

FIG. 1 shows the structure of steviol glycosides.
FIG. 2 shows the biosynthesis procedure of rebaudioside A.
FIG. 3A shows the structure of plasmid pET28a-ggpps with the insertion site being NcoI/HindIII.
FIG. 3B shows the plasmid pET21c-Inserted gene, wherein the inserted genes include cdps, cps/ks, ks, ko, kah, ugt85c2, ugtb1, ugt74g1 and ugt76g1, each of which was inserted between NdeI/HindIII.
FIG. 3C shows the structure of the plasmid pET21d-cpr, with insertion site being NcoI/HindIII.
FIG. 3D shows the structure of the plasmid pJF47 (pET21d-dxs-ispD-ispF-idi).

SPECIFIC MODE FOR CARRYING OUT THE INVENTION

Figure 3F:
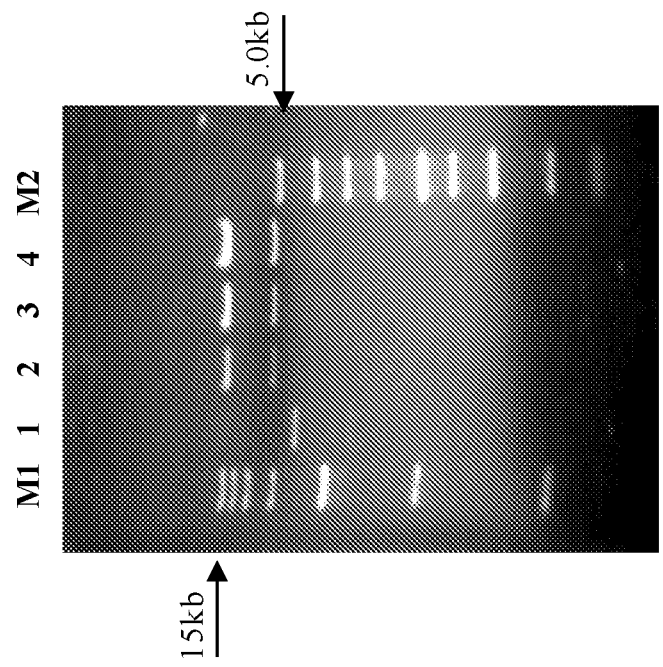
FIG. 3F shows the restriction map of the plasmid pZQ110.

After thoughtful investigation by the present inventors, the present invention firstly reveals a key enzymes used for heterologous biosynthesis of steviol glycosides, thereby realizing heterologous biosynthesis of a steviol glycoside.

Terms

As used herein, the "steviol glycosides" refers to a compound selected from steviol, steviolmonoside, steviolbioside, Stevioside, rebaudioside A or rebaudioside B.

As used herein, the "gene expression cassette" refers to a gene expression system comprising all essential elements required for expressing a target polypeptide, i.e., the enzyme in the subject invention. It generally comprises a promoter, a gene sequence encoding the polypeptide and a terminator. Optionally, it can further comprise a sequence encoding a signal peptide, etc. All the sequences are operably linked.

As used herein, the "operably linked" refers to the functional spatial arrangement of two or more nucleic acid regions or nucleotide sequences. For example, the promoter region is arranged at a special position in relative to the nucleic acid of the target gene to allow direction of the transcription of the nucleic acid by the promoter region. As such, the promoter region is "operably linked" to the nucleic acid of the target gene.

As used herein, the "expression construct" refers to a recombinant DNA molecule, which comprises a desired nucleic acid coding sequence. The construct may comprise one or more gene expression cassette(s). And the "construct" generally is contained within an expression vector.

As used herein, the "heterologous" refers to the relationship between two or more nucleic acids or proteins which are from different sources, or the relationship between the proteins (or nucleic acids) from different sources and the host cells. For example, if the combination of a nucleic acid and a host cell does not exist naturally, the nucleic acid is heterologous to the host cell. A specific sequence is "heterologous" to a cell or an organism into which it is inserted.

Proteins in the Synthetic Pathway and their Expression Systems

The prevent invention relates to the geranylgeranyl diphosphate synthase, ent-copalyl diphosphate synthase, ent-kaurene synthase, bifunctional ent-kaurene synthase (optionally, ent-copalyl diphosphate synthase and ent-kaurene synthase), ent-kaurene oxidase, kaurenoic acid-13α-hydroxylase, UGT85C2 glycosyltransferase, UGT74G1 glycosyltransferase, UGT76G1 glycosyltransferase, UGTB1 glycosyltransferase and cytochrome P450 redox protein involved in the synthesis of the steviol glycoside. Co-expression of the above proteins could synthesize the steviol glycoside. Preferably, enzymes that strengthen the precursor pathway at the upstream of the synthetic pathway are also involved, which may be any enzyme that converts pyruvic acid (PYR) and glyceraldehyde 3-phosphate (G3P) precursors in the central metabolic pathway to the common precursors for synthesis of terpenoids, including isopentenyl diphosphate (IPP) and dimethylallyl diphosphate (DMAPP). Preferably, the enzymes for strengthening the precursor pathway include 1-deoxy-D-xylulose-5-phosphate synthase (DXS), 2-C-methyl-D-erythritol 4-phosphate cytidylyltransferase (CMS), 2-C-methyl-D-erythritol 2,4-cyclodiphosphate synthase (MCS) and isopentenyl-diphosphate delta-isomerase (IDI).

The inventors have also investigated the efficiency of enzymes from different sources for use in synthesis of an intermediate, ent-kaurene, and a final product, a steviol glycoside. Enzymes with excellent results were obtained. Therefore, as a preferred embodiment of the present invention, the geranylgeranyl diphosphate synthase is obtained from *Taxus canadensis* or *Stevia rebaudiana*, preferably from *Taxus Canadensis*; the ent-copalyl diphosphate synthase is obtained from *Stevia rebaudiana* or *Bradyrhizobium japonicum*, preferably from *Stevia rebaudiana*; the ent-kaurene synthase is obtained from *Stevia rebaudiana* or *Bradyrhizobium japonicum*, preferably from *Stevia rebaudiana*; the bifunctional ent-kaurene synthase is obtained from *Physcomitrella patens* or *Gibberella fujikuroi*, preferably from *Physcomitrella patens*; the ent-kaurene oxidase is obtained from *Stevia rebaudiana*, *Gibberella fujikuroi*, *Arabidopsis thaliana*, or *Bradyrhizobium japonicum*, preferably from *Stevia rebaudiana*; the kaurenoic acid-13α-hydroxylase, UGT85C2 glycosyltransferase, UGT74G1 glycosyltransferase and UGT76G1 glycosyltransferase are from *Stevia rebaudiana*; the UGTB1 glycosyltransferase is obtained from *Starmerella bombicola*; and the IGBT glycosyltransferase is from *Ipomoea batatas*; or the cytochrome P450 redox protein is obtained from *Artemisia annua*, *Phaeosphaeria sp.*, *Gibberella fujikuroi*, *Stevia rebaudiana*, or *Arabidopsis thaliana*, preferably from *Phaeosphaeria sp.* As a more preferred embodiment of the present invention, the bifunctional ent-kaurene synthase is used; and the geranylgeranyl diphosphate synthase is obtained from *Taxus canadensis*, the bifunctional ent-kaurene synthase is obtained from *Physcomitrella patens*; the ent-kaurene oxidase, kaurenoic acid-13α-hydroxylase, UGT85C2 glycosyltransferase, UGT74G1 glycosyltransferase and UGT76G1 glycosyltransferase are from *Stevia rebaudiana*; the UGTB1 glycosyltransferase is obtained from *Starmerella bombicola*; and the cytochrome P450 redox protein is obtained from *Phaeosphaeria sp.*

As a more preferred embodiment of the present invention, the geranylgeranyl diphosphate synthase from *Taxus canadensis* has its transit-peptide sequence removed from its N terminus in relative to the wild type sequence. Preferably, the 98 amino acid residues at the N terminus are truncated. The cytochrome P450 redox protein from *Artemisia annua* has its transmembrane domain removed from its N terminus in relative to the wild type sequence. Preferably, the 66 amino acid residues at the N terminus are truncated.

In the present invention, the above enzymes or proteins may be naturally occurring enzymes or proteins. For example, they may be isolated or purified from animals, plants or microorganisms. The enzymes or proteins may also be artificially prepared. For example, the recombinant enzymes or proteins may be produced by the conventional genetic engineering recombinant technique. Preferably, recombinant enzymes or proteins are used in the present invention.

Any suitable enzyme or protein can be used in the present invention. The enzyme or protein includes the full-length enzyme or protein or their biologically active fragments (or called as "active fragment"). The active fragments of the bifunctional CPS/KS enzyme having CDPS and KS activities include YDTAWXA (SEQ ID NO: 61), DXDD (SEQ ID NO: 62), and DDXXD (SEQ ID NO: 63), or YDTAWXA (SEQ ID NO: 64), DXDD (SEQ ID NO: 65), and DEXXE (SEQ ID NO: 66). The active fragments of the UGTB1 glycosyltransferase include GHVGP (SEQ ID NO: 67) and NGGYGG (SEQ ID NO: 68). The amino acids of the enzyme or protein formed by substitution, deletion or addition of one or more amino acid residue are also encompassed by the present invention. The biologically active fragment of an enzyme or a protein refers to a polypeptide which retains the whole or partial function of the full-length enzyme or protein. Generally, the biologically active fragment retains at least 50% activity of the full-length enzyme or protein. More preferably, the active fragment can retain 55%, 60%, 65%, 70%, 75%, 80%, 85%, 90%, 95%, 97%, 99% or 100% activity of the full-length enzyme or protein. The enzyme or protein or biologically active fragment thereof may include some conservative substitutions. The activity of the sequence having said substitutions will not be affected or the sequence retains a partial activity. It is a common knowledge in the art to suitably replace an amino acid residue, which could readily be practiced with the biological activity of the resultant molecule being not changed. The skilled artisan will realize, based on these techniques, that generally changing one single amino acid in the non-essential region of a polypeptide will basically not change the biological activity of the polypeptide. See Watson et al., Molecular Biology of The Gene, 4$^{th}$ Edition, 1987, The Benjamin/Cummings Pub. Co. P224.

The present invention can also use the modified or improved enzyme or protein. For example, the enzyme or protein being modified or improved to promote its half life, efficacy, metabolism and/or potency of protein can be used. The modified or improved enzyme or protein may be a conjugate, or may comprise substituted or artificial amino acid(s). The modified or improved enzyme or protein may be significantly different from the naturally occurring enzyme or protein, but can still have the same or basically identical function to the wild type enzyme or protein and will not produce the other un-favored effect. In other words, any variants that do not affect the biological activity of the enzyme or protein may be used in the present invention.

The present invention also encompasses isolated nucleic acid that encodes the biologically active fragment of the enzyme or protein, or its complementary strand. As a preferred embodiment of the present invention, the coding sequence of each enzyme or protein may be subjected to codon optimization to enhance expression efficiency. The DNA sequence encoding the biologically active fragment of the enzyme or protein may be obtained by artificial synthesis of the whole sequence or may be obtained by PCR amplification. After obtaining the DNA sequence that encodes the biologically active fragment of the enzyme or protein, the DNA sequence is linked into a suitable expression construct, such as an expression vector. The construct is then transferred into a suitable host cell. The transformed host cell is cultivated to produce the desired protein.

The present invention also includes the expression construct comprising a nucleic acid that encodes the biologically active fragment of the enzyme or protein. The expression construct may comprise one or more gene expression cassette(s) encoding the enzyme or protein, and additionally, expression regulatory sequences operably linked to the nucleic acid molecule to facilitate the expression of the protein. Techniques for designing the expression regulatory sequences are known in the art. In the expression regulatory sequence, an inducible promoter or a constitutive promoter can be used as needed. The inducible promoter can be used for more controllable protein expression and production of compound, which is beneficial for the industrial application.

As a preferred embodiment of the present invention, an expression construct is provided, which comprises the gene expression cassette(s) of the following enzymes: the gene expression cassette(s) of the following enzymes: geranylgeranyl diphosphate synthase (GGPPS); an enzyme selected from (I) ent-copalyl diphosphate synthase (CDPS) and ent-kaurene synthase (KS) and (II) bifunctional ent-kaurene synthase (CPS/KS); ent-kaurene oxidase (KO); cytochrome P450 redox protein (CPR); kaurenoic acid-13α-hydroxylase; UGT85C2 glycosyltransferase; and UGTB1/IBGT glycosyltransferase. More preferably, the expression construct may further comprise the gene expression cassette(s) of the following enzymes: UGT74G1 glycosyltransferase; and/or UGT76G1 glycosyltransferase.

Technique for establishing an expression construct was well known in the art. Therefore, after determining the desired enzyme or protein, the skilled artisan can readily construct their expression construct. The gene sequence encoding enzyme or protein may be inserted into different expression constructs, such as expression vectors, or may be inserted into the same expression construct, as long as the enzyme or protein can be effectively expressed after transfecting into cells.

Additionally, the recombinant cell comprising a nucleic acid sequence encoding the biologically active fragment of the enzyme or protein is also encompassed in the present invention. The "host cell" may include prokaryotic cell and eukaryotic cell. Common prokaryotic host cell include $E.$ $coli$ and $Bacillus$ $subtilis$, etc. Common eukaryotic host cell includes yeast, insect cell and mammal cell. As a preferred embodiment of the present invention, the cell is selected from, but is not limited to, gram negative DE3 lysogenic strain and yeast cell. More preferably, the gram negative DE3 lysogenic strain is, but is not limited to, $E.$ $coli$ and $Bacillus$ $subtilis$. More preferably, the $E.$ $coli$ is selected from the group consisting of BL21(DE3), BLR(DE3), DH10B(DE3), HMS(DE3), C43(DE3), JM109(DE3), DH5a (DE3) or Noveblue(DE3). More preferably, the yeast may be (but is not limited to) $Pichia$ $pastoris$, $Saccharomyces$ $cerevisiae$, or $Kluyveromyces$ $lactis$. Preferably, $Pichia$ $pastoris$ may be selected from GS115, MC100-3, SMD1163, SMD1165, SMD1168 or KM71. Preferably, $Saccharomyces$ $cerevisiae$ may be selected from W303, CEN.PK2, S288c, FY834 or S1949. Preferably, $Kluyveromyces$ $lactis$ may be GG799.

Suitable expression vector for used in bacterial cell or fungal cell were known in the art. Therefore, the skilled artisan can readily select a suitable expression vector for use as a backbone vector for cloning the coding gene. For example, when the cell is a bacterial cell, pET series expression vectors, such as pET28a, can be used to recombinantly express each enzyme. And when the cell is a yeast cell, the pPICC series expression vectors, such as pPICC3.5, or the pSY series expression vectors, such as pSY01, could be used.

Conventional techniques known in the art can be used to transform a host cell with a recombinant DNA. When the host is a prokaryotic organism, such as $E.$ $coli$, the competent cells that can adsorb DNA can be harvested after exponential growth by treated by, such as $CaCl_2$ or $MgCl_2$. The steps as used are well known in the art. If required, transformation can be carried out by electroporation. When the host is a eukaryotic cell, the following DNA Transformation methods could be used: calcium phosphate co-precipitation method and conventional mechanical methods, such as microinjection, electroporation and liposomal packaging.

The resultant transformant could be cultured by a conventional method for expressing the enzyme or protein encoded by the gene of the present invention. Based on the used host cell, the culture medium used can be selected from various conventional culture mediums. Host cells are cultured under conditions suitable for their growth.

Methods for Synthesizing Steviol Glycosides

Disclosed is a method for heterologous synthesis of a steviol glycoside by Microorganism. Enzymes involved in the biosynthesis of a steviol glycoside, which are from different sources, are artificially combined together by techniques of synthetic biology to obtain the steviol glycoside, including rebaudioside A, in a host cell.

The biosynthesis process for synthesizing a steviol glycoside, as disclosed in the present invention, is shown in FIG. 2. Pyruvic acid (PYR) and glyceraldehyde 3-phosphate (G3P) in the central metabolic pathway are used as precursors to obtain the common precursors for synthesis of terpenoids: isopentenyl diphosphate (IPP) and dimethylallyl diphosphate (DMAPP). Ent-kaurene is obtained sequentially through geranylgeranyl diphosphate synthase (GGPPS, encoded by ggpps), ent-copalyl diphosphate synthase (CDPS, encoded by cdps), and ent-kaurene synthase (KS, encoded by ks). Preferably, CDPS and KS are replaced by the bifunctional ent-kaurene synthase (CPS/KS, encoded by cps/ks). Thereafter, kaurene is catalyzed to kaurenoic acid by cytochrome P450 redox protein and ent-kaurene oxidase (KO, encoded by ko), and kaurenoic acid is oxidized by kaurenoic acid hydroxylase (KAH, encoded by kah) to obtain the core structure of diterpene, steviol. Steviol is converted to steviolmonoside via UGT85C2 glycosyltransferase and steviolmonoside is further glycosylated to produce steviolbioside. Steviolbioside is converted to stevioside by UGT74G1 glycosyltransferase and stevioside is converted to rebaudioside A via the UGT76G1 glycosyltransferase.

Heterologous biosynthesis of steviol glycosides was firstly achieved by the present inventors by using the above enzymes. UGTB1/IBGT glycosyltransferases, which could incorporate a glycosyl group to the C-2' site at the C-13 glucose of steviolmonoside, are specifically used to convert steviolmonoside to steviolbioside. Thus, the technical problem of the prior art that steviolmonoside cannot be converted to steviolbioside is solved. The glycosyltransferases required for converting steviolmonoside to steviolbioside in one glycosylation step in the biosynthesis of a steviol glycoside were not known in the prior art. After thoughtful investigation by screening a lot of glycosyltransferase genes, the present inventors finally found that UGTB1 or IBGT glycosyltransferase could further glycosylate the C-2' site in the C-13 glucose of the substrate.

Suitable UGTB1/IBGT glycosyltransferases can function as uridine-5'-diphosphoglucosyl: steviol-13-O-glucosyltransferase (also called as steviol-13-monoglucoside 1,2-glucosylase) to transfer a glucose moiety to the C-2' of the 13-O-glucose of the receptor molecule, the steviol-13-glucoside.

Generally, suitable UGTB1/IBGT glycosyltransferases can function as uridine-5'-diphosphoglucosyl: rubusoside transferase to transfer a glucose moiety to the C-2' of the 13-O-glucose of the receptor molecule, rubusoside.

Suitable UGTB1/IBGT glycosyltransferases can further catalyze the reaction utilizing stevioside substrate other than steviol-13-O-glucoside and rubusoside. For example, they can utilize stevioside as a substrate to transfer a glucose moiety to the C-2' of the 19-O-glucose residue to produce rebaudioside E. They can also use rebaudioside A as a substrate to transfer a glucose moiety to the C-2' of the 19-O-glucose residue to produce rebaudioside D. However, UGTB1/IBGT glycosyltransferases generally will not transfer a glucose moiety to a steviol compounds having 1,3-bound glucose at the C-13 position, that is, will not transfer a glucose moiety to steviol 1,3-diglycoside and 1,3-stevioside.

Suitable UGTB1/IBGT glycosyltransferases can transfer a glucose moiety except for uridine diphosphoglucose. For example, suitable UGTB1/IBGT glycosyltransferases can function as uridine 5'-diphosphoric acid D-xylosyl: steviol-13-O-glucoside transferase to transfer the xylose moiety to C-2' of the 13-O-glucose of the receptor molecule, steviol-13-O-glucoside. In another example, suitable UGTB1/IBGT glycosyltransferases can function as uridine 5'-diphosphoric acid L-rhamnosyl: steviol-13-O-glucoside transferase to transfer the rhamnose moiety to C-2' of the 13-O-glucose of the receptor molecule, steviol-13-O-glucoside.

The common precursors IPP and DMAPP for synthesis of terpenoids can be obtained via known techniques in the art. As a preferred embodiment of the present invention, to obtain IPP and DMAPP, the inventors simplify the technical solutions known in the prior art which utilize genes such as dxr, ispE, ispG and ispH, etc. Specifically, in the present invention, pyruvic acid (PYR) and glyceraldehyde 3-phosphate (G3P) precursors in the central metabolic pathway are used as precursors, and the common precursors for synthesis of terpenoids, isopentenyl diphosphate (IPP) and dimethylallyl diphosphate (DMAPP), are obtained through the 1-deoxyxylose-5-phosphoric acid pathway, which orderly includes catalytic synthesis by 1-deoxy-D-xylulose-5-phosphate synthase (DXS, encoded by the dxs gene), 2-C-methyl-D-erythritol 4-phosphate cytidylyltransferase (CMS, encoded by the ispD gene), and 2-C-methyl-D-erythritol 2,4-cyclodiphosphate synthase (MCS, encoded by the ispF gene). With the isopentenyl-diphosphate delta-isomerase (encoded by the idi gene), IPP and DMAPP can be converted to each other.

Method for Synthesizing Ent-Kaurene

The steviol glycoside is a reaction product, the backbone of which is a diterpene compound, ent-kaurene. Ent-kaurene is a major intermediate product. Enhanced production efficiency of ent-kaurene will facilitate highly effective synthesis of the down-stream steviol glycoside.

To improve the efficiency of synthesizing kaurene, the inventors finally find, after repeated experiments, that the efficiency of synthesizing kaurene could be significantly improved by replacing ent-copalyl diphosphate synthase (CDPS) and ent-kaurene synthase (KS) by the bifunctional ent-kaurene synthase (CPS/KS), which is a bifunctional enzyme having the CDPS and KS activities.

The Effective Results of the Present Invention

By utilizing the methods of the present invention, the yield of the crucial intermediate product, ent-kaurene, can reach 1 g/L or more, and the yield of rebaudioside A can reach 10 mg/L or more. The methods of the present invention can be used to replace the plant extraction method to obtain steviol glycosides, especially rebaudioside A which is of great market value. Thus, the subject invention has a wide application prospect and development potential.

As compared to the traditional extraction from plant, which is time-consuming, sensitive to environment and deleterious to the natural resources, the subject application has advantages of low cost, small production area and easy control of product quantity.

The subject invention is further illustrated by making reference to the specific Examples. It should be understood that these examples are provided for illustrate the invention but not for limit the scope of the invention. The experimental method in the examples, in which the specific conditions are not indicated, is practiced generally according to Joseph Sambrook, Molecular Cloning: A Laboratory Manual, the 3$^{th}$ edition, Science Press, 2002, or according to the conditions recommended by the manufacturer. Unless otherwise indicated, the percentage and part are calculated by weight.

Example 1

Obtaining the Proteins Used in the Heterologous Biosynthesis of a Steviol Glycoside Gene sources and synthesis of the geranylgeranyl diphosphate synthase, ent-copalyl diphosphate synthase, ent-kaurene synthase, bifunctional ent-kaurene synthase, ent-kaurene oxidase, kaurenoic acid-13α-hydroxylase, UGT85C2 glycosyltransferase, UGTB1 glycosyltransferase, UGT74G1 glycosyltransferase, UGT76G1 glycosyltransferase, and cytochrome P450 redox protein involved in the synthesis of a steviol glycoside, rebaudioside A.

Geranylgeranyl diphosphate synthase (GGPPS) from *Taxus canadensis* and *Stevia rebaudiana*; ent-copalyl diphosphate synthase (CDPS) from *Stevia rebaudiana* and *Bradyrhizobium japonicum*; ent-kaurene synthase (KS) from *Stevia rebaudiana* and *Bradyrhizobium japonicum*; bifunctional ent-kaurene synthase (CPS/KS) from *Physcomitrella patens* and *Gibberella fujikuroi*; ent-kaurene oxidase (KO) from *Stevia rebaudiana, Gibberella fujikuroi, Arabidopsis thaliana* and *Bradyrhizobium japonicum*; kaurenoic acid hydroxylase (KAH), UGT85C2 glycosyltransferase, UGT74G1 glycosyltransferase and UGT76G1 glycosyltransferase from *Stevia rebaudiana*; UGTB1 glycosyltransferase from *Starmerella bombicola*; IBGT glycosyltransferase from *Ipomoea batatas*; and cytochrome P450 redox protein from *Artemisia annua, Phaeosphaeria* sp. L487, *Stevia rebaudiana, Arabidopsis thaliana* and *Gibberella fujikuroi* were selected from NCBI. Table 2 shows the information of the selected enzymes.

TABLE 2

Genes Involved in the Heterologous Pathway Construction

| Name of Gene | Genbank No. | Source |
| --- | --- | --- |
| GGPP synthase | AAD16018 | *Taxus canadensis* |
| GGPP synthase | ABD92926.2 | *Stevia rebaudiana* |
| ent-copalyl diphosphate synthase | AAB87091 | *Stevia rebaudiana* |
| ent-copalyl diphosphate synthase | BAC47414 | *Bradyrhizobium japonicum* |
| ent-kaurene synthase | AAD34294 | *Stevia rebaudiana* |
| ent-kaurene synthase | BAC47415 | *Bradyrhizobium japonicum* |
| bifunctional ent-kaurene synthase | BAF61135 | *Physcomitrella patens* |
| bifunctional ent-kaurene synthase | Q9UVY5.1 | *Gibberella fujikuroi* |
| bifunctional ent-kaurene synthase | CAH18005.1 | *Fusarium proliferatum* |
| bifunctional ent-kaurene synthase | BAA22426 | *Phaeosphaeria* sp. L487 |
| bifunctional ent-kaurene synthase | CAP07655 | *Sphaceloma manihoticola* |
| ent-kaurene oxidase | AAQ63464 | *Stevia rebaudiana* |
| ent-kaurene oxidase | O94142.1 | *Gibberella fujikuroi* |
| ent-kaurene oxidase | AF047719 | *Arabidopsis thaliana* |
| ent-kaurene oxidase | NP_768785 | *Bradyrhizobium japonicum* |
| kaurenoic acid-13α-hydroxylase | ABD60225 | *Stevia rebaudiana* |
| kaurenoic acid-13α-hydroxylase | AEH65419 | *Stevia rebaudiana* |
| kaurenoic acid-13α-hydroxylase | AED93376.1 | *Arabidopsis thaliana* |
| kaurenoic acid-13α-hydroxylase | AED93377.1 | *Arabidopsis thaliana* |
| UGT85C2 glycosyltransferase | AAR06916 | *Stevia rebaudiana* |

TABLE 2-continued

Genes Involved in the Heterologous Pathway Construction

| Name of Gene | Genbank No. | Source |
| --- | --- | --- |
| UGT74G1 glycosyltransferase | AAR06920 | *Stevia rebaudiana* |
| UGT76G1 glycosyltransferase | AAR06912 | *Stevia rebaudiana* |
| UGTB1 glycosyltransferase | ADT71703 | *Starmerella bombicola* |
| cytochrome P450 redox protein | ABM88789 | *Artemisia annua* |
| cytochrome P450 redox protein | BAG85333 | *Phaeosphaeria* sp. L487 |
| cytochrome P450 redox protein | CAE09055.1 | *Gibberella fujikuroi* |
| cytochrome P450 redox protein | ABB88839 | *Stevia rebaudiana* |
| cytochrome P450 redox protein | X66016 | *Arabidopsis thaliana* |
| IBGT glycosyltransferase | ABL74480.1 | *Ipomoea batatas* |

The coding sequences of the selected enzymes were optimized by conventional optimization method, such as Optimizer (genomes.urv.es/OPTIMIZER). These enzymes were synthesized as follows.

The amino acid sequence of the geranylgeranyl diphosphate synthase (GGPPS) from *Taxus Canadensis* is shown in SEQ ID NO: 1. The 98 amino acid residues (transit-peptide sequence) at the N terminus of the wild type GGPP synthase were removed and a methionine was added, so as to obtain the modified recombinant GGPP synthase. Then codon optimization was carried out and the optimized DNA sequence is shown in SEQ ID NO: 2.

The amino acid sequence of ent-copalyl diphosphate synthase (CDPS) from *Stevia rebaudiana* is shown in SEQ ID NO: 3, and the DNA sequence obtained after codon optimization is shown in SEQ ID NO: 4.

The amino acid sequence of ent-kaurene synthase (KS) from *Stevia rebaudiana* is shown in SEQ ID NO: 5, and the DNA sequence obtained after codon optimization is shown in SEQ ID NO: 6.

The amino acid sequence of ent-kaurene oxidase (KO) from *Stevia rebaudiana* is shown in SEQ ID NO: 7, and the DNA sequence obtained after codon optimization is shown in SEQ ID NO: 8.

The amino acid sequence of kaurenoic acid-13α-hydroxylase (KAH) from *Stevia rebaudiana* is shown in SEQ ID NO: 9, and the DNA sequence obtained after codon optimization is shown in SEQ ID NO: 10.

The amino acid sequence of UGT85C2 glycosyltransferase from *Stevia rebaudiana* is shown in SEQ ID NO: 11, and the DNA sequence obtained after codon optimization is shown in SEQ ID NO: 12.

The amino acid sequence of UGT74G1 glycosyltransferase from *Stevia rebaudiana* is shown in SEQ ID NO: 13, and the DNA sequence obtained after codon optimization is shown in SEQ ID NO: 14.

The amino acid sequence of UGT76G1 glycosyltransferase from *Stevia rebaudiana* is shown in SEQ ID NO: 15, and the DNA sequence obtained after codon optimization is shown in SEQ ID NO: 16.

The amino acid sequence of cytochrome P450 redox protein (CPR) from *Artemisia annua* is shown in SEQ ID NO: 17, with the 66 amino acid residues at the N terminus of wild type CPR protein being truncated and the N terminus of the CPR protein (AAU10466) from *C. tropicalis* being added to obtain the modified CPR protein of the subject invention. The DNA sequence obtained after codon optimization is shown in SEQ ID NO: 18.

The amino acid sequence of cytochrome P450 redox protein from *Phaeosphaeria* is shown in SEQ ID NO: 19, and the DNA sequence obtained after codon optimization is shown in SEQ ID NO: 20.

The amino acid sequence of bifunctional ent-kaurene synthase (CPS/KS) from *Physcomitrella patens* is shown in SEQ ID NO: 21, and the DNA sequence obtained after codon optimization is shown in SEQ ID NO: 22.

The amino acid sequence of bifunctional ent-kaurene synthase (CPS/KS) from *Gibberella fujikuroi* is shown in SEQ ID NO: 23, and the DNA sequence obtained after codon optimization is shown in SEQ ID NO: 24.

The amino acid sequence of ent-copalyl diphosphate synthase from *Bradyrhizobium japonicum* is shown in SEQ ID NO: 25, and the DNA sequence obtained after codon optimization is shown in SEQ ID NO: 26.

The amino acid sequence of ent-kaurene synthase from *Bradyrhizobium japonicum* is shown in SEQ ID NO: 27, and the DNA sequence obtained after codon optimization is shown in SEQ ID NO: 28.

The amino acid sequence of ent-kaurene oxidase from *Bradyrhizobium japonicum* is shown in SEQ ID NO: 29, and the DNA sequence obtained after codon optimization is shown in SEQ ID NO: 30.

The amino acid sequence of ent-kaurene oxidase from *Gibberella fujikuroi* is shown in SEQ ID NO: 31, and the DNA sequence obtained after codon optimization is shown in SEQ ID NO: 32.

The amino acid sequence of cytochrome P450 redox protein from *Gibberella fujikuroi* is shown in SEQ ID NO: 33, and the DNA sequence obtained after codon optimization is shown in SEQ ID NO: 34.

The amino acid sequence of cytochrome P450 redox protein from *Stevia rebaudiana* is shown in SEQ ID NO: 35, and the DNA sequence obtained after codon optimization is shown in SEQ ID NO: 36.

The amino acid sequence of ent-kaurene oxidase from *Arabidopsis thaliana* is shown in SEQ ID NO: 37, and the DNA sequence obtained after codon optimization is shown in SEQ ID NO: 38.

The amino acid sequence of cytochrome P450 redox protein from *Arabidopsis thaliana* is shown in SEQ ID NO: 39, and the DNA sequence obtained after codon optimization is shown in SEQ ID NO: 40.

The amino acid sequence of UGTB1 glycosyltransferase from *Starmerella bombicola* is shown in SEQ ID NO: 41, and the DNA sequence obtained after codon optimization is shown in SEQ ID NO: 42.

The amino acid sequence of kaurenoic acid-13α-hydroxylase (KAH) from *Stevia rebaudiana* is shown in SEQ ID NO: 43, and the DNA sequence obtained after codon optimization is shown in SEQ ID NO: 44.

The amino acid sequence of the geranylgeranyl diphosphate synthase (GGPPS) from *Stevia rebaudiana* is shown in SEQ ID NO: 45, the DNA sequence obtained after codon optimization is shown in SEQ ID NO: 46.

The amino acid sequence of kaurenoic acid-13α-hydroxylase (KAH) from *Arabidopsis thaliana* (Genbank accession No. AED93376.1) is shown in SEQ ID NO: 47, and the DNA sequence obtained after codon optimization is shown in SEQ ID NO: 48.

The amino acid sequence of kaurenoic acid-13α-hydroxylase (KAH) from *Arabidopsis thaliana* (Genbank accession No. AED93377.1) is shown in SEQ ID NO: 49, and the DNA sequence obtained after codon optimization is shown in SEQ ID NO: 50.

The amino acid sequence of glycosyltransferase from *Ipomoea batatas* (Genbank accession No. ABL74480.1) is shown in SEQ ID NO: 51, and the DNA sequence obtained after codon optimization is shown in SEQ ID NO: 52.

Optimized DNA sequences of other proteins can be obtained by the same method.

Furthermore, the inventors analyzed the sequence homology of the proteins from different source, which were identified to have the same function. Table 3 shows the results.

TABLE 3

Homology Analysis of Amino Acids from Different Sources

| Protein | Source | Homology (NCBI blastP) |
|---|---|---|
| GGPPS | *Stevia rebaudiana* vs. *Taxus Canadensis* | 68% |
| CDPS | *Stevia rebaudiana* vs. *Physcomitrella patens* | 50% |
| CDPS | *Stevia rebaudiana* vs. *Gibberella fujikuroi* | 58% |
| CDPS | *Stevia rebaudiana* vs. *Bradyrhizobium japonicum* | 57% |
| KS | *Stevia rebaudiana* vs. *Bradyrhizobium japonicum* | 43% |
| KO | *Stevia rebaudiana* vs. *Bradyrhizobium japonicum* | 55% |
| KO | *Stevia rebaudiana* vs. *Gibberella fujikuroi* | 25% |
| KO | *Stevia rebaudiana* vs. *Arabidopsis thaliana* | 61% |
| CPR | *Stevia rebaudiana* vs. *Phaeosphaeria* sp. L487 | 34% |
| CPR | *Stevia rebaudiana* vs. *Gibberella fujikuroi* | 75% |
| CPR | *Stevia rebaudiana* vs. *Arabidopsis thaliana* | 66% |
| KS | *Stevia rebaudiana* vs. *Physcomitrella patens* | 36% |
| KS | *Stevia rebaudiana* vs. *Gibberella fujikuroi* | 64% |
| CPS/KS | *Gibberella fujikuroi* vs. *Physcomitrella patens* | 34% |
| KS vs. CPS/KS | KS: *Stevia rebaudiana* vs. CPSKS: *Physcomitrella patens* | 36% |
| KS vs. CPS/KS | KS: *Stevia rebaudiana* vs.CPSKS: *Gibberella fujikuroi* | 64% |
| UGTB1 vs. UGT85C2 | UGTB1: *Starmerella bombicola* vs. UGT85C2: *Stevia rebaudiana* | 33% |
| UGTB1 vs. UGT74G1 | UGTB1: *Starmerella bombicola* vs. UGT74G1: *Stevia rebaudiana* | 83% |
| UGTB1 vs. UGT76G1 | UGTB1: *Starmerella bombicola* vs. UGT76G1: *Stevia rebaudiana* | 45% |
| IBGT vs. UGT85C2 | IBGT: *Ipomoea batatas* vs. UGT85C2: *Stevia rebaudiana* | 31% |
| IBGT vs. UGT74G1 | IBGT: *Ipomoea batatas* vs. UGT74G1: *Stevia rebaudiana* | 36% |
| IBGT vs. UGT76G1 | IBGT: *Ipomoea batatas* vs. UGT76G1: *Stevia rebaudiana* | 28% |
| UGTB1 vs. IBGT | UGT76G1: *Starmerella bombicola* vs. IBGT: *Ipomoea batatas* | 22% |

From Table 3, it can be found that the proteins from different sources but having the same function have low homology. For example, CDPS from *Stevia rebaudiana* has only 50% and 58% homology, respectively, to CPS/KS having CDPS and KS bifunctional enzymatic activity from *Physcomitrella patens* and *Gibberella fujikuroi*. KS from *Stevia rebaudiana* has only 36% and 64% homology, respectively, to CPS/KS having CDPS and KS bifunctional enzymatic activity from *Physcomitrella patens* and *Gibberella fujikuroi*. Furthermore, the UGTB1 glycosyltransferase from *Starmerella bombicola* has only 33%, 83% and 45% homology, respectively, to UGT85C2 glycosyltransferase, UGT74G1 glycosyltransferase and UGT76G1 glycosyltransferase from *Stevia rebaudiana*.

CPS/KS from several fungal sources has relatively high homology, but CPS/KS from *Physcomitrella patens* has a relatively low homology. Nevertheless, all of them contain regions rich in aspartic acid, which are fragments having CPS and KS enzymatic activity. The active fragment of CPS starts from YDTAWXA with an N terminal sequence of DXDD; while the active fragment of KS starts from DDXXD or DEXXE at the C terminus, wherein X is any amino acid. The active fragments of UGTB1 include GHVGP, which locates at positions 16 to 20, and NGGYGG, which locates at positions 338 to 343.

Example 2

Construction of the Prokaryotic Expression Vector

The optimized genes of geranylgeranyl diphosphate synthase, ent-copalyl diphosphate synthase, ent-kaurene synthase, bifunctional ent-kaurene synthase, ent-kaurene oxidase, kaurenoic acid-13α-hydroxylase, UGT85C2 glycosyltransferase, UGT74G1 glycosyltransferase, UGT76G1 glycosyltransferase and cytochrome P450 redox protein were cloned into related plasmids to construct the gene expression vectors used in the rebaudioside A synthesis pathway in bacterium.

A SpeI restriction site was inserted after the terminator codon TAA of the optimized ggpps gene, then the resultant gene was cloned into plasmid pET28a (Novagen) at the NcoI/HindIII restriction site to produce pET28a-ggpps (FIG. 3A).

The SpeI site was inserted after the terminator codon TAA of the optimized cdps, cps/ks, ks, ko, kah, ugt85c2, ugtb1, ugt74g1, and ugt76g1, respectively, then the resultant genes were cloned into pET21a (Novagen), respectively, at the NdeI/BamHI site, to obtain pET21a-cdps, pET21a-cps/ks, pET21a-ks, pET21a-ko, pET21a-kah, pET21a-ugt85c2, pET21a-ugtb1, pET21a-ugt74g1, and pET21a-ugt76g1, respectively (see FIG. 3B). In FIG. 3B, the inserted genes refer to cdps, cps/ks, ks, ko, kah, ugt85c2, ugtb1, ugt74g1 and ugt76g1, which were respectively inserted at the NdeI/HindIII site of individual plasmids.

The SpeI restriction site was inserted after the terminator codon TAA of the optimized cpr gene, then the resultant gene was cloned into plasmid pET21d (Novagen) at the NcoI/HindIII restriction site to produce pET21d-cpr (FIG. 3C).

Figure 3E:
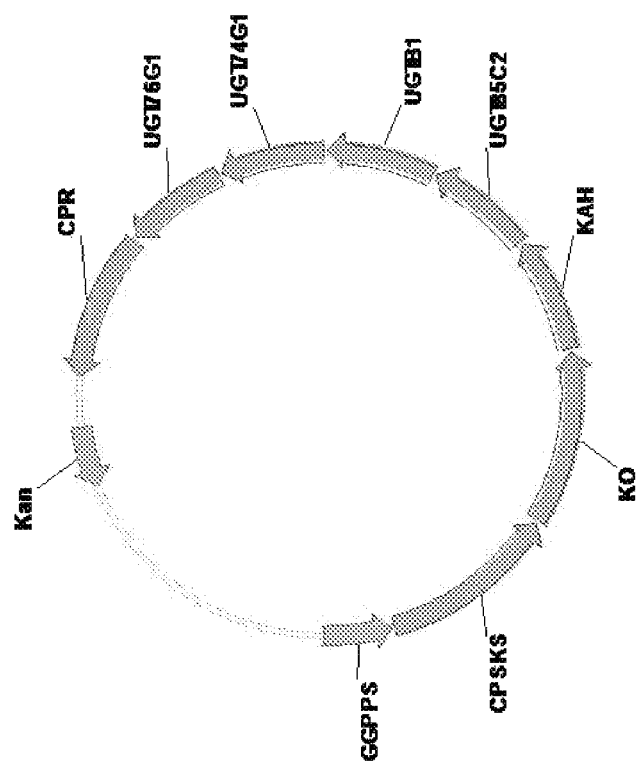
FIG. 3E shows the structure of the plasmid pZQ110 (pET28a-ggpps-cps/ks-ko-kah-ugt85c2-ugtb1-ugt74g1-ugt76g1-cpr).

As an example, the plasmid pZQ110 was constructed as follows. The heterologous genes were assembled in series by a method similar to the method provided by the BioBrick Assembly Kit of New England Biolab. Specifically, the plasmid pET28a-ggpps (*Taxus Canadensis*) was digested by SpeI/HindIII and the plasmid pET21a-cps/ks (*Physcomitrella patens*) was digested by XbaI/HindIII. The pET28a-ggpps vector was recovered by PCR purification kit and the cps/ks DNA fragment was recovered by gel. The cps/ks DNA fragment was ligated to the pET28a-ggpps vector by T4 DNA ligase to construct plasmid pET28a-ggpps-cps/ks. The same method was performed to ligate ko (*Stevia rebaudiana*), kah (*Stevia rebaudiana*), ugt85c2 (*Stevia rebaudiana*), ugtb1 (*Starmerella bombicola*), ugt74g1 (*Stevia rebaudiana*), ugt76g1 (*Stevia rebaudiana*) and cpr (*Phaeosphaeria* sp. L487) in series, to obtain a gene expression vector pZQ110 for synthesizing rebaudioside A in bacterium (FIG. 3E). The restriction map of the plasmid (XbaI/HindIII double digestion) was shown in FIG. 3F, in which M1 is Marker 1 with a molecular weight of DS15000, 1 indicates the negative control product, 2-4 indicate pZQ110 products, M2 is Marker 2 with a molecular weight of DS5000. According to FIG. 3F, two bands with molecular weights of 5300/16500 were obtained after digesting the plasmid pZQ110 by XbaI/HindIII. Thus, it can confirm that the pZQ110 was correctly constructed.

Additional recombinant expression plasmids for expressing intermediates or products were also constructed by methods similar to construction of pZQ110, as shown in Table 4.

TABLE 4

Information about the expression plasmids for expressing the genes involved in the synthesis of rebaudioside A in bacterium

| | Plasmids | Whole Name |
|---|---|---|
| Synthesis of ent-kaurene, an intermediate for synthesizing stevia sugar | pZQ3 | pET28a-GGPPS-CDPS-KS<br>GGPPS: *Taxus canadensis* (inserted into pET28a at the NcoI/HindIII site)<br>CDPS: *Stevia rebaudiana* (inserted into the pET28a at the XbaI/HindIII site)<br>KS: *Stevia rebaudiana* (inserted into the pET28a at the XbaI/HindIII site) |
| | pSY32 | pET28a-GGPPS-CPS/KS<br>GGPPS: *Taxus canadensis* (inserted into the pET28a at the NcoI/HindIII site)<br>CPS/KS: *Physcomitrella patens* (inserted into the pET28a at the XbaI/HindIII site) |
| | pSY33 | pET28a-GGPPS-CPS/KS<br>GGPPS: *Taxus canadensis* (inserted into the pET28a at the NcoI/HindIII site)<br>CPS/KS: *Gibberella fujikuroi* (inserted into the pET28a at the XbaI/HindIII site) |
| | pZQ101 | pET28a-GGPPS-CPS/KS<br>GGPPS: *Stevia rebaudiana* (inserted into the pET28a at the NcoI/HindIII site)<br>CPS/KS: *Physcomitrella patens* (inserted into the pET28a at the XbaI/HindIII site) |
| | pZQ102 | pET28a-GGPPS-CPS/KS<br>GGPPS: *Stevia rebaudiana* (inserted into the pET28a at the NcoI/HindIII site)<br>CPS/KS: *Gibberella fujikuroi* (inserted into the pET28a at the XbaI/HindIII site) |
| Synthesis of steviolmonoside | pZQ104 | pET28a-GGPPS-CDPS-KS-KO-KAH-CPR-UGT85C2<br>GGPPS: *Taxus canadensis* (inserted into the pET28a at the NcoI/HindIII site)<br>CDPS: *Stevia rebaudiana* (inserted into the pET28a at the XbaI/HindIII site)<br>KS: *Stevia rebaudiana* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site) |
| | pZQ105 | pET28a-GGPPS-CPS/KS-KO-KAH-CPR-UGT85C2<br>GGPPS: *Taxus canadensis* (inserted into the pET28a at the NcoI/HindIII site)<br>CPS/KS: *Physcomitrella patens* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site) |
| | pZQ106 | pET28a-GGPPS-CPS/KS-KO-KAH-CPR-UGT85C2<br>GGPPS: *Taxus canadensis* (inserted into the pET28a at the NcoI/HindIII site)<br>CPS/KS: *Gibberella fujikuroi* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site) |

TABLE 4-continued

Information about the expression plasmids for expressing the genes involved in the synthesis of rebaudioside A in bacterium

| | Plasmids | Whole Name |
|---|---|---|
| Synthesis of steviolbioside | pZQ107 | pET28a-GGPPS-CDPS-KS-KO-KAH-CPR-UGT85C2-UGTB1<br>GGPPS: *Taxus canadensis* (inserted into the pET28a at the NcoI/HindIII site)<br>CDPS: *Stevia rebaudiana* (inserted into the pET28a at the XbaI/HindIII site)<br>KS: *Stevia rebaudiana* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| | pZQ108 | pET28a-GGPPS-CPS/KS-KO-KAH-CPR-UGT85C2-UGTB1<br>GGPPS: *Taxus canadensis* (inserted into the pET28a at the NcoI/HindIII site)<br>CPS/KS: *Physcomitrella patens* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| | pZQ109 | pET28a-GGPPS-CPS/KS-KO-KAH-CPR-UGT85C2-UGTB1<br>GGPPS: *Taxus canadensis* (inserted into the pET28a at the NcoI/HindIII site)<br>CPS/KS: *Gibberella fujikuroi* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>UGTB1 glycosyltransferase (*Starmerella bombicola*) (inserted into the pET28a at the X XbaI/HindIII site) |
| | pSY200 | pET28a-GGPPS-CDPS-KS-KO-KAH-CPR-UGT85C2-UGTB1<br>GGPPS: *Taxus canadensis* (inserted into the pET28a at the NcoI/HindIII site)<br>CDPS: *Stevia rebaudiana* (inserted into the pET28a at the XbaI/HindIII site)<br>KS: *Stevia rebaudiana* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>IBGT glycosyltransferase (*Ipomoea batatas*) (inserted into the pET28a at the XbaI/HindIII site) |
| | pSY201 | pET28a-GGPPS-CPS/KS-KO-KAH-CPR-UGT85C2-UGTB1<br>GGPPS: *Taxus canadensis* (inserted into the pET28a at the NcoI/HindIII site)<br>CPS/KS: *Physcomitrella patens* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>IBGT glycosyltransferase (*Ipomoea batatas*) (inserted into the pET28a at the XbaI/HindIII site) |
| | pSY202 | pET28a-GGPPS-CPS/KS-KO-KAH-CPR-UGT85C2-UGTB1<br>GGPPS: *Taxus canadensis* (inserted into the pET28a at the NcoI/HindIII site)<br>CPS/KS: *Gibberella fujikuroi* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>IBGT glycosyltransferase (Ipomoea batatas) (inserted into the pET28a at the XbaI/HindIII site) |
| Ligation of the genes involved in the synthesis of stevia sugar for synthesizing rebaudioside A | pZQ9 | pET28a-GGPPS-CDPS-KS-KO-KAH-CPR-UGT85C2--UGTB1-UGT74G1-UGT76G1<br>GGPPS: *Taxus canadensis* (inserted into the pET28a at the NcoI/HindIII site)<br>CDPS: *Stevia rebaudiana* (inserted into the pET28a at the XbaI/HindIII site)<br>KS: *Stevia rebaudiana* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| | pZQ110 | pET28a-GGPPS-CPS/KS-KO-KAH-CPR-UGT85C2-UGTB1-UGT74G1-UGT76G1<br>GGPPS: *Taxus canadensis* (inserted into the pET28a at the NcoI/HindIII site)<br>CPS/KS: *Physcomitrella patens* (inserted into the pET28a at the XbaI/HindIII site) |

TABLE 4-continued

Information about the expression plasmids for expressing the genes involved in the synthesis of rebaudioside A in bacterium

| Plasmids | Whole Name |
|---|---|
| | KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| pZQ120 | pET28a-GGPPS-CPS/KS-KO-KAH-CPR-UGT85C2-UGTB1-UGT74G1-UGT76G1<br>GGPPS: *Taxus canadensis* (inserted into the pET28a at the NcoI/HindIII site)<br>CPS/KS: *Gibberella fujikuroi* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Phaeosphaeria* sp. L487 (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| pZQ111 | pET28a-GGPPS-CPS/KS-KO-KAH-CPR-UGT85C2-UGTB1-UGT74G1-UGT76G1<br>GGPPS: *Taxus canadensis* (inserted into the pET28a at the NcoI/HindIII site)<br>CPS/KS: *Physcomitrella patens* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Stevia rebaudiana* (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| pZQ121 | pET28a-GGPPS-CPS/KS-KO-KAH-CPR-UGT85C2-UGTB1-UGT74G1-UGT76G1<br>GGPPS: *Taxus canadensis* (inserted into the pET28a at the NcoI/HindIII site)<br>CPS/KS: *Gibberella fujikuroi* (inserted into the pET28a at the XbaI/HindIII site)<br>KO: *Stevia rebaudiana* (inserted into the pET28a at the XbaI/HindIII site)<br>KAH: *Stevia rebaudiana* (SEQ ID NO: 44) (inserted into the pET28a at the XbaI/HindIII site)<br>CPR: *Stevia rebaudiana* (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| pZQ112 | pET28a-GGPPS-CPS/KS-KO-KAH-CPR-UGT85C2-UGTB1-UGT74G1-UGT76G1<br>GGPPS: *Taxus canadensis* (inserted into the pET28a at the NcoI/HindIII site)<br>CPS/KS: *Physcomitrella patens* (inserted into the pET28a at the XbaI/HindIII site)<br>KO: *Stevia rebaudiana* (inserted into the pET28a at the XbaI/HindIII site)<br>KAH: *Arabidopsis thaliana* (SEQ ID NO: 44) (inserted into the pET28a at the XbaI/HindIII site)<br>CPR: *Stevia rebaudiana* (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |
| pZQ122 | pET28a-GGPPS-CPS/KS-KO-KAH-CPR-UGT85C2-UGTB1-UGT74G1-UGT76G1<br>GGPPS: *Taxus canadensis* (inserted into the pET28a at the NcoI/HindIII site)<br>CPS/KS: *Gibberella fujikuroi* (inserted into the pET28a at the XbaI/HindIII site)<br>KO: *Stevia rebaudiana* (inserted into the pET28a at the XbaI/HindIII site)<br>KAH: *Arabidopsis thaliana* (SEQ ID NO: 44) (inserted into the pET28a at the XbaI/HindIII site)<br>CPR: *Stevia rebaudiana* (inserted into the pET28a at the XbaI/HindIII site)<br>UGT85C2: *Stevia rebaudiana* (inserted into the pET28a at the XbaI/HindIII site)<br>UGT74G1: *Stevia rebaudiana* (inserted into the pET28a at the XbaI/HindIII site)<br>UGT76G1: *Stevia rebaudiana* (inserted into the pET28a at the XbaI/HindIII site)<br>UGTB1 glycosyltransferase (*Starmerella bombicola*) (inserted into the pET28a at the XbaI/HindIII site) |

Example 3

Construction of the Fungal Expression Vectors

The optimized genes for the geranylgeranyl diphosphate synthase, ent-copalyl diphosphate synthase, ent-kaurene synthase, bifunctional ent-kaurene synthase, ent-kaurene oxidase, kaurenoic acid-13α-hydroxylase, UGT85C2 glycosyltransferase, UGTB1 glycosyltransferase, UGT74G1 glycosyltransferase, UGT76G1 glycosyltransferase, and cytochrome P450 redox protein, obtained in Example 1, were cloned into corresponding plasmids to construct gene expression plasmids for synthesizing rebaudioside A in fungus.

Firstly, the initial pAO815 vector (Invitrogen) was modified by introducing BamHI and XhoI restriction sites after pAO815 terminator by site-directed mutagenesis PCR. The modified pAO815 was named pSY01. The BamHI site in the pET28a-ggpps gene was removed by site-directed mutagenesis PCR and the BglII site in the pET21a-ks gene was removed by site-directed mutagenesis PCR.

The ggpps gene was amplified by PCR by using the pET28a-ggpps as template and introduce the EcoRI restriction sites at its two ends (introduction four A bases before ATG). The PCR fragment and the pSY01 vector were cleaved by EcoRI. The pSY01 vector and the ggpps fragment were recovered by a purification kit. Then the ggpps fragment was ligated to the pSY01 vector by T4 DNA ligase to construct the pSY01-ggpps plasmid.

The cdps gene (*Taxus canadensis*) was amplified by PCR by using the pES21a-cdps as template and introduce the BglII and NotI restriction sites its two ends (introduction 4 A bases before ATG). The PCR fragment was digested by BglII and NotI, and the pPIC3.5K (Invitrogen) was digested by BamHI and NotI. The pPIC3.5K and the cdps fragment were recovered by a purification kit and then the cdps fragment was ligated to the pPIC3.5K vector by T4 DNA ligase to construct pPIC3.5K-cdps. The same method was used to construct cps/ks, ks, ko, kah, ugt85c2, ugt74g1, ugt76g1 and cpr into pPIC3.5K, respectively, at the site indicated as "inserted gene" in the Figures.

Figure 3G:
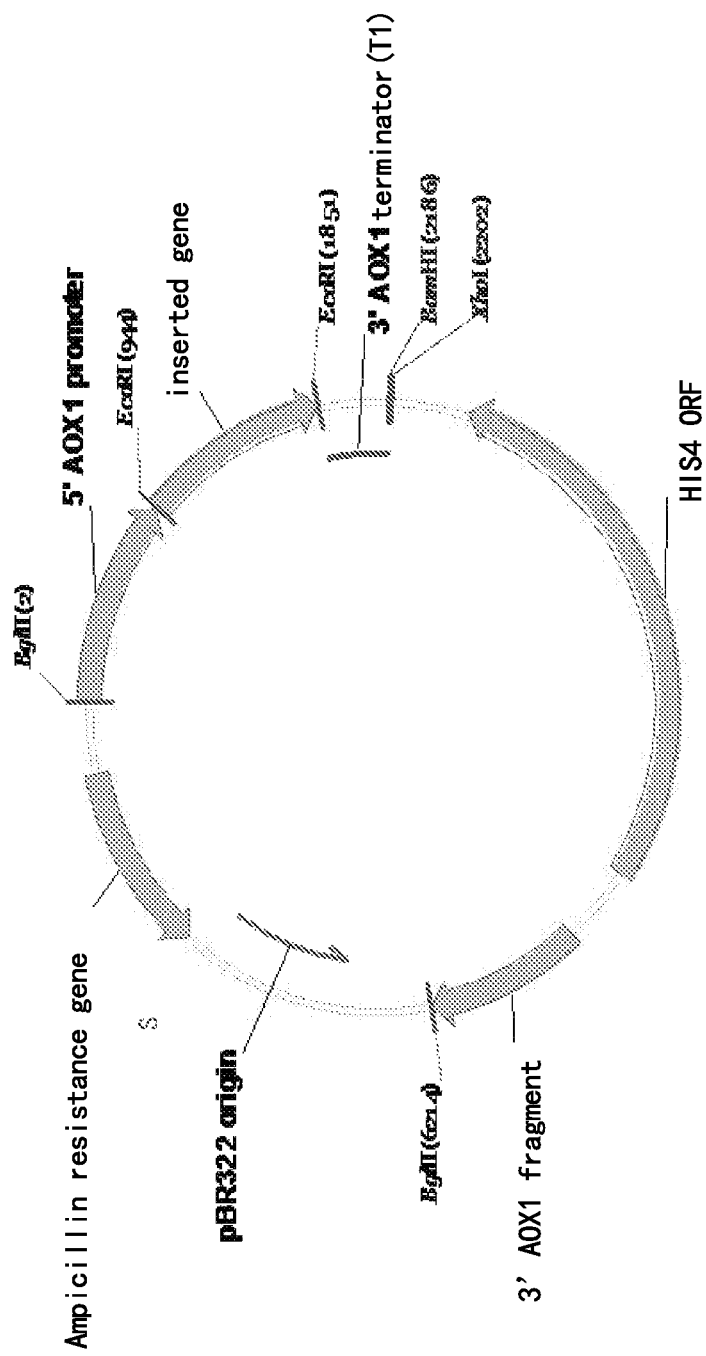
FIG. 3G shows the plasmid pPIC3.5K-Inserted gene, wherein the inserted genes include cdps, cps/ks, ks, ko, kah, ugt85c2, ugtb1, ugt74g1 and ugt76g1, each of which was inserted between BglII/NotII.
Figure 3I:
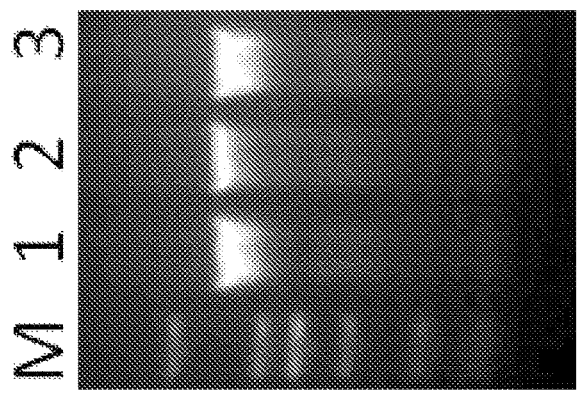
FIG. 3I shows the PCR map of the plasmid pZQ210.
Figure 3H:
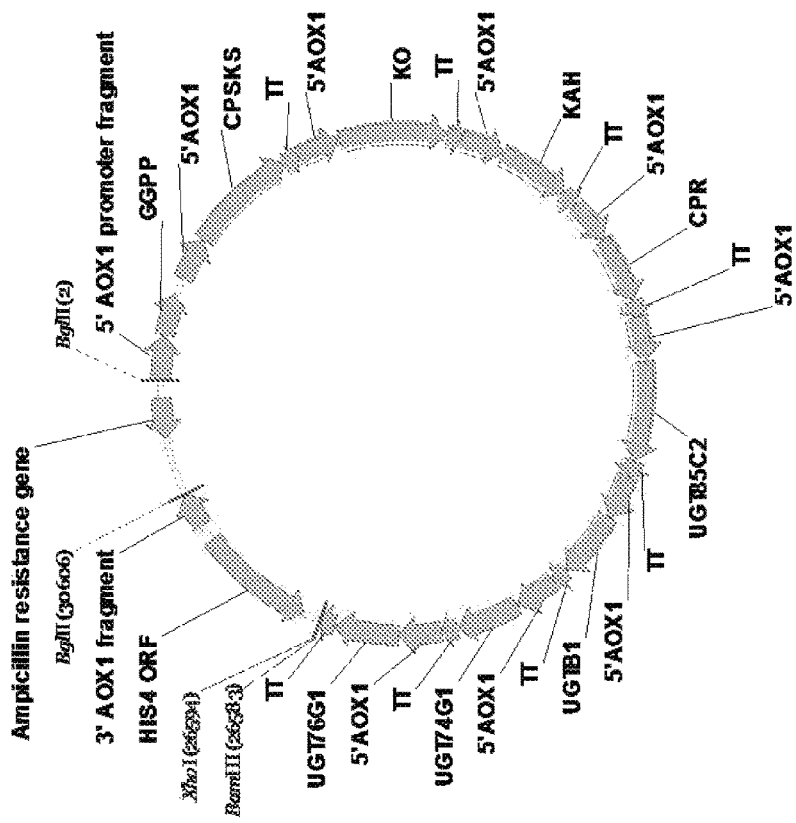
FIG. 3H shows the structure of the plasmid pZQ210 (pSY1-ggpps-cps/ks-ko-kah-ugt85c2-ugtb1-ugt74g1-ugt76g1-cpr).
Figures 4A, 4B:
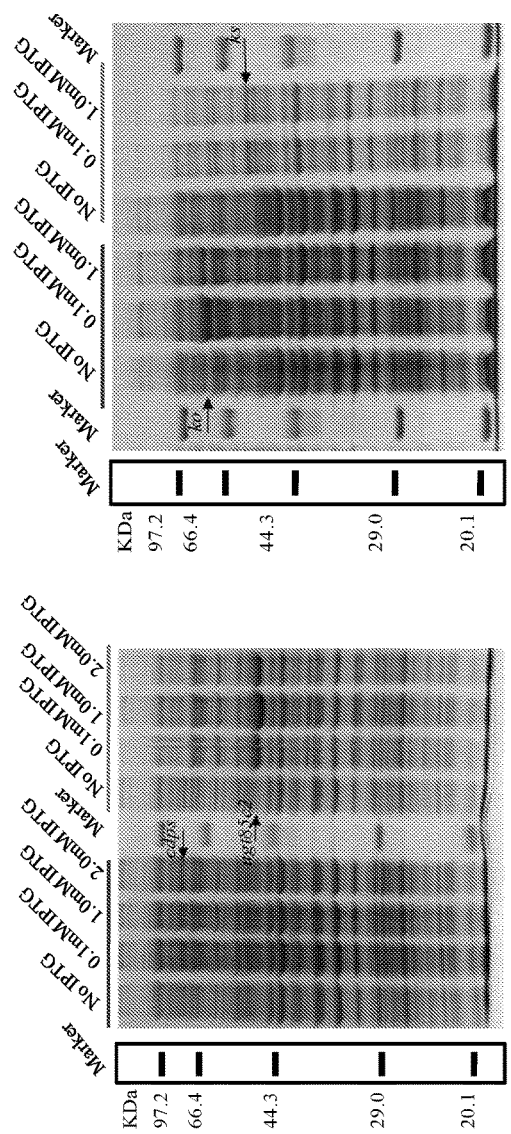
FIG. 4A shows the SDS-PAGE map for expression of the adps gene and ugt85c2 gene.
FIG. 4B shows the SDS-PAGE map for expression of the ko gene and the ks gene.
Figures 4C, 4D, 4E:
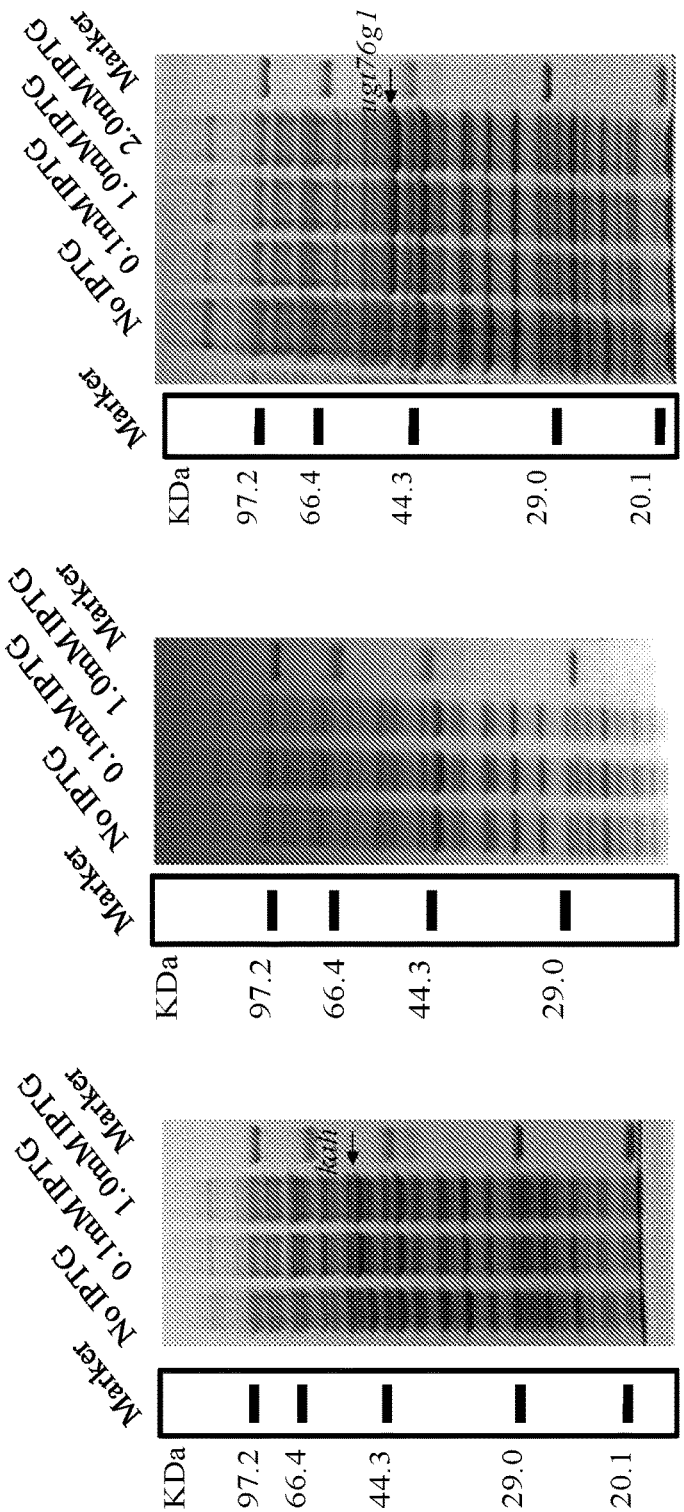
FIG. 4C shows the SDS-PAGE map for expression of the kah gene.
FIG. 4D shows SDS-PAGE map for expression of the ugt74g1 gene.
FIG. 4E shows SDS-PAGE map for expression of the ugt76g1 gene.

The 5' AOX-cps/ks-TT was amplified by PCR by using the pPIC3.5K-cps/ks as template and introduce the B gill and XhoI restriction sites at its two ends. The PCR fragment was digested by BglII and XhoI, and the pSY01-ggpps vector was digested by BamHI and XhoI. The pSY01-ggpps vector and the 5'AOX-cps/ks-TT fragment were recovered by a purification kit and then the 5'AOX-cps/ks-TT fragment was ligated to the pSY01-ggpps vector by T4 DNA ligase to construct a plasmid. The same method was used to ligate cps/ks (*Physcomitrella patens*), ko (*Stevia rebaudiana*), kah (*Stevia rebaudiana*), ugt85c2 (*Stevia rebaudiana*), ugtb1 (*Starmerella bombicola*), ugt74g1 (*Stevia rebaudiana*), ugt76g1 (*Stevia rebaudiana*) and cpr (*Phaeosphaeria* sp. L487) in series to finally obtain the expression plasmid pSY210. See FIG. 3G. FIG. 3I shows the PCR verification map of the plasmid pSY210, in which M1 is Marker with a molecular weight of DS2000, 1 indicates the positive control product, 2 and 3 indicate the pSY210 products. According to FIG. 3I, a band of about 1383 bp was obtained after verifying the pSY210 plasmid by PCR by using primers specific to the full-length coding gene of UGT74G1 glycosyltransferase. Thus, the pSY210 was correctly constructed.

Additional recombinant expression plasmids for expressing intermediates or products were also constructed by methods similar to construction of pZQ210, as shown in Table 5.

TABLE 5

Information about the expression plasmids for expressing the genes involved in the synthesis of rebaudioside A in fungus

| | Names of Plasmids | Alias |
|---|---|---|
| Synthesis of Kaurene | pSY16 | pSY01-GGPP-CDPS-KS<br>GGPP: *Taxus Canadensis* (inserted into the pSY01 at the EcoRI site)<br>CDPS: *Stevia rebaudiana* (inserted into the pSY01 at the BamHI/XhoI site)<br>KS: *Stevia rebaudiana* (inserted into the pSY01 at the BamHI/XhoI site) |
| | pZQ132 | pSY01-GGPP-CPS/KS<br>GGPP: *Taxus Canadensis* (inserted into the pSY01 at the EcoRI site)<br>CPS/KS: *Physcomitrella patens* (inserted into the pSY01 at the BamHI/XhoI site) |
| | pZQ133 | pSY01-GGPP-CPS/KS<br>GGPP: *Taxus Canadensis* (inserted into the pSY01 at the EcoRI site)<br>CPS/KS: *Gibberella fujikuroi* (inserted into the pSY01 at the BamHI/XhoI site) |
| | pZQ201 | pSY01-GGPP-CPS/KS<br>GGPP: *Stevia rebaudiana* (inserted into the pSY01 at the EcoRI site)<br>CPS/KS: *Physcomitrella patens* (inserted into the pSY01 at the BamHI/XhoI site) |
| | pZQ202 | pSY01-GGPP-CPS/KS<br>GGPP: *Stevia rebaudiana* (inserted into the pSY01 at the EcoRI site)<br>CPS/KS: *Gibberella fujikuroi* (inserted into the pSY01 at the BamHI/XhoI site) |
| Ligation of the genes involved in the synthesis of stevia sugar for synthesizing rebaudioside A | pSY22 | pSY01-GGPP-CDPS-KS-KO-KAH-CPR-UGT85C2-UGTB1-UGT74G1-UGT76G1<br>GGPP: *Taxus Canadensis* (inserted into the pSY01 at the EcoRI site)<br>CDPS: *Stevia rebaudiana* (inserted into the pSY01 at the BamHI/XhoI site)<br>KS: *Stevia rebaudiana* (inserted into the pSY01 at the BamHI/XhoI site)<br>KO: *Stevia rebaudiana* (inserted into the pSY01 at the BamHI/XhoI site)<br>KAH: *Stevia rebaudiana* (SEQ ID NO: 10 or SEQ ID NO: 44) (inserted into the pSY01 at the BamHI/XhoI site)<br>CPR: *Phaeosphaeria* sp. L487 (inserted into the pSY01 at the BamHI/XhoI site)<br>UGT85C2: *Stevia rebaudiana* (inserted into the pSY01 at the BamHI/XhoI site)<br>UGT74G1: *Stevia rebaudiana* (inserted into the pSY01 at the BamHI/XhoI site)<br>UGT76G1: *Stevia rebaudiana* (inserted into the pSY01 at the BamHI/XhoI site)<br>UGTB1 glycosyltransferase (inserted into the pSY01 at the BamHI/XhoI site) |
| | pZQ210 | pSY01-GGPP-CPS/KS-KO-KAH-CPR-UGT85C2-UGTB1-UGT74G1-UGT76G1<br>GGPP: *Taxus Canadensis* (inserted into the pSY01 at the EcoRI site)<br>CPS/KS: *Physcomitrella patens* (inserted into the pSY01 at the BamHI/XhoI site)<br>KO: *Stevia rebaudiana* (inserted into the pSY01 at the BamHI/XhoI site)<br>KAH: *Stevia rebaudiana* (SEQ ID NO: 10) (inserted into the pSY01 at the BamHI/XhoI site)<br>CPR: *Phaeosphaeria* sp. L487 (inserted into the pSY01 at the BamHI/XhoI site)<br>UGT85C2: *Stevia rebaudiana* (inserted into the pSY01 at the BamHI/XhoI site)<br>UGT74G1: *Stevia rebaudiana* (inserted into the pSY01 at the BamHI/XhoI site)<br>UGT76G1: *Stevia rebaudiana* (inserted into the pSY01 at the BamHI/XhoI site)<br>UGTB1 glycosyltransferase (inserted into the pSY01 at the BamHI/XhoI site) |

TABLE 5-continued

Information about the expression plasmids for expressing the
genes involved in the synthesis of rebaudioside A in fungus

| Names of Plasmids | Alias |
|---|---|
| pZQ220 | pSY01-GGPP-CPS/KS-KO-KAH-CPR-UGT85C2-UGTB1-UGT74G1-UGT76G1<br>GGPP: *Taxus Canadensis* (inserted into the pSY01 at the EcoRI site)<br>CPS/KS: *Gibberella fujikuroi* (inserted into the pSY01 at the BamHI/XhoI site)<br>KO: *Stevia rebaudiana* (inserted into the pSY01 at the BamHI/XhoI site)<br>KAH: *Stevia rebaudiana* (SEQ ID NO: 44) (inserted into the pSY01 at the BamHI/XhoI site)<br>CPR: *Phaeosphaeria* sp. L487 (inserted into the pSY01 at the BamHI/XhoI site)<br>UGT85C2: *Stevia rebaudiana* (inserted into the pSY01 at the BamHI/XhoI site)<br>UGT74G1: *Stevia rebaudiana* (inserted into the pSY01 at the BamHI/XhoI site)<br>UGT76G1: *Stevia rebaudiana* (inserted into the pSY01 at the BamHI/XhoI site)<br>UGTB1 glycosyltransferase (inserted into the pSY01 at the BamHI/XhoI site) |
| pZQ211 | pSY01-GGPP-CPS/KS-KO-KAH-CPR-UGT85C2-UGTB1-UGT74G1-UGT76G1<br>GGPP: *Taxus Canadensis* (inserted into the pSY01 at the EcoRI site)<br>CPS/KS: *Physcomitrella patens* (inserted into the pSY01 at the BamHI/XhoI site)<br>KO: *Stevia rebaudiana* (inserted into the pSY01 at the BamHI/XhoI site)<br>KAH: *Stevia rebaudiana* (SEQ ID NO: 10) (inserted into the pSY01 at the BamHI/XhoI site)<br>CPR: *Stevia rebaudiana* (inserted into the pSY01 at the BamHI/XhoI site)<br>UGT85C2: *Stevia rebaudiana* (inserted into the pSY01 at the BamHI/XhoI site)<br>UGT74G1: *Stevia rebaudiana* (inserted into the pSY01 at the BamHI/XhoI site)<br>UGT76G1: *Stevia rebaudiana* (inserted into the pSY01 at the BamHI/XhoI site)<br>UGTB1 glycosyltransferase (inserted into the pSY01 at the BamHI/XhoI site) |
| pZQ221 | pSY01-GGPP-CPS/KS-KO-KAH-CPR-UGT85C2-UGTB1-UGT74G1-UGT76G1<br>GGPP: *Taxus Canadensis* (inserted into the pSY01 at the EcoRI site)<br>CPS/KS: *Gibberella fujikuroi* (inserted into the pSY01 at the BamHI/XhoI site)<br>KO: *Stevia rebaudiana* (inserted into the pSY01 at the BamHI/XhoI site)<br>KAH: *Stevia rebaudiana* (SEQ ID NO: 44) (inserted into the pSY01 at the BamHI/XhoI site)<br>CPR: *Stevia rebaudiana* (inserted into the pSY01 at the BamHI/XhoI site)<br>UGT85C2: *Stevia rebaudiana* (inserted into the pSY01 at the BamHI/XhoI site)<br>UGT74G1: *Stevia rebaudiana* (inserted into the pSY01 at the BamHI/XhoI site)<br>UGT76G1: *Stevia rebaudiana* (inserted into the pSY01 at the BamHI/XhoI site)<br>UGTB1 glycosyltransferase (inserted into the pSY01 at the BamHI/XhoI site) |

Example 4

Expression Profiles of Each Gene in *E. coli*

The plasmids pET21a-cdps, pET21a-ks, pET21a-ko, pET21a-kah, pET21a-ugt85c2, pET21a-ugt74g1 and pET21a-ugt76g1 obtained in Example 2 were transformed into host cell BL21(DE3).

Each clone was respectively picked up to 2 ml LB culture medium (100 mg/L ampicillin), cultured at 37° C. overnight, and then inoculated, in 1% (v/v) inoculation amount, to 2 ml fresh LB culture medium supplemented with the same antibiotic. The culture was cultivated at 37° C. until $OD_{600}$ reached 0.3-0.4. IPTG was added to a final concentration of 0.1 mM, and then expression was induced for 6 h at 18° C. After that, each fermentation broth was subjected to SDS-PAGE analysis.

Results were shown in FIGS. 4A, 4B, 4C, 4D and 4E. According to FIG. 4A, the genes cdps and ugt85C2 expressed evidently. According to FIG. 4B, the genes ko and ks expressed evidently. According to FIG. 4C, the kah gene expressed evidently. According to FIG. 4D, the ugt74g1 gene had less expression. And, according to FIG. 4E, the ugt76g1 gene expressed evidently.

Example 5

Transformation of Vectors and Prokaryotic Expression

Host cells, *E. coli* BL21(DE3), were co-transformed by the gene expression plasmids for synthesizing rebaudioside A or intermediates obtained in Example 2 and the expression plasmid pJF47 (FIG. 3D) for strengthening the precursor pathway to produce recombinant *E. coli* BL21(DE3) transformed with the gene expression plasmids for synthesizing rebaudioside A or intermediates and pJF47.

The genome of *E. coli* MG1655 was firstly extracted and then each gene was amplified by using the primers shown in the Table below. Each gene was cloned into the plasmid pET21d at the NcoI/EcoRI site. The pET21c-ispF was digested by SpeI/EcoRI, and the pET21d-idi was digested by XbaI/EcoRI. The pET21c-ispF vector and the idi gene were recovered and ligated together to construct a plasmid pET21d-ispF-idi. The plasmid pET21c-ispD was digested by SpeI/EcoRI, and the pET21d-ispF-idi was digested by XbaI/EcoRI. The pET21c-ispD and ispF-idi gene fragment were recovered and ligated together to construct pET21d-ispD-ispF-idi. pET21d-dxs was digested by SpeI/EcoRI, and pET21d-ispD-ispF-idi was digested by XbaI/EcoRI. The pER21d-dxs and ispD-ispF-idi fragment were recovered and ligated together to construct pET21d-dxs-ispD-ispF-idi, which is designated as pJF47.

| Gene | Genbank No. | Primers | Cloning Site |
|---|---|---|---|
| dxs | NP_414954.1 | dxs-F: CATGCCATGGGCATGAGTTTTGATATTGCCAAATACCCG (SEQ ID NO: 53) | NcoI/EcoRI |
| | | dxs-R: CGGAATTCACTAGTTTATGCCAGCCACCTT (SEQ ID NO: 54) | |
| ispD | NP_417227.1 | ispD-F: CATGCCATGGGCATGGCAACCACTCATTTGGATGTT (SEQ ID NO: 55) | NcoI/EcoRI |
| | | ispD-R: CGGAATTCACTAGTTTATGTATTCTCCTGATGGATGGTT (SEQ ID NO: 56) | |
| ispF | NP_417226.1 | ispF-F: CATGCCATGGGCATGCGAATTGGACACGGTTTTG (SEQ ID NO: 57) | NcoI/EcoRI |
| | | ispF-R: CGGAATTCACTAGTTCATTTTGTTGCCTTAATGAGTAG (SEQ ID NO: 58) | |
| idi | NP_417365.1 | idi-F: CATGCCATGGGCATGCAAACGGAACACGTCATTTTA (SEQ ID NO: 59) | NcoI/EcoRI |
| | | idi-R: CGGAATTCTTATTTAAGCTGGGTAAATGCAG (SEQ ID NO: 60) | |

Clones were picked up to LB liquid culture medium containing ampicillin (100 mg/L) and kanamycin (50 mg/L), and cultured at 37° C. for 8 h. The thalli were collected by centrifugation and 10% (v/v) glycerin were added to prepare an inoculum. The inoculum was stored at −80° C.

The inoculum was inoculated, in 5% (v/v) inoculation amount, into 10 ml M9 culture medium (purchased from Shanghai Sangon, containing 100 mg/L ampicillin and 50 mg/L kanamycin) in a 100 ml shake flask, cultured at 37° C. After the OD reaches about 0.4, 0.05 mM IPTG was added for induction culture. The culture was cultivated at 22° C. for 5 days. The fermentation broth was collected and stored at −80° C.

Example 6

Detection of Ent-Kaurene in Some Recombinant Cells for Synthesizing Ent-Kaurene, an Intermediate for *Stevia* Sugar, Prepared in Example 5

The recombinant *E. coli* BL21(DE3) containing the gene expression plasmids for synthesizing rebaudioside A or intermediates thereof and the expression plasmid pJF47 for strengthening the precursor pathway was fermented for detection ent-kaurene.

50 μl 2M HCl were added into 1 ml fermentation broth of Example 5 and then the same volume of ethyl acetate were added. The mixture was subjected to ultrasonic treatment in an ice bath for 1 min and then vortexed at ambient temperature for 20 min. After that, the mixture was centrifuged at 12000 rpm for 1 min to separate the organic phase. The organic phase was sucked out and the residual water phase was extracted by the same volume of ethyl acetate for one time. The organic phases were pooled and extracted to obtain the product containing ent-kaurene. The ent-kaurene was directly detected by GC-MS.

The ent-kaurene was detected by GC-MS under the conditions as follows: Agilent 7890-5975 GC-MS system was used. The column was HP-5MS, the carrier gas was helium gas. The flow rate was 1 ml/min. The loading amount was 5 μl without splitflow and the loading temperature was 250° C. The warming procedure of the column included: 100° C. for 2 min, warming to 250° C. by 5° C./min, and 250° C. for 15 min. Solvent was loaded in a delay of 4.50 min. Ion scanning (m/z 272) was used for scanning. The dissociation voltage was 70 eV.

Figure 5:
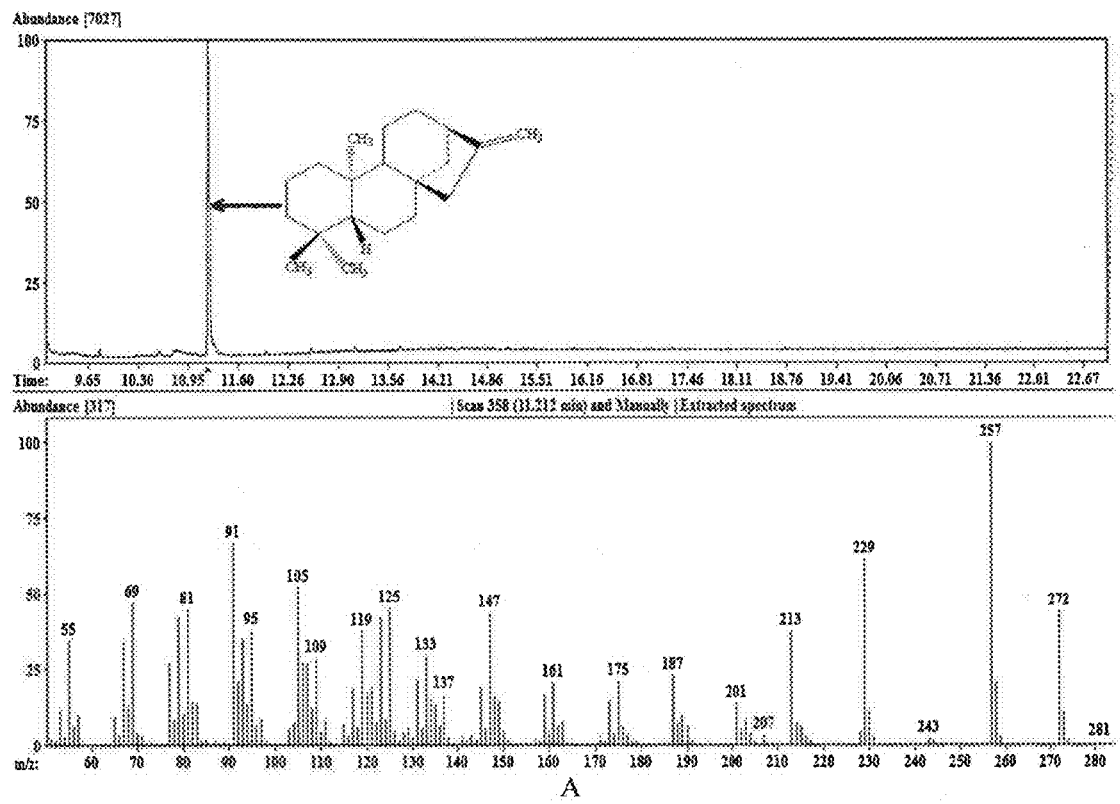
FIG. 5A shows the GC-MS map of ent-kaurene from the fermentation broth of Example 6.
FIG. 5B shows the yield of ent-kaurene from the fermentation broth of Example 6.
Figure 5:
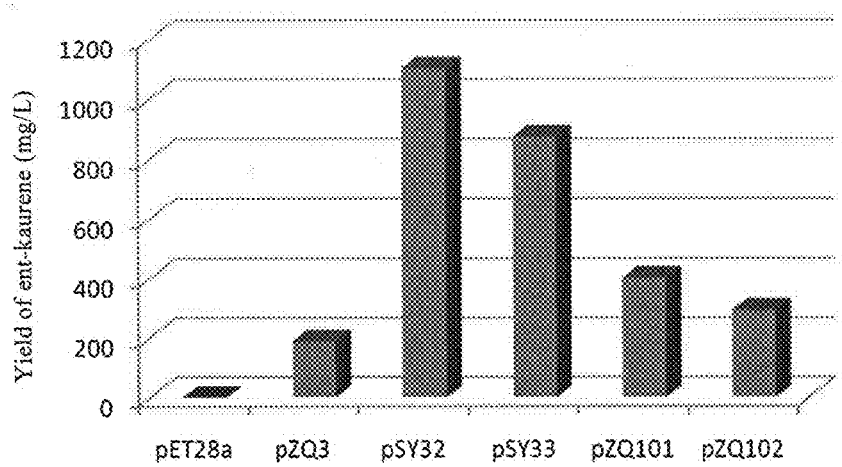
Figure 6A:
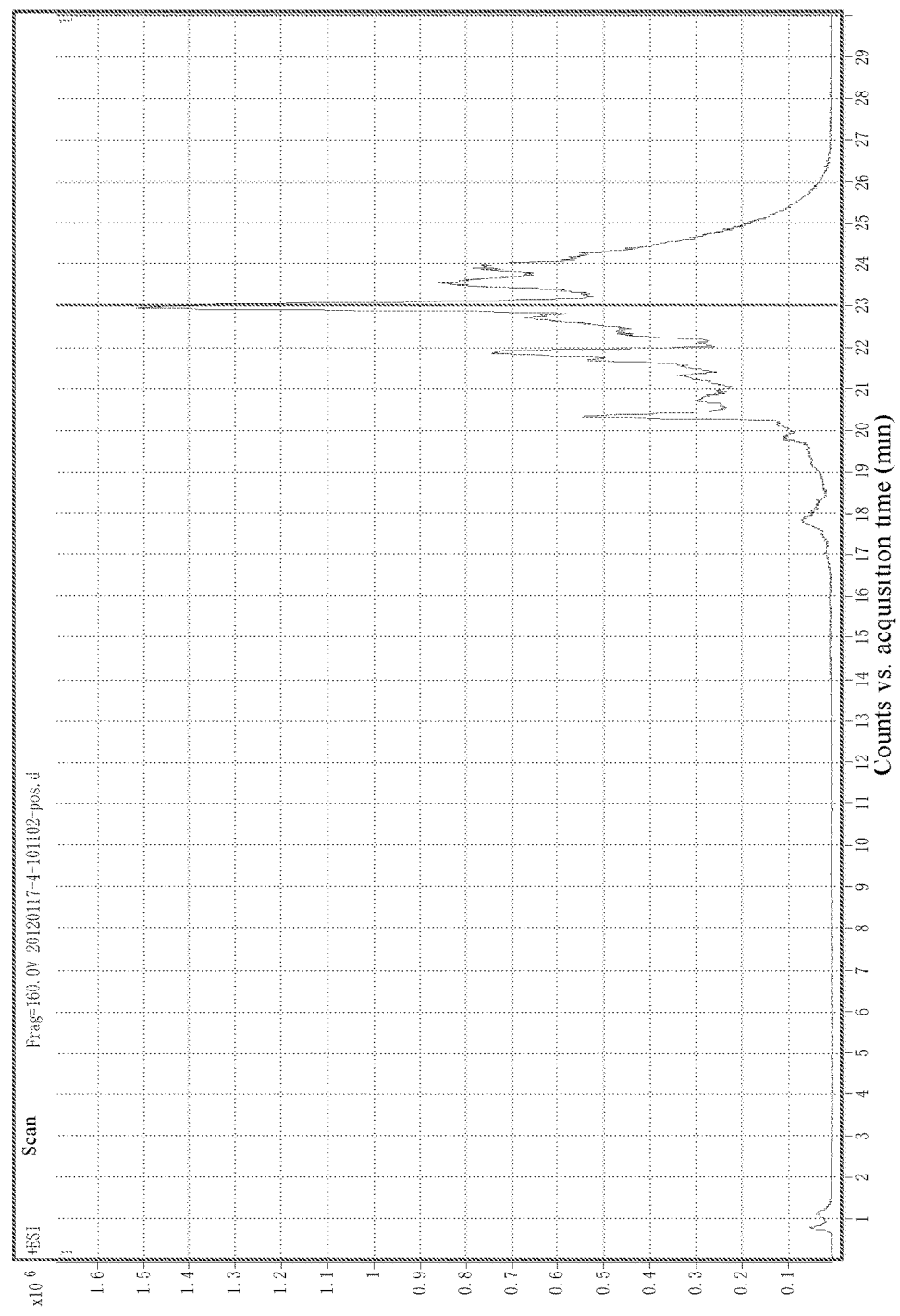
FIG. 6A shows the HPLC map of the fermentation broth of Example 7.
Figure 6B:
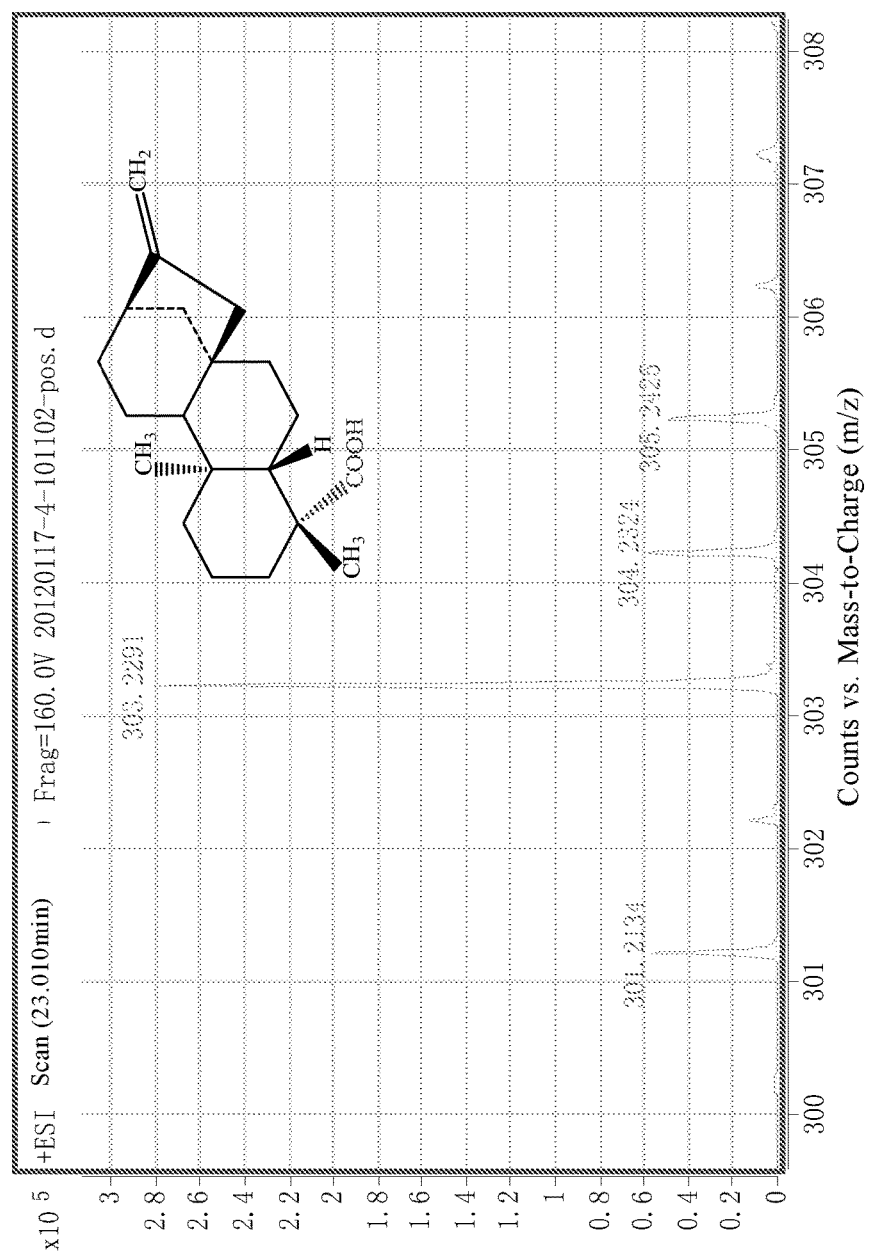
FIG. 6B shows the HPLC-MS map of kaurenoic acid obtained from the fermentation broth of Example 7.
Figure 6C:
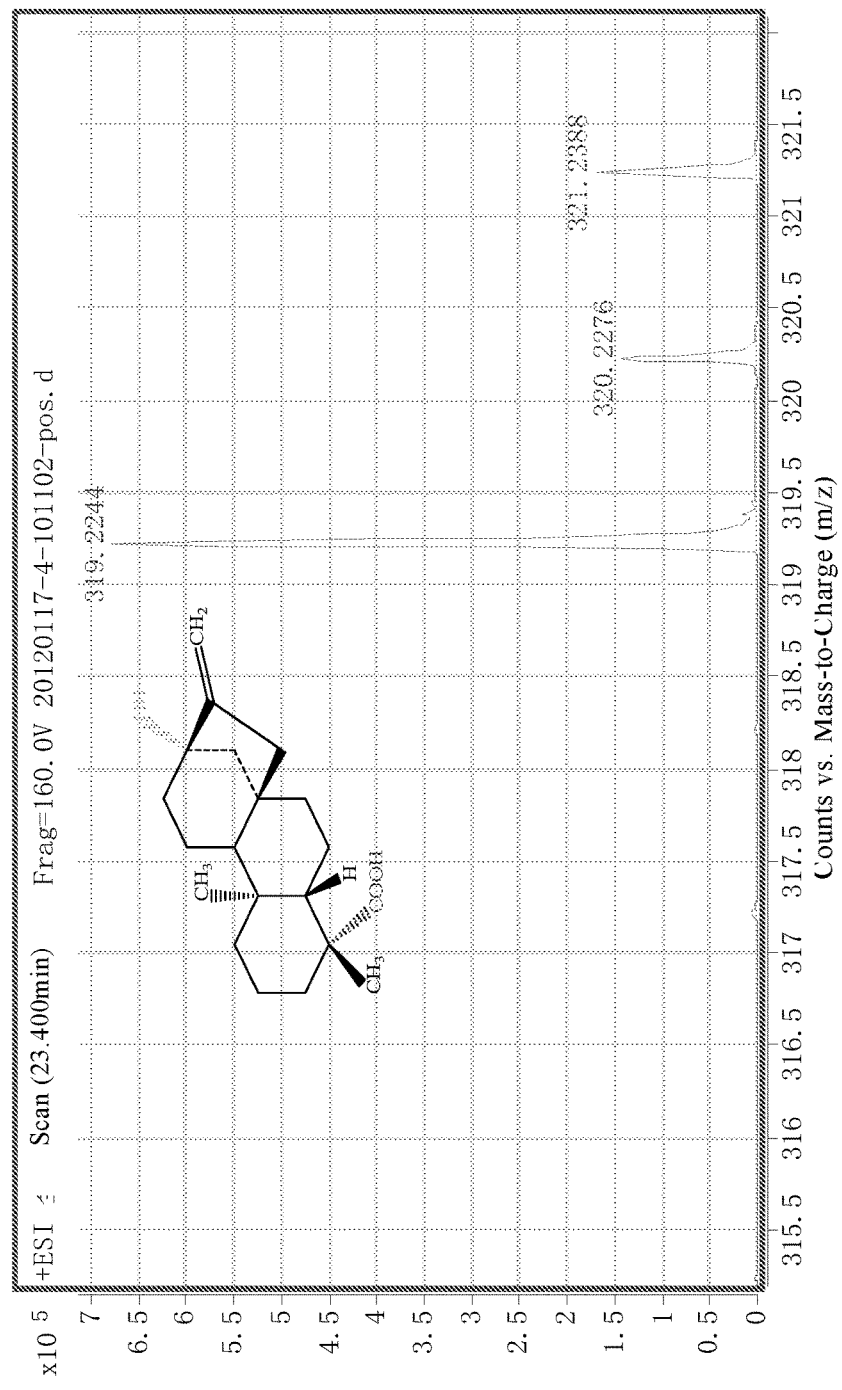
FIG. 6C shows the HPLC-MS map of steviol obtained from the fermentation broth of Example 7.
Figure 6D:
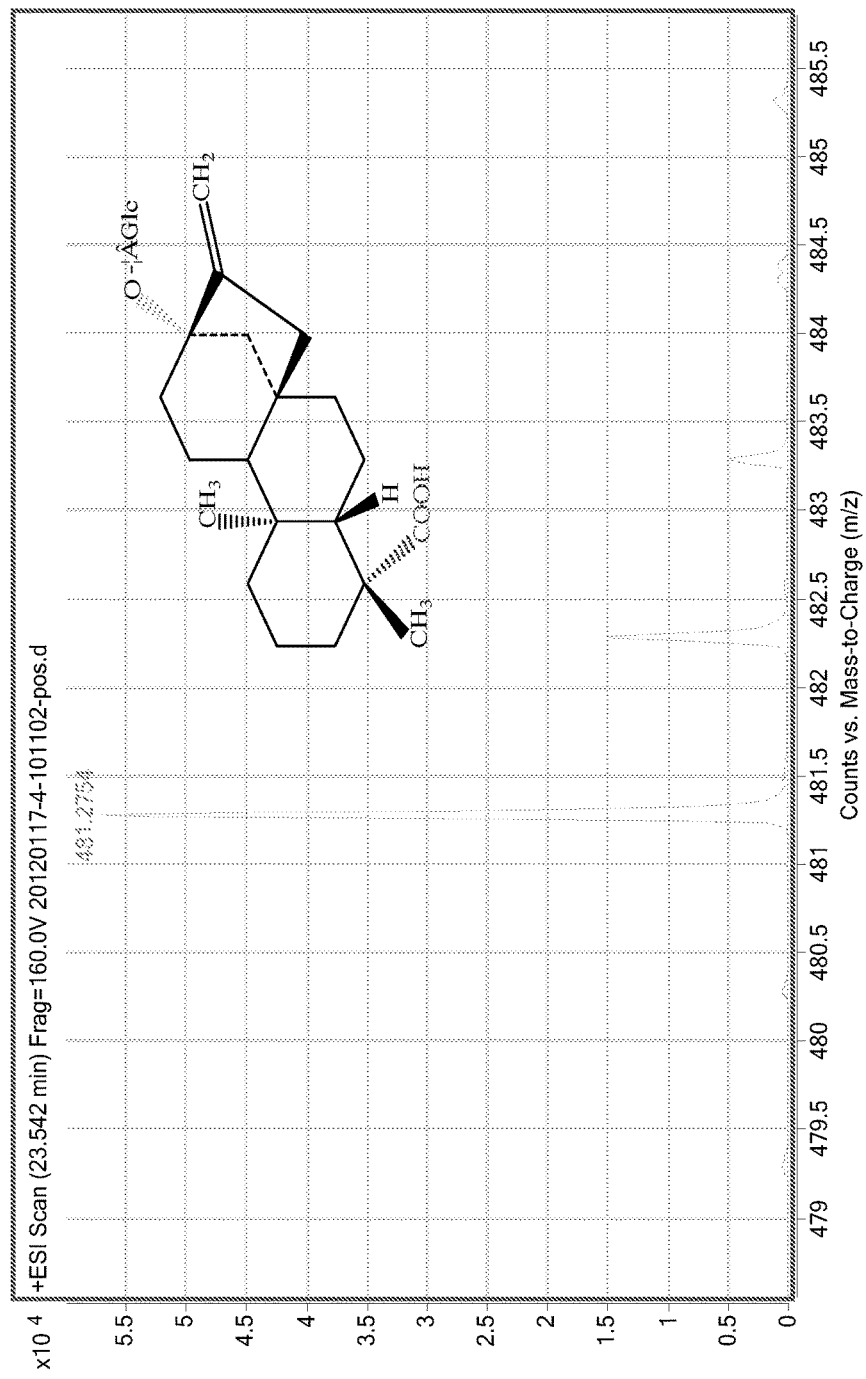
FIG. 6D shows the HPLC-MS map of steviolmonoside obtained from the fermentation broth of Example 7.
Figure 6E:
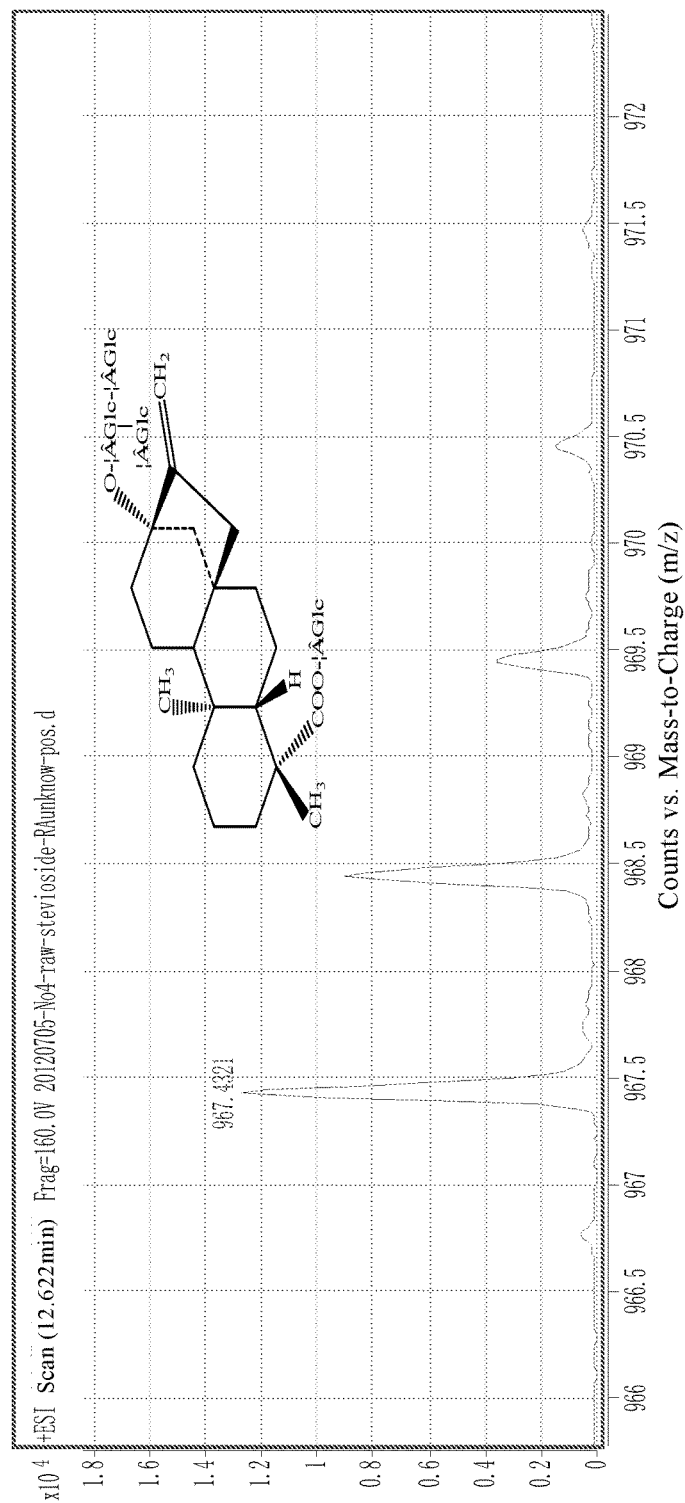
FIG. 6E shows the HPLC-MS map of rebaudioside A obtained from the fermentation broth of Example 7.
Figure 6F:
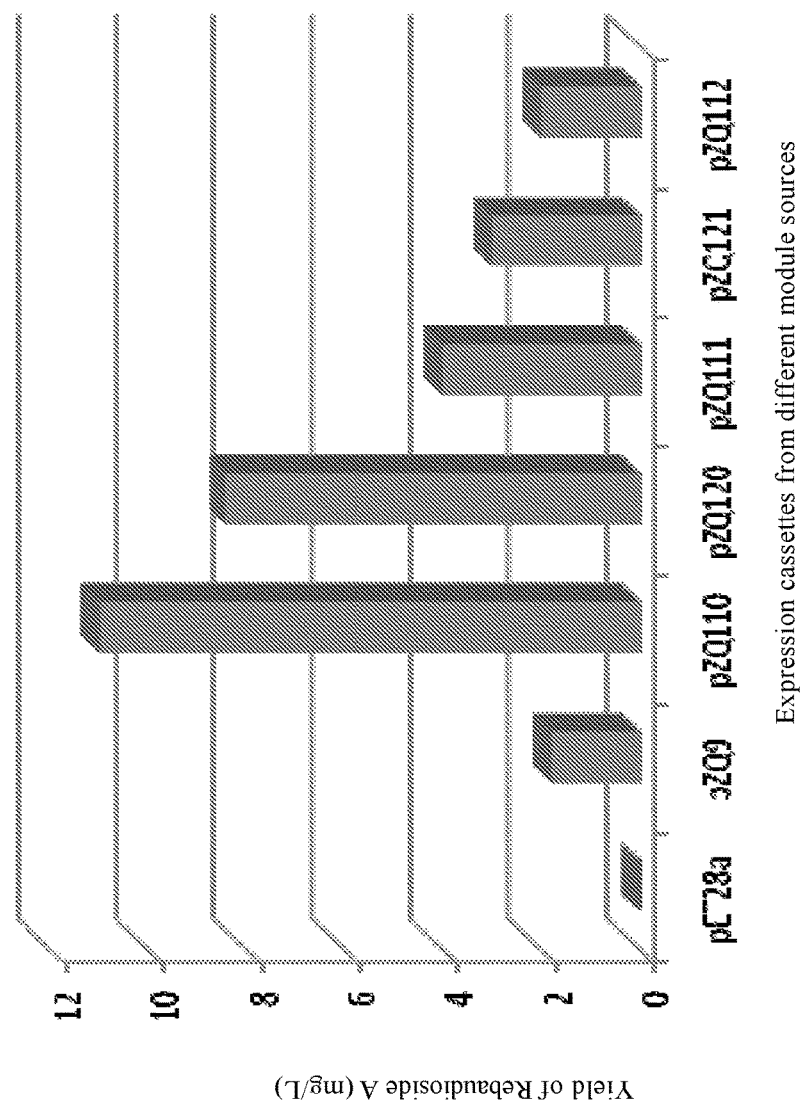
FIG. 6F shows the yield of rebaudioside A obtained from the fermentation broth of Example 7.

The mass spectrogram of ent-kaurene was shown in FIG. 5A. The appearance time of ent-kaurene was 11.212 min. The yield of ent-kaurene produced by the recombinant *E. coli* BL21(DE3) strains transformed by various vectors was shown in FIG. 5B and Table 6.

TABLE 6

The yield of ent-kaurene in a portion of fermentation broth obtained in Examples 6 and 8

| Host | Plasmids | OD$_{600}$ | Yield of ent-kaurene (mg/L) |
|---|---|---|---|
| BL21 (DE3) | pET28a + pJF47 (control, blank plasmid) | 24.7 | 0 |
| BL21 (DE3) | pZQ3 + pJF47 | 31.8 | 189 |
| BL21 (DE3) | pSY32 + pJF47 | 24.0 | 1105 |
| BL21 (DE3) | pSY33 + pJF47 | 24.2 | 876 |
| BL21 (DE3) | pZQ101 + pJF47 | 20.1 | 403 |
| BL21 (DE3) | pZQ102 + pJF47 | 22.3 | 296 |

According to FIG. 6, except the blank vector pET28a, the lowest ent-kaurene yield was obtained by the cells transformed by pZQ3 (GGPP was from *Taxus Canadensis* and CDPS and KS were from *Stevia rebaudiana*), which was merely 189 mg/L. The highest ent-kaurene yield was obtained from the cells transformed by pSY32 (GGPP was from *Taxus Canadensis* and CDPKS were from *Physcomitrella patens*), which was up to 1105 mg/L.

The results show that in the *E. coli* expression system, the bifunctional CPS/KS module was superior in expressing synthetic ent-kaurene than the CDPS and KS modules, and the CPS/KS from *Physcomitrella patens* and GGPPS from *Taxus Canadensis* produce the preferred results.

Example 7

Detection of Product Produced by Some Recombinant Cells for Synthesizing Rebaudioside A Prepared in Example 5

One milliliter ethyl acetate was added into 1 ml fermentation broth of Example 5. The mixture was subjected to ultrasonic treatment in an ice bath for 1 min and then vortexed at ambient temperature for 20 min. After that, the mixture was centrifuged at 12000 rpm for 1 min to separate the organic phase. The organic phase was sucked out and the residual water phase was extracted by the same volume of ethyl acetate for one time. The organic phases were pooled and extracted to obtain the extraction product containing steviol glycosides, including kaurenoic acid, steviol, steviolmonoside and rebaudioside A. The organic phase was dried under vacuum. 500 μl acetonitrile were added to re-dissolve the residues and the product was detected by HPLC-MS.

Steviol glycosides, including kaurenoic acid, steviol, were detected by HPLC-MS (Aglient, LC1200/MS-QTOF6520) equipped with C18 reversed phase chromatographic column (Waters, Xterra, 2.1×50 mm). The mobile A phase is methanol+0.1% formic acid, B phase is water+0.1% formic acid. Gradient elution conditions included that the A phase increased from 30% to 100% and the B phase decreased from 70% to 0 within 0-35 min. The flow rate was 0.2 ml/min and the loading amount was 8 μl. Mass spectrum conditions: Negative ion scanning was used and the scanning range (m/z) was 100-1500.

The results were shown in FIG. 6. FIG. 6B shows the detection results of kaurenoic acid, in which the results obtained from high resolution mass spectrum show that there is the 303.2291 ion by positive ion scanning FIG. 6C shows the detection results of steviol, in which the results obtained from high resolution mass spectrum show that there is the 319.2244 ion by positive ion scanning FIG. 6D shows the detection results of steviolmonoside, in which the results obtained from high resolution mass spectrum show that there is the 481.2754 ion by positive ion scanning FIG. 6E shows the detection results of rebaudioside A, in which the results obtained from high resolution mass spectrum show that there is the 967.43 ion by positive ion scanning. The results could demonstrate that the recombinant *E. coli* could successfully synthesize kaurenoic acid, steviol, steviolmonoside and rebaudioside A. The yield of rebaudioside A produced by cells transformed by various vectors are shown in FIG. 6F and Table 7.

TABLE 7

| Sample | $OD_{600}$ | Yield of rebaudioside A (mg/L) |
|---|---|---|
| BL21 (DE3) (pET28a + pJF47) (Control, blank plasmid) | 23.9 | 0 |
| BL21 (DE3) (pZQ9 + pJF47) | 25.6 | 1.8 |
| BL21 (DE3) (pZQ110 + pJF47) | 20.2 | 11 |
| BL21 (DE3) (pZQ120 + pJF47) | 22.3 | 8.4 |
| BL21 (DE3) (pZQ111 + pJF47) | 21 | 4.0 |
| BL21 (DE3) (pZQ121 + pJF47) | 21.2 | 3.0 |
| BL21 (DE3) (pZQ112 + pJF47) | 22.5 | 2 |

From the synthesis pathway of rebaudioside A, it can be found that the UGTB1 glycosyltransferases from *Starmerella bombicola* could successfully further glycosylated the C-2' site at the C-13 glucose of steviolmonoside to produce steviolbioside. By comparing the yield of rebaudioside A, it can be found that proteins from different sources could influence the yield. The highest yield was produced by pZQ110, which could reach to 11 mg/L. In the pZQ110, GGPPS was from *Taxus canadensis*, CPS/KS was from *Physcomitrella patens*, KO and KAH were from *Stevia rebaudiana*, CPR was from *Phaeosphaeria*, UGT76G1, UGT74G1 and UGT85C2 were from *Stevia rebaudiana*, and UGTB1 glycosyltransferase was from *Starmerella bombicola*.

Example 8

Transformation of Fungal Vector and Expression in Yeast

The expression plasmids obtained in Example 3 for synthesizing rebaudioside A was digested by SalI to produce a linearized vector. The linearized vector was transformed by electroporation into *Pichia pastoris* KM71 (purchased from Invitrogen) to produce recombinant *Pichia pastoris* KM71 having plasmids integrated into the genome at the His site. Clone was picked up to BMGY liquid culture medium and cultured at 30° C. for 24 hours. The cells were collected by centrifugation and 10% (v/v) glycerol was added to prepare an inoculum. The inoculum was stored at −80° C.

Clone was picked up to 50 ml BMGY in 500 ml shake flask and subjected to 28° C. overnight. The culture was cultured at 250 rpm until $OD_{600}$ reached 2-5 (about 16-20 hours). The cells were collected by centrifugation and the supernate was discarded. The cells were inoculated to 10 ml BMMY in 100 ml shake flask and then cultured at 28° C. and 250 rpm. 50 μl methanol was added every 24 hours. After culturing 5 days, the fermentation broth was collected and stored at −80° C.

Example 9

Detection of Ent-Kaurene in Some Recombinant Cells for Synthesizing Ent-Kaurene, an Intermediate for *Stevia* Sugar, Prepared in Example 8

The product, ent-kaurene, produced by fermenting the recombinant *Pichia pastoris* KM71 obtained in Example 8 was detected.

Figure 7:
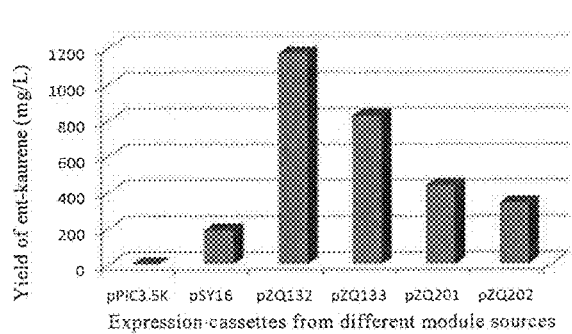
FIG. 7 shows the yield of ent-kaurene from the fermentation broth of Example 9.

50 μl 2M HCl were added into 1 ml fermentation broth of Example 8 and then the same volume of ethyl acetate were added. The mixture was subjected to ultrasonic treatment in an ice bath for 1 min and then vortexed at ambient temperature for 20 min. After that, the mixture was centrifuged at 12000 rpm for 1 min to separate the organic phase. The organic phase was sucked out and the residual water phase was extracted by the same volume of ethyl acetate for one time. The organic phases were pooled. The ent-kaurene was detected by GC-MS. The ent-kaurene was successfully detected and its yield was shown in FIG. 7 and Table 8.

TABLE 8

| Sample | $OD_{600}$ Value | Yield of ent-Kaurene (mg/L) |
|---|---|---|
| KM71 (pPIC3.5K) (Control, blank control) | 24.7 | 0 |
| KM71 (pSY16) | 124 | 189 |
| KM71 (pZQ132) | 143 | 1172 |
| KM71 (pZQ133) | 135 | 827 |
| KM71 (pZQ201) | 120 | 438 |
| KM71 (pZQ202) | 123 | 342 |

According to the data on the yield, in the *Pichia pastoris* expression system, the bifunctional CPS/KS combination was superior in synthesizing ent-kaurene than the CDPS/KS combination. With the most preferred expression vector pZQ132, the yield of ent-kaurene could reach 1172 mg/L, which was 5.4 folds higher than the yield obtained by the pSY16 expression vector.

Example 10

Detection of Product Produced by Some Recombinant Yeast Cells for Synthesizing Rebaudioside A Prepared in Example 8

One milliliter ethyl acetate was added into 1 ml fermentation broth of Example 8. The mixture was subjected to ultrasonic treatment in an ice bath for 1 min and then vortexed at ambient temperature for 20 min. After that, the mixture was centrifuged at 12000 rpm for 1 min to separate the organic phase. The organic phase was sucked out and the residual water phase was extracted by the same volume of ethyl acetate for one time. The organic phases were pooled and extracted to obtain the steviol glycosides, including kaurenoic acid, steviol, steviolmonoside and rebaudioside A. The organic phase was dried under vacuum. 500 µl acetonitrile were added to re-dissolve the residues and the product was detected by HPLC-MS. The results of high resolution mass spectrum obtained by positive ion scanning show that there are 303.2291, 319.2244, 481.2754 and 967.43 ions, indicating that kaurenoic acid, steviol, steviolmonoside and rebaudioside A were successfully synthesized in the recombinant *Pichia pastoris*. The yields of rebaudioside A of each recombinant yeast cells were shown in FIG. 8 and Table 9.

TABLE 9

| Sample | $OD_{600}$ | Yield of rebaudioside A (mg/L) |
| --- | --- | --- |
| KM71 (pPIC3.5K) (Control, blank plasmid) | 24.7 | 0 |
| KM71 (pSY22) | 120 | 1.7 |
| KM71 (pZQ210) | 132 | 12 |
| KM71 (pZQ220) | 141 | 8.9 |
| KM71 (pZQ211) | 118 | 4.5 |
| KM71 (pZQ221) | 119 | 3.6 |

Figure 8:
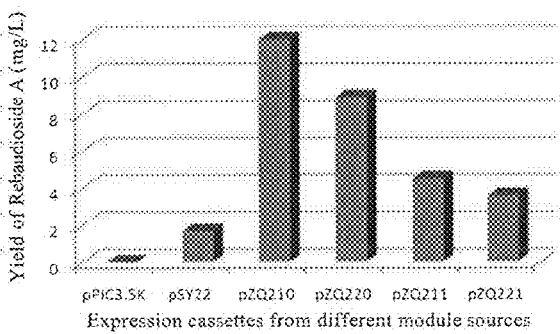
FIG. 8 shows the yield of rebaudioside A obtained from the fermentation broth of Example 10.

According to FIG. 8 and Table 9, the highest yield of rebaudioside A was obtained by pZQ210, which reached 12 mg/L. In pZQ210, GGPP was from *Taxus canadensis*, CPS/KS was from *Physcomitrella patens*, KO and KAH were from *Stevia rebaudiana*, CPR was from *Phaeosphaeria*, UGT76G1, UGT74G1 and UGT85C2 were from *Stevia rebaudiana*, and UGTB1 glycosyltransferase was from *Starmerella bombicola*.

Example 11

Study on Function of UGTB1 or IBGT Glycosyltransferase

Figure 9:
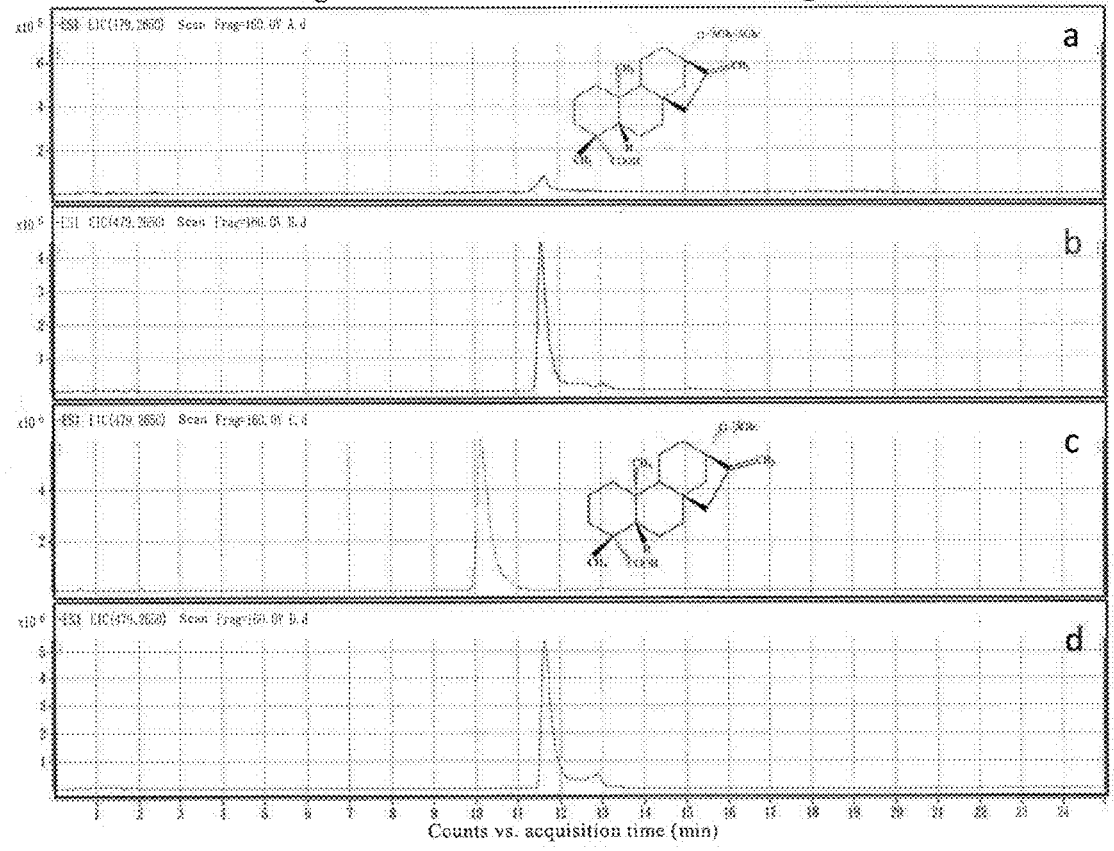
FIG. 9 shows the HPLC-MS maps of steviolmonoside and steviolbioside obtained from the fermentation broth of Example 11.
9a shows the HPLC-MS maps of steviolmonoside and steviolbioside obtained from fermentation broth of the engineering strain containing the pZQ107 expression vector;
9b shows the HPLC-MS maps of steviolmonoside and steviolbioside obtained from fermentation broth of the engineering strain containing the pZQ108 expression vector;
9c shows the HPLC-MS maps of steviolmonoside and steviolbioside obtained from fermentation broth of the engineering strain containing the pZQ105 expression vector;
9d shows the HPLC-MS maps of steviolmonoside and steviolbioside obtained from fermentation broth of the engineering strain containing the pZQ109 expression vector.

One milliliter ethyl acetate was added into 1 ml fermentation broth of Example 5. The mixture was subjected to ultrasonic treatment in an ice bath for 1 min and then vortexed at ambient temperature for 20 min. After that, the mixture was centrifuged at 12000 rpm for 1 min to separate the organic phase. The organic phase was sucked out and the residual water phase was extracted by the same volume of ethyl acetate for one time. The organic phases were pooled and extracted to obtain steviolmonoside and steviolbioside. The organic phase was dried under vacuum. 500 µl acetonitrile were added to re-dissolve the residues and the product was detected by HPLC-MS. The results were shown in FIG. 9. According to FIG. 9C, the fermentation broth of pZQ104, pZQ105 or pZQ106 which only contains UGT85c2 glycosyltransferase but does not contain UGTB1 glycosyltransferase or IBGT glycosyltransferase only contained steviolmonoside. No steviolbioside was detected in these broths. The pZQ107, pZQ108, pZQ109, pSY200, pSY201 and pSY202 contain both UGT85c2 glycosyltransferase and UGTB1 glycosyltransferase or IBGT glycosyltransferase. Steviolbioside was successfully detected in their fermentation broths (FIGS. 9A, 9B and 9D).

The inventors have also detected the yields of steviolmonoside and steviolbioside produced by prokaryotic cells transformed by different expression vectors. The results were shown in FIG. 10 and Table 10.

TABLE 10

| Sample | $OD_{600}$ | Yield of steviolmonoside (mg/L) | Yield of steviolbioside (mg/L) |
| --- | --- | --- | --- |
| BL21(DE3) (pET28a + pJF47) (Control, blank plasmid) | 23.0 | 0 | 0 |
| BL21(DE3) (pZQ104 + pJF47) | 24.9 | 24 | 0 |
| BL21(DE3) (pZQ105 + pJF47) | 20.6 | 150 | 0 |
| BL21(DE3) (pZQ106 + pJF47) | 22.1 | 98 | 0 |
| BL21(DE3) (pZQ107 + pJF47) | 21.3 | 0.08 | 33 |
| BL21(DE3) (pZQ108 + pJF47) | 21.9 | 1.3 | 206 |
| BL21(DE3) (pZQ109 + pJF47) | 22.7 | 0.7 | 134 |
| BL21(DE3) (pSY200 + pJF47) | 21.1 | 0.09 | 31 |
| BL21(DE3) (pSY200 + pJF47) | 21.3 | 1.2 | 215 |
| BL21(DE3) (pSY200 + pJF47) | 22.8 | 0.6 | 140 |

Figure 10:
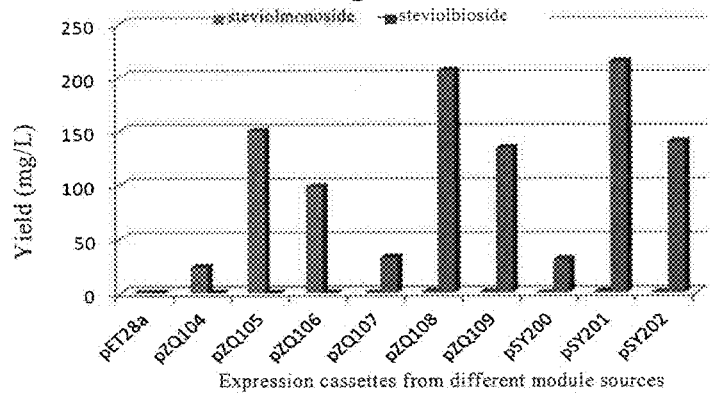
FIG. 10 shows the yields of steviolmonoside and steviolbioside obtained after transfecting the cells with expression plasmids from different sources, as shown in Example 11.

According to FIG. 10 and Table 10, the expression vectors pZQ104, pZQ105 and pZQ106 that do not contain UGTB1 glycosyltransferase or IBGT glycosyltransferase and the negative pET28a could only produce steviolmonoside but did not produce steviolbioside. From the biocatalytic efficiency, UGTB1 glycosyltransferase or IBGT glycosyltransferase could produce very high conversion efficiency when catalyzing steviolmonoside, which could reach up to 99%.

All literature references cited herein are hereby incorporated by reference, just as each reference was cited independently. Moreover, it should be understood that the skilled in the art can change or modify the present invention based on the above disclosure and the equivalent arrangements are also included in the scope of the claims attached in the application.

The invention claimed is:

1. A method for synthesizing a steviol glycoside with an additional glucose unit, the method comprising:
providing an isolated recombinant host cell transformed with an expression construct encoding a glycosyltransferase polypeptide comprising the amino acid sequence of SEQ ID NO: 41 or 51, and wherein said host cell comprises a steviol glycoside with an O-glucose residue;
allowing the glycosyltransferase to catalyze transfer of glucose to the O-glucose residue of the steviol glycoside to produce a steviol glycoside with an additional glucose unit; and
isolating the steviol glycoside with the additional glucose unit.

2. The method according to claim 1, wherein catalytic substrates of the glycosyltransferase include steviolmonoside, rubusoside, stevioside, or rebaudioside A.

3. The method according to claim 2, wherein the glycosyltransferase catalyzes production of steviolbioside from steviolmonoside.

4. The method according to claim 1, wherein the host cell further comprises one or more of the following enzymes:
Geranylgeranyl diphosphate synthase;
Bifunctional ent-kaurene synthase, or a combination of ent-copalyl diphosphate synthase and ent-kaurene synthase;
Ent-kaurene oxidase;
Cytochrome P450 redox protein;
Kaurenoic acid-13α-hydroxylase;
UGT85C2 glycosyltransferase;
UGT74G1 glycosyltransferase; or
UGT76G1 glycosyltransferase.

5. The method according to claim 1, wherein the host cell further comprises one or more genes encoding: 1-deoxy-D-xylulose-5-phosphate synthase, 2-C-methyl-D-erythritol 4-phosphate cytidylyltransferase, 2-C-methyl-D-erythritol 2,4-cyclodiphosphate synthase, or isopentenyl-diphosphate delta-isomerase.

6. The method according to claim 1, wherein the host cell is a prokaryotic cell.

7. The method according to claim 6, wherein the prokaryotic cell is *Escherichia coli, Bacillus subtilis, Acetobacteria, Corynebacterium* or *Brevibacterium*.

8. The method according to claim 7, wherein the *E. coli* is BL21, BLR, DH10B, HMS, C43, JM109, DH5α, or Noveblue.

9. The method according to claim 1, wherein the host cell is a eukaryotic cell.

10. The method according to claim 9, wherein the eukaryotic cell is yeast, mold, or basidiomycete.

11. The method according to claim 10, wherein the yeast is *Pichia pastoris, Saccharomyces cerevisiae*, or *Kluyveromyces lactis*.

12. The method according to claim 11, wherein the *Pichia pastoris* is GS115, MC100-3, SMD1163, SMD1165, SMD1168, or KM71.

13. The method according to claim 11, wherein the *Saccharomyces cerevisiae* is W303, CEN.PK2, S288c, FY834, or S1949.

14. The method according to claim 11, wherein the *Kluyveromyces lactis* is GG799.

* * * * *

SEQUENCE LISTING

<160> NUMBER OF SEQ ID NOS: 68

<210> SEQ ID NO 1
<211> LENGTH: 296
<212> TYPE: PRT
<213> ORGANISM: Taxus canadensis

<400> SEQUENCE: 1

Met Phe Asp Phe Asn Glu Tyr Met Lys Ser Lys Ala Val Ala Val Asp
1               5                   10                  15

Ala Ala Leu Asp Lys Ala Ile Pro Leu Glu Tyr Pro Glu Lys Ile His
            20                  25                  30

Glu Ser Met Arg Tyr Ser Leu Leu Ala Gly Gly Lys Arg Val Arg Pro
        35                  40                  45

```
Ala Leu Cys Ile Ala Ala Cys Glu Leu Val Gly Gly Ser Gln Asp Leu
     50                  55                  60

Ala Met Pro Thr Ala Cys Ala Met Glu Met Ile His Thr Met Ser Leu
 65                  70                  75                  80

Ile His Asp Asp Leu Pro Cys Met Asp Asn Asp Asp Phe Arg Arg Gly
                 85                  90                  95

Lys Pro Thr Asn His Lys Val Phe Gly Glu Asp Thr Ala Val Leu Ala
                100                 105                 110

Gly Asp Ala Leu Leu Ser Phe Ala Phe Glu His Ile Ala Val Ala Thr
                115                 120                 125

Ser Lys Thr Val Pro Ser Asp Arg Thr Leu Arg Val Ile Ser Glu Leu
    130                 135                 140

Gly Lys Thr Ile Gly Ser Gln Gly Leu Val Gly Gln Val Val Asp
145                 150                 155                 160

Ile Thr Ser Glu Gly Asp Ala Asn Val Asp Leu Lys Thr Leu Glu Trp
                165                 170                 175

Ile His Ile His Lys Thr Ala Val Leu Leu Glu Cys Ser Val Val Ser
                180                 185                 190

Gly Gly Ile Leu Gly Gly Ala Thr Glu Asp Glu Ile Ala Arg Ile Arg
    195                 200                 205

Arg Tyr Ala Arg Cys Val Gly Leu Leu Phe Gln Val Val Asp Asp Ile
    210                 215                 220

Leu Asp Val Thr Lys Ser Ser Glu Glu Leu Gly Lys Thr Ala Gly Lys
225                 230                 235                 240

Asp Leu Leu Thr Asp Lys Ala Thr Tyr Pro Lys Leu Met Gly Leu Glu
                245                 250                 255

Lys Ala Lys Glu Phe Ala Ala Glu Leu Ala Thr Arg Ala Lys Glu Glu
                260                 265                 270

Leu Ser Ser Phe Asp Gln Ile Lys Ala Ala Pro Leu Leu Gly Leu Ala
                275                 280                 285

Asp Tyr Ile Ala Phe Arg Gln Asn
    290                 295

<210> SEQ ID NO 2
<211> LENGTH: 891
<212> TYPE: DNA
<213> ORGANISM: Taxus canadensis

<400> SEQUENCE: 2
atgtttgatt tcaatgaata tatgaaaagt aaggctgttg cggtagacgc ggctctggat      60
aaagcgattc cgctggaata tcccgagaag attcacgaat cgatgcgcta ctccctgtta     120
gcaggaggga aacgcgttcg tccggcatta tgcatcgcgg cctgtgaact cgtcggcggt     180
tcacaggact agcaatgcc aactgcttgc gcaatggaaa tgattcacac aatgagcctg     240
attcatgatg atttgccttg catggacaac gatgactttc ggcgcggtaa acctactaat     300
cataaggttt ttggcgaaga tactgcagtg ctggcgggcg atgcgctgct gtcgtttgcc     360
ttcgaacata tcgccgtcgc gacctcgaaa accgtcccgt cggaccgtac gcttcgcgtg     420
atttccgagc tgggaaagac catcggctct caaggactcg tggtggtca ggtagttgat     480 atcacgtctg agggtgacgc gaacgtggac ctgaaaaccc tggagtggat ccatattcac     540
aaaacggccg tgctgctgga atgtagcgtg gtgtcagggg ggatcttggg gggcgccacg     600
gaggatgaaa tcgcgcgtat tcgtcgttat gcccgctgtg ttggactgtt atttcaggtg     660
gtggatgaca tcctggatgt cacaaaatcc agcgaagagc ttggcaagac cgcgggcaaa     720
```

-continued

```
gaccttctga cggataaggc tacataccccg aaattgatgg gcttggagaa agccaaggag    780
ttcgcagctg aacttgccac gcgggcgaag gaagaactct cttctttcga tcaaatcaaa    840
gccgcgccac tgctgggcct cgccgattac attgcgtttc gtcagaacta a             891

<210> SEQ ID NO 3
<211> LENGTH: 787
<212> TYPE: PRT
<213> ORGANISM: Stevia rebaudiana

<400> SEQUENCE: 3

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
            180                 185                 190

Lys Leu Glu Asp Glu Asn Ala Glu His Met Pro Ile Gly Phe Glu Val
        195                 200                 205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
        275                 280                 285

Thr Ala Phe Ala Leu Met Gln Thr Lys Asp Glu Lys Cys Leu Gln Tyr
    290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Val Asp Arg Leu Gln Arg
                325                 330                 335

Leu Gly Ile Ala Arg Tyr Phe Lys Ser Glu Ile Lys Asp Cys Val Glu
            340                 345                 350
```

```
Tyr Ile Asn Lys Tyr Trp Thr Lys Asn Gly Ile Cys Trp Ala Arg Asn
            355                 360                 365
Thr His Val Gln Asp Ile Asp Asp Thr Ala Met Gly Phe Arg Val Leu
        370                 375                 380
Arg Ala His Gly Tyr Asp Val Thr Pro Asp Val Phe Arg Gln Phe Glu
385                 390                 395                 400
Lys Asp Gly Lys Phe Val Cys Phe Ala Gly Gln Ser Thr Gln Ala Val
                405                 410                 415
Thr Gly Met Phe Asn Val Tyr Arg Ala Ser Gln Met Leu Phe Pro Gly
            420                 425                 430
Glu Arg Ile Leu Glu Asp Ala Lys Lys Phe Ser Tyr Asn Tyr Leu Lys
                435                 440                 445
Glu Lys Gln Ser Thr Asn Glu Leu Leu Asp Lys Trp Ile Ile Ala Lys
        450                 455                 460
Asp Leu Pro Gly Glu Val Gly Tyr Ala Leu Asp Ile Pro Trp Tyr Ala
465                 470                 475                 480
Ser Leu Pro Arg Leu Glu Thr Arg Tyr Tyr Leu Glu Gln Tyr Gly Gly
                485                 490                 495
Glu Asp Asp Val Trp Ile Gly Lys Thr Leu Tyr Arg Met Gly Tyr Val
            500                 505                 510
Ser Asn Asn Thr Tyr Leu Glu Met Ala Lys Leu Asp Tyr Asn Asn Tyr
                515                 520                 525
Val Ala Val Leu Gln Leu Glu Trp Tyr Thr Ile Gln Gln Trp Tyr Val
        530                 535                 540
Asp Ile Gly Ile Glu Lys Phe Glu Ser Asp Asn Ile Lys Ser Val Leu
545                 550                 555                 560
Val Ser Tyr Tyr Leu Ala Ala Ser Ile Phe Glu Pro Glu Arg Ser
                565                 570                 575
Lys Glu Arg Ile Ala Trp Ala Lys Thr Thr Ile Leu Val Asp Lys Ile
            580                 585                 590
Thr Ser Ile Phe Asp Ser Ser Gln Ser Ser Lys Glu Asp Ile Thr Ala
        595                 600                 605
Phe Ile Asp Lys Phe Arg Asn Lys Ser Ser Ser Lys Lys His Ser Ile
610                 615                 620
Asn Gly Glu Pro Trp His Glu Val Met Val Ala Leu Lys Lys Thr Leu
625                 630                 635                 640
His Gly Phe Ala Leu Asp Ala Leu Met Thr His Ser Gln Asp Ile His
                645                 650                 655
Pro Gln Leu His Gln Ala Trp Glu Met Trp Leu Thr Lys Leu Gln Asp
            660                 665                 670
Gly Val Asp Val Thr Ala Glu Leu Met Val Gln Met Ile Asn Met Thr
        675                 680                 685
Ala Gly Arg Trp Val Ser Lys Glu Leu Leu Thr His Pro Gln Tyr Gln
        690                 695                 700
Arg Leu Ser Thr Val Thr Asn Ser Val Cys His Asp Ile Thr Lys Leu
705                 710                 715                 720
His Asn Phe Lys Glu Asn Ser Thr Thr Val Asp Ser Lys Val Gln Glu
                725                 730                 735
Leu Val Gln Leu Val Phe Ser Asp Thr Pro Asp Asp Leu Asp Gln Asp
            740                 745                 750
Met Lys Gln Thr Phe Leu Thr Val Met Lys Thr Phe Tyr Tyr Lys Ala
        755                 760                 765
```

Trp Cys Asp Pro Asn Thr Ile Asn Asp His Ile Ser Lys Val Phe Glu
          770                 775                 780

Ile Val Ile
785

<210> SEQ ID NO 4
<211> LENGTH: 2364
<212> TYPE: DNA
<213> ORGANISM: Stevia rebaudiana

<400> SEQUENCE: 4

| | | | | | |
|---|---|---|---|---|---|
| atgaaaaccg | gtttcatctc | tccggcgacc | gttttccacc | accgtatctc | tccggcgacc | 60 |
| accttccgtc | accacctgtc | tccggcgacc | accaactcta | ccgtatcgt | tgcgctgcgt | 120 |
| gacatcaact | tccgttgcaa | agcggtttct | aaagaatact | ctgacctgct | gcagaaagac | 180 |
| gaagcgtctt | tcaccaaatg | gacgacgac | aaagttaaag | accacctgga | caccaacaaa | 240 |
| aacctgtacc | cgaacgacga | atcaaagaa | ttcgttgaat | ctgttaaagc | gatgttcggt | 300 |
| tctatgaacg | acggtgaaat | caacgtttct | gcgtacgaca | ccgcgtgggt | tgcgctggtt | 360 |
| caggacgttg | acggttctgg | ttctccgcag | ttcccgtctt | ctctggaatg | gatcgcgaac | 420 |
| aaccagctgt | ctgacggttc | ttggggtgac | cacctgctgt | ctctgcgca | cgaccgtatc | 480 |
| atcaacaccc | tggcgtgcgt | tatcgcgctg | acctcttgga | acgttcaccc | gtctaaatgc | 540 |
| gaaaaaggtc | tgaacttcct | gcgtgaaaac | atctgcaaac | tggaagacga | aaacgcggaa | 600 |
| cacatgccga | tcggttcga | agttaccttc | ccgtctctga | tcgacatcgc | gaaaaaactg | 660 |
| aacatcgaag | ttccggaaga | cacccggcg | ctgaaagaaa | tctacgcgcg | tcgtgacatc | 720 |
| aaactgacca | aaatcccgat | ggaagttctg | cacaaagttc | cgaccaccct | gctgcactct | 780 |
| ctggaaggta | tgccggacct | ggaatgggaa | aaactgctga | actgcagtg | caaagacggt | 840 |
| tctttcctgt | ctctccgtc | ttctaccgcg | ttcgcgctga | tgcagaccaa | agacgaaaaa | 900 |
| tgcctgcagt | acctgaccaa | catcgttacc | aaattcaacg | tggtgttcc | gaacgtttac | 960 |
| ccggttgacc | tgttcgaaca | catctgggtt | gttgaccgtc | tgcagcgtct | gggtatcgcg | 1020 |
| cgttacttca | atctgaaat | caaagactgc | gttaataca | tcaacaaata | ctggaccaaa | 1080 |
| aacggtatct | gctgggcgcg | taacacccac | gttcaggaca | tcgacgacac | cgcgatgggt | 1140 |
| ttccgtgttc | tgcgtgcgca | cggttacgac | gttacccccgg | acgttttccg | tcagttcgaa | 1200 |
| aaagacggta | aattcgtttg | cttcgcgggt | cagtctaccc | aggcggttac | cggtatgttc | 1260 |
| aacgtttacc | gtgcgtctca | gatgctgttc | ccgggtgaac | gtatcctgga | agacgcgaaa | 1320 |
| aaattctctt | acaactacct | gaaagaaaaa | cagtctacca | cgaactgct | ggacaaatgg | 1380 |
| atcatcgcga | agacctgcc | gggtgaagtt | ggttacgcgc | tggacatccc | gtggtacgcg | 1440 |
| tctctgccgc | gtctggaaac | ccgttactac | ctggaacagt | acggtggtga | agacgacgtt | 1500 |
| tggatcggta | aaaccctgta | ccgtatgggt | tacgtttcta | caacaccta | cctgaaatg | 1560 |
| gcgaaactgg | actacaacaa | ctacgttgcg | gttctgcagc | tggaatggta | caccatccag | 1620 |
| cagtggtacg | ttgacatcgg | tatcgaaaaa | ttcgaatctg | acaacatcaa | atctgttctg | 1680 |
| gtttcttact | acctggcggc | ggcgtctatc | ttcgaaccgg | aacgttctaa | agaacgtatc | 1740 |
| gcgtgggcga | aaaccaccat | cctggttgac | aaaatcacct | ctatcttcga | ctcttctcag | 1800 |
| tcttctaaag | aagacatcac | cgcgttcatc | gacaaattcc | gtaacaaatc | ttcttctaaa | 1860 |
| aaacactcta | tcaacggtga | accgtggcac | gaagttatgg | ttgcgctgaa | aaaaccctg | 1920 |
| cacggtttcg | cgctggacgc | gctgatgacc | cactctcagg | acatccaccc | gcagctgcac | 1980 |

-continued

```
caggcgtggg aaatgtggct gaccaaactg caggacggtg ttgacgttac cgcggaactg    2040
atggttcaga tgatcaacat gaccgcgggt cgttgggttt ctaaagaact gctgacccac    2100
ccgcagtacc agcgtctgtc taccgttacc aactctgttt gccacgacat caccaaactg    2160
cacaacttca agaaaactc taccaccgtt gactctaaag ttcaggaact ggttcagctg    2220
gttttctctg acaccccgga cgacctggac caggacatga aacagacctt cctgaccgtt    2280
atgaaaacct tctactacaa agcgtggtgc gacccgaaca ccatcaacga ccacatctct    2340
aaagttttcg aaatcgttat ctaa                                          2364
```

```
<210> SEQ ID NO 5
<211> LENGTH: 784
<212> TYPE: PRT
<213> ORGANISM: Stevia rebaudiana

<400> SEQUENCE: 5
```

| Met | Asn | Leu | Ser | Leu | Cys | Ile | Ala | Ser | Pro | Leu | Leu | Thr | Lys | Ser | Ser |
|---|---|---|---|---|---|---|---|---|---|---|---|---|---|---|---|
| 1 | | | | 5 | | | | | 10 | | | | | 15 | |

| Arg | Pro | Thr | Ala | Leu | Ser | Ala | Ile | His | Thr | Ala | Ser | Thr | Ser | His | Gly |
| | | | 20 | | | | | 25 | | | | | 30 | | |

| Gly | Gln | Thr | Asn | Pro | Thr | Asn | Leu | Ile | Ile | Asp | Thr | Thr | Lys | Glu | Arg |
| | | 35 | | | | | 40 | | | | | 45 | | | |

| Ile | Gln | Lys | Leu | Phe | Lys | Asn | Val | Glu | Ile | Ser | Val | Ser | Ser | Tyr | Asp |
| | 50 | | | | | 55 | | | | | 60 | | | | |

| Thr | Ala | Trp | Val | Ala | Met | Val | Pro | Ser | Pro | Asn | Ser | Pro | Lys | Ser | Pro |
| 65 | | | | | 70 | | | | | 75 | | | | | 80 |

| Cys | Phe | Pro | Glu | Cys | Leu | Asn | Trp | Leu | Ile | Asn | Asn | Gln | Leu | Asn | Asp |
| | | | | 85 | | | | | 90 | | | | | 95 | |

| Gly | Ser | Trp | Gly | Leu | Val | Asn | His | Thr | His | Asn | His | Asn | His | Pro | Leu |
| | | | | 100 | | | | | 105 | | | | | 110 | |

| Leu | Lys | Asp | Ser | Leu | Ser | Ser | Thr | Leu | Ala | Cys | Ile | Val | Ala | Leu | Lys |
| | | | 115 | | | | | 120 | | | | | 125 | | |

| Arg | Trp | Asn | Val | Gly | Glu | Asp | Gln | Ile | Asn | Lys | Gly | Leu | Ser | Phe | Ile |
| | 130 | | | | | 135 | | | | | 140 | | | | |

| Glu | Ser | Asn | Leu | Ala | Ser | Ala | Thr | Asp | Lys | Ser | Gln | Pro | Ser | Pro | Ile |
| 145 | | | | | 150 | | | | | 155 | | | | | 160 |

| Gly | Phe | Asp | Ile | Ile | Phe | Pro | Gly | Leu | Leu | Glu | Tyr | Ala | Lys | Asn | Leu |
| | | | | 165 | | | | | 170 | | | | | 175 | |

| Asp | Ile | Asn | Leu | Leu | Ser | Lys | Gln | Thr | Asp | Phe | Ser | Leu | Met | Leu | His |
| | | | 180 | | | | | 185 | | | | | 190 | | |

| Lys | Arg | Glu | Leu | Glu | Gln | Lys | Arg | Cys | His | Ser | Asn | Glu | Ile | Asp | Gly |
| | | 195 | | | | | 200 | | | | | 205 | | | |

| Tyr | Leu | Ala | Tyr | Ile | Ser | Glu | Gly | Leu | Gly | Asn | Leu | Tyr | Asp | Trp | Asn |
| | 210 | | | | | 215 | | | | | 220 | | | | |

| Met | Val | Lys | Lys | Tyr | Gln | Met | Lys | Asn | Gly | Ser | Val | Phe | Asn | Ser | Pro |
| 225 | | | | | 230 | | | | | 235 | | | | | 240 |

| Ser | Ala | Thr | Ala | Ala | Ala | Phe | Ile | Asn | His | Gln | Asn | Pro | Gly | Cys | Leu |
| | | | | 245 | | | | | 250 | | | | | 255 | |

| Asn | Tyr | Leu | Asn | Ser | Leu | Leu | Asp | Lys | Phe | Gly | Asn | Ala | Val | Pro | Thr |
| | | | 260 | | | | | 265 | | | | | 270 | | |

| Val | Tyr | Pro | Leu | Asp | Leu | Tyr | Ile | Arg | Leu | Ser | Met | Val | Asp | Thr | Ile |
| | | 275 | | | | | 280 | | | | | 285 | | | |

| Glu | Arg | Leu | Gly | Ile | Ser | His | His | Phe | Arg | Val | Glu | Ile | Lys | Asn | Val |
| | 290 | | | | | 295 | | | | | 300 | | | | |

```
Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Tyr Leu Arg Leu Ala Val Glu Asp Phe Tyr Thr Cys
    450                 455                 460

Gln Ser Ile Tyr Arg Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu
705                 710                 715                 720
```

```
Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
        755                 760                 765

Ile Ile Tyr Asn Pro Leu Val Leu Val Asn Glu Asn Glu Glu Gln Arg
    770                 775                 780

<210> SEQ ID NO 6
<211> LENGTH: 2355
<212> TYPE: DNA
<213> ORGANISM: Stevia rebaudiana

<400> SEQUENCE: 6
atgaacctgt ctctgtgcat cgcgtctccg ctgctgacca atcttctcg tccgaccgcg      60 ctgtctgcga tccacaccgc gtctacctct cacggtggtc agaccaaccc gaccaacctg     120
atcatcgaca ccaccaaaga acgtatccag aaactgttca aaaacgttga atctctgtt     180 tcttcttacg acaccgcgtg ggttgcgatg gttccgtctc cgaactctcc gaaatctccg     240
tgcttcccgg aatgcctgaa ctggctgatc aacaaccagc tgaacgacgg ttcttggggt     300
ctggttaacc acaccacaa ccacaaccac cgctgctga agactctct gtcttctacc      360 ctggcgtgca tcgttgcgct gaaacgttgg aacgttggtg aagaccagat caacaaaggt     420
ctgtctttca tcgaatctaa cctggcgtct gcgaccgaca atctcagcc gtctccgatc     480 ggtttcgaca tcatcttccc gggtctgctg aatacgcga aaaacctgga catcaacctg     540
ctgtctaaac agaccgactt ctctctgatg ctgcacaaac gtgaactgga acagaaacgt     600
tgccactcta cgaaatcga cggttacctg gcgtacatct tgaaggtct gggtaacctg      660 tacgactgga acatggttaa aaaataccag atgaaaaacg ttctgttttt caactctccg     720
tctgcgaccg cggcggcgtt catcaaccac cagaacccgg ttgcctgaa ctacctgaac      780 tctctgctgg acaaattcgg taacgcggtt ccgaccgttt acccgctgga cctgtacatc     840
cgtctgtcta tggttgacac catcgaacgt ctgggtatct tcaccactt ccgtgttgaa      900 atcaaaaacg ttctggacga aacctaccgt tgctgggttg aacgtgacga acagatcttc     960
atggacgttg ttacctgcgc gctggcgttc cgtctgctgc gtatccacgg ttacaaagtt    1020
tctccggacc agctggcgga aatcaccaac gaactggcgt tcaaagacga atacgcggcg    1080
ctggaaacct accacgcgtc tcagatcctg taccaggaag acctgtcttc tggtaaacag    1140
atcctgaaat ctgcggactt cctgaaaggt atcctgtcta ccgactctaa ccgtctgtct    1200
aaactgatcc acaaagaagt tgaaaacgcg ctgaaattcc cgatcaacac cggtctggaa    1260
cgtatcaaca cccgtcgtaa catccagctg tacaacgttg acaacacccg tatcctgaaa    1320
accacctacc actcttctaa catctctaac acctactacc tgcgtctggc ggttgaagac    1380
ttctacacct gccagtctat ctaccgtgaa gaactgaaag tctggaacg ttgggttgtt     1440 cagaacaaac tggaccagct gaaattcgcg cgtcagaaaa ccgcgtactg ctacttctct    1500
gttgcggcga ccctgtcttc tccggaactg tctgacgcgc gtatctcttg ggcgaaaaac    1560
ggtatcctga ccaccgttgt tgacgacttc ttcgacatcg gtggtaccat cgacgaactg    1620
accaacctga tccagtgcgt tgaaaaatgg aacgttgacg ttgacaaaga ctgctgctct    1680
gaacacgttc gtatcctgtt cctggcgctg aaagacgcga tctgctggat cggtgacgaa    1740
gcgttcaaat ggcaggcgcg tgacgttacc tctcacgtta tccagacctg gctggaactg    1800
```

-continued

```
atgaactcta tgctgcgtga agcgatctgg acccgtgacg cgtacgttcc gaccctgaac  1860
gaatacatgg aaaacgcgta cgtttctttc gcgctgggtc cgatcgttaa accggcgatc  1920
tacttcgttg gtccgaaact gtctgaagaa atcgttgaat cttctgaata ccacaacctg  1980
ttcaaactga tgtctaccca gggtcgtctg ctgaacgaca tccactcttt caaacgtgaa  2040
ttcaaagaag gtaaactgaa cgcggttgcg ctgcacctgt ctaacggtga atctggtaaa  2100
gttgaagaag aagttgttga gaaatgatg atgatgatca aaacaaacg taaagaactg  2160
atgaaactga tcttcgaaga aaacggttct atcgttccgc gtgcgtgcaa agacgcgttc  2220
tggaacatgt gccacgttct gaacttcttc tacgcgaacg acgacggttt caccggtaac  2280
accatcctgg acaccgttaa agacatcatc tacaacccgc tggttctggt taacgaaaac  2340
gaagaacagc gttaa                                                   2355
```

<210> SEQ ID NO 7
<211> LENGTH: 513
<212> TYPE: PRT
<213> ORGANISM: Stevia rebaudiana

<400> SEQUENCE: 7

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270
```

```
Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile

<210> SEQ ID NO 8
<211> LENGTH: 1548
<212> TYPE: DNA
<213> ORGANISM: Stevia rebaudiana

<400> SEQUENCE: 8
atggacgcgg ttaccggtct gctgaccgtt ccggcgaccg cgatcaccat cggtggtacc      60
gcggttgcgc tggcggttgc gctgatcttc tggtacctga atcttacac ctctgcgcgt     120 cgttctcagt ctaaccacct gccgcgtgtt ccggaagttc cgggtgttcc gctgctgggt     180
aacctgctgc agctgaaaga aaaaaaaccg tacatgacct cacccgttg gcggcgacc     240 tacggtccga tctactctat caaaaccggt gcgacctcta tggttgttgt ttcttctaac     300
gaaatcgcga agaagcgct ggttacccgt ttccagtcta tctctacccg taacctgtct     360
aaagcgctga agttctgac gcggacaaa accatggttg cgatgtctga ctacgacgac     420
taccacaaaa ccgttaaacg tcacatcctg accgcggttc tgggtccgaa cgcgcagaaa     480
aaacaccgta tccaccgtga catcatgatg acaacatct ctacccagct gcacgaattc     540
gttaaaaaca cccggaaca ggaagaagtt gacctgcgta aaatcttcca gtctgaactg     600
ttcggtctgg cgatgcgtca ggcgctgggt aaagacgttg aatctctgta cgttgaagac     660
ctgaaaatca ccatgaaccg tgacgaaatc ttccaggttc tggttgttga cccgatgatg     720
```

```
ggtgcgatcg acgttgactg gcgtgacttc ttcccgtacc tgaaatgggt tccgaacaaa    780
aaattcgaaa acaccatcca gcagatgtac atccgtcgtg aagcggttat gaaatctctg    840
atcaaagaac acaaaaaacg tatcgcgtct ggtgaaaaac tgaactctta catcgactac    900
ctgctgtctg aagcgcagac cctgaccgac cagcagctgc tgatgtctct gtgggaaccg    960
atcatcgaat cttctgacac caccatggtt accaccgaat gggcgatgta cgaactggcg   1020
aaaaacccga actgcagga ccgtctgtac cgtgacatca atctgtttg cggttctgaa    1080
aaaatcaccg aagaacacct gtctcagctg ccgtacatca ccgcgatctt ccacgaaacc   1140
ctgcgtcgtc actctccggt tccgatcatc ccgctgcgtc acgttcacga agacaccgtt   1200
ctgggtggtt accacgttcc ggcgggtacc gaactggcgg ttaacatcta cggttgcaac   1260
atggacaaaa acgtttggga aaacccggaa gaatggaacc cggaacgttt catgaaagaa   1320
aacgaaacca tcgacttcca gaaaaccatg gcgttcggtg gtggtaaacg tgtttgcgcg   1380
ggttctctgc aggcgctgct gaccgcgtct atcggtatcg gtcgtatggt tcaggaattc   1440
gaatggaaac tgaaagacat gacccaggaa gaagttaaca ccatcggtct gaccacccag   1500
atgctgcgtc cgctgcgtgc gatcatcaaa ccgcgtatca ctagttaa                1548
```

<210> SEQ ID NO 9
<211> LENGTH: 476
<212> TYPE: PRT
<213> ORGANISM: Stevia rebaudiana

<400> SEQUENCE: 9

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190

His Ile Ala Lys Leu Gly Ser Leu Phe Asn Ile Phe Leu Lys Gly Ile
        195                 200                 205

Ile Glu Leu Pro Ile Asp Val Pro Gly Thr Arg Phe Tyr Ser Ser Lys
    210                 215                 220
```

Lys Ala Ala Ala Ala Ile Arg Ile Glu Leu Lys Leu Ile Lys Ala
225                 230                 235                 240

Arg Lys Leu Glu Leu Lys Glu Gly Lys Ala Ser Ser Ser Gln Asp Leu
            245                 250                 255

Leu Ser His Leu Leu Thr Ser Pro Asp Glu Asn Gly Met Phe Leu Thr
        260                 265                 270

Glu Glu Glu Ile Val Asp Asn Ile Leu Leu Leu Phe Ala Gly His
    275                 280                 285

Asp Thr Ser Ala Leu Ser Ile Thr Leu Leu Met Lys Thr Leu Gly Glu
290                 295                 300

His Ser Asp Val Tyr Asp Lys Val Leu Lys Glu Gln Leu Glu Ile Ser
305                 310                 315                 320

Lys Thr Lys Glu Ala Trp Glu Ser Leu Lys Trp Glu Asp Ile Gln Lys
            325                 330                 335

Met Lys Tyr Ser Trp Ser Val Ile Cys Glu Val Met Arg Leu Asn Pro
        340                 345                 350

Pro Val Ile Gly Thr Tyr Arg Glu Ala Leu Val Asp Ile Asp Tyr Ala
    355                 360                 365

Gly Tyr Thr Ile Pro Lys Gly Trp Lys Leu His Trp Ser Ala Val Ser
370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
            405                 410                 415

Gly Gly Gly Pro Arg Met Cys Leu Gly Lys Glu Phe Ala Arg Leu Glu
        420                 425                 430

Val Leu Ala Phe Leu His Asn Ile Val Thr Asn Phe Lys Trp Asp Leu
    435                 440                 445

Leu Ile Pro Asp Glu Lys Ile Glu Tyr Asp Pro Met Ala Thr Pro Ala
450                 455                 460

Lys Gly Leu Pro Ile Arg Leu His Pro His Gln Val
465                 470                 475

<210> SEQ ID NO 10
<211> LENGTH: 1431
<212> TYPE: DNA
<213> ORGANISM: Stevia rebaudiana

<400> SEQUENCE: 10
atgatccagg ttctgacccc gatcctgctg ttcctgatct tcttcgtttt ctggaaagtt      60
tacaaacacc agaaaaccaa atcaacctg ccgccgggtt ctttcggttg ccgttcctg      120 ggtgaaaccc tggcgctgct gcgtgcgggt tgggactctg aaccggaacg tttcgttcgt      180
gaacgtatca aaaacacgg ttctccgctg gttttcaaaa cctctctgtt cggtgaccgt      240
ttcgcggttc tgtgcggtcc ggcgggtaac aaattcctgt tctgcaacga aacaaactg      300 gttgcgtctt ggtggccggt tccggttcgt aaactgttcg gtaaatctct gctgaccatc      360
cgtggtgacg aagcgaaatg gatgcgtaaa atgctgctgt cttacctggg tccggacgcg      420
ttcgcgaccc actacgcggt taccatggac gttgttaccc gtcgtcacat cgacgttcac      480
tggcgtggta agaagaagt taacgttttc agaccgtta aactgtacgc gttcgaactg      540
gcgtgccgtc tgttcatgaa cctggacgac ccgaaccaca tcgcgaaact gggttctctg      600
ttcaacatct tcctgaaagg tatcatcgaa ctgccgatcg acgttccggg tacccgtttc      660
tactcttcta aaaaagcggc ggcggcgatc cgtatcgaac tgaaaaaact gatcaaagcg      720

```
cgtaaactgg aactgaaaga aggtaaagcg tcttcttctc aggacctgct gtctcacctg    780
ctgacctctc cggacgaaaa cggtatgttc ctgaccgaag aagaaatcgt tgacaacatc    840
ctgctgctgc tgttcgcggg tcacgacacc tctgcgctgt ctatcaccct gctgatgaaa    900
accctgggtg aacactctga cgtttacgac aaagttctga agaacagct ggaaatctct     960 aaaaccaaag aagcgtggga atctctgaaa tgggaagaca tccagaaaat gaaatactct   1020
tggtctgtta tctgcgaagt tatgcgtctg aacccgccgg ttatcggtac ctaccgtgaa   1080
gcgctggttg acatcgacta cgcgggttac accatcccga aaggttggaa actgcactgg   1140
tctgcggttt ctacccagcg tgacgaagcg aacttcgaag acgttacccg tttcgacccg   1200
tctcgtttcg aaggtgcggg tccgaccccg ttcaccttcg ttccgttcgg tggtggtccg   1260
cgtatgtgcc tgggtaaaga attcgcgcgt ctggaagttc tggcgttcct gcacaacatc   1320
gttaccaact tcaaatggga cctgctgatc ccggacgaaa aaatcgaata cgacccgatg   1380
gcgaccccgg cgaaaggtct gccgatccgt ctgcacccgc accaggttta a             1431
```

<210> SEQ ID NO 11
<211> LENGTH: 481
<212> TYPE: PRT
<213> ORGANISM: Stevia rebaudiana

<400> SEQUENCE: 11

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
```

```
                    245                 250                 255
Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn

<210> SEQ ID NO 12
<211> LENGTH: 1446
<212> TYPE: DNA
<213> ORGANISM: Stevia rebaudiana

<400> SEQUENCE: 12
atggacgcga tggcgaccac cgaaaaaaaa ccgcacgtta tcttcatccc gttcccggcg      60
cagtctcaca tcaaagcgat gctgaaactg gcgcagctgc tgcaccacaa aggtctgcag     120
atcaccttcg ttaacaccga cttcatccac aaccagttcc tggaatcttc tggtccgcac     180
tgcctggacg tgcgccgggg tttccgtttc gaaaccatcc cggacggtgt ttctcactct     240
ccggaagcgt ctatcccgat ccgtgaatct ctgctgcgtt ctatcgaaac caacttcctg     300
gaccgtttca tcgacctggt taccaaactg ccggacccgc cgacctgcat catctctgac     360
ggtttcctgt ctgttttcac catcgacgcg gcgaaaaaac tgggtatccc ggttatgatg     420
tactggaccc tggcggcgtg cggtttcatg ggtttctacc acatccactc tctgatcgaa     480
aaaggtttcg cgccgctgaa agacgcgtct tacctgacca acgttacct ggacaccgtt     540 atcgactggg ttccgggtat ggaaggtatc cgtctgaaag acttcccgct ggactggtct     600
accgacctga acgacaaagt tctgatgttc accaccgaag cgccgcagcg ttctcacaaa     660
gtttctcacc acatcttcca caccttcgac gaactggaac cgtctatcat caaaacccg    720 tctctgcgtt acaaccacat ctacaccatc ggtccgctgc agctgctgct ggaccagatc     780
```

-continued

```
ccggaagaaa aaaaacagac cggtatcacc tctctgcacg gttactctct ggttaaagaa   840
gaaccggaat gcttccagtg gctgcagtct aaagaaccga actctgttgt ttacgttaac   900
ttcggttcta ccaccgttat gtctctggaa gacatgaccg aattcggttg gggtctggcg   960
aactctaacc actacttcct gtggatcatc cgttctaacc tggttatcgg tgaaaacgcg  1020
gttctgccgc cggaactgga agaacacatc aaaaaacgtg gtttcatcgc gtcttggtgc  1080
tctcaggaaa aagttctgaa acaccgtct gttggtggtt tcctgaccca ctgcggttgg  1140
ggttctacca tcgaatctct gtctgcgggt gttccgatga tctgctggcc gtactcttgg  1200
gaccagctga ccaactgccg ttacatctgc aaagaatggg aagttggtct ggaaatgggt  1260
accaaagtta acgtgacga agttaaacgt ctggttcagg aactgatggg tgaaggtggt  1320
cacaaaatgc gtaacaaagc gaaagactgg aagaaaaag cgcgtatcgc gatcgcgccg  1380
aacggttctt cttctctgaa catcgacaaa atggttaaag aaatcaccgt tctggcgcgt  1440
aactaa                                                              1446
```

<210> SEQ ID NO 13
<211> LENGTH: 460
<212> TYPE: PRT
<213> ORGANISM: Stevia rebaudiana

<400> SEQUENCE: 13

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
```

```
                245                 250                 255
Tyr Lys Ala Asn His His Glu Cys Met Asn Trp Leu Asp Asp Lys Pro
            260                 265                 270
Lys Glu Ser Val Val Tyr Val Ala Phe Gly Ser Leu Val Lys His Gly
        275                 280                 285
Pro Glu Gln Val Glu Glu Ile Thr Arg Ala Leu Ile Asp Ser Asp Val
    290                 295                 300
Asn Phe Leu Trp Val Ile Lys His Lys Glu Glu Gly Lys Leu Pro Glu
305                 310                 315                 320
Asn Leu Ser Glu Val Ile Lys Thr Gly Lys Gly Leu Ile Val Ala Trp
                325                 330                 335
Cys Lys Gln Leu Asp Val Leu Ala His Glu Ser Val Gly Cys Phe Val
            340                 345                 350
Thr His Cys Gly Phe Asn Ser Thr Leu Glu Ala Ile Ser Leu Gly Val
        355                 360                 365
Pro Val Val Ala Met Pro Gln Phe Ser Asp Gln Thr Thr Asn Ala Lys
    370                 375                 380
Leu Leu Asp Glu Ile Leu Gly Val Gly Val Arg Val Lys Ala Asp Glu
385                 390                 395                 400
Asn Gly Ile Val Arg Arg Gly Asn Leu Ala Ser Cys Ile Lys Met Ile
                405                 410                 415
Met Glu Glu Glu Arg Gly Val Ile Ile Arg Lys Asn Ala Val Lys Trp
            420                 425                 430
Lys Asp Leu Ala Lys Val Ala Val His Glu Gly Gly Ser Ser Asp Asn
        435                 440                 445
Asp Ile Val Glu Phe Val Ser Glu Leu Ile Lys Ala
    450                 455                 460

<210> SEQ ID NO 14
<211> LENGTH: 1383
<212> TYPE: DNA
<213> ORGANISM: Stevia rebaudiana

<400> SEQUENCE: 14
atggcggaac agcagaaaat caaaaaatct ccgcacgttc tgctgatccc gttcccgctg      60
cagggtcaca tcaacccgtt catccagttc ggtaaacgtc tgatctctaa aggtgttaaa     120
accaccctgg ttaccaccat ccacaccctg aactctaccc tgaaccactc taacaccacc     180
accacctcta tcgaaatcca ggcgatctct gacggttgcg acgaaggtgg tttcatgtct     240
gcgggtgaat cttacctgga aaccttcaaa caggttggtt ctaaatctct ggcggacctg     300
atcaaaaaac tgcagtctga aggtaccacc atcgacgcga tcatctacga ctctatgacc     360
gaatgggttc tggacgttgc gatcgaattc ggtatcgacg tggttctttt cttcacccag     420
gcgtgcgttg ttaactctct gtactaccac gttcacaaag gtctgatctc tctgccgctg     480
ggtgaaaccg tttctgttcc gggtttcccg gttctgcagc gttgggaaac cccgctgatc     540
ctgcagaacc acgaacagat ccagtctccg tggtctcaga tgctgttcgg tcagttcgcg     600
aacatcgacc aggcgcgttg ggtttttcacc aactctttct acaaactgga agaagaagtt     660
atcgaatgga cccgtaaaat ctggaacctg aaagttatcg gtccgaccct gccgtctatg     720
tacctggaca acgtctggga cgacgacaaa gacaacggtt tcaacctgta caaagcgaac     780
caccacgaat gcatgaactg gctggacgac aaaccgaaag atctgttgt tacgttgcg     840 ttcggttctc tggttaaaca cggtccggaa caggttgaag aaatcacccg tgcgctgatc     900
```

```
gactctgacg ttaacttcct gtgggttatc aaacacaaag aagaaggtaa actgccggaa      960
aacctgtctg aagttatcaa aaccggtaaa ggtctgatcg ttgcgtggtg caaacagctg     1020
gacgttctgg cgcacgaatc tgttggttgc ttcgttaccc actgcggttt caactctacc     1080
ctggaagcga tctctctggg tgttccggtt gttgcgatgc cgcagttctc tgaccagacc     1140
accaacgcga aactgctgga cgaaatcctg ggtgttggtg ttcgtgttaa agcggacgaa     1200
aacggtatcg ttcgtcgtgg taacctggcg tcttgcatca aatgatcat ggaagaagaa     1260 cgtggtgtta tcatccgtaa aaacgcggtt aaatggaaag acctggcgaa agttgcggtt     1320
cacgaaggtg ttcttctga caacgacatc gttgaattcg tttctgaact gatcaaagcg     1380
taa                                                                   1383
```

<210> SEQ ID NO 15
<211> LENGTH: 458
<212> TYPE: PRT
<213> ORGANISM: Stevia rebaudiana

<400> SEQUENCE: 15

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
    195                 200                 205

Lys Gln Thr Lys Ala Ser Ser Gly Val Ile Trp Asn Ser Phe Lys Glu
210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
    275                 280                 285
```

Glu Lys Asp Phe Leu Glu Ile Ala Arg Gly Leu Val Asp Ser Lys Gln
    290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
                325                 330                 335
Lys Trp Val Pro Gln Gln Glu Val Leu Ala His Gly Ala Ile Gly Ala
                340                 345                 350
Phe Trp Thr His Ser Gly Trp Asn Ser Thr Leu Glu Ser Val Cys Glu
                355                 360                 365
Gly Val Pro Met Ile Phe Ser Asp Phe Gly Leu Asp Gln Pro Leu Asn
370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
                405                 410                 415
Asp Glu Glu Gly Glu Tyr Ile Arg Gln Asn Ala Arg Val Leu Lys Gln
                420                 425                 430
Lys Ala Asp Val Ser Leu Met Lys Gly Gly Ser Ser Tyr Glu Ser Leu
435                 440                 445
Glu Ser Leu Val Ser Tyr Ile Ser Ser Leu
    450                 455

<210> SEQ ID NO 16
<211> LENGTH: 1377
<212> TYPE: DNA
<213> ORGANISM: Stevia rebaudiana

<400> SEQUENCE: 16
atggaaaaca aaaccgaaac accgttcgt cgtcgtcgtc gtatcatcct gttcccggtt      60
ccgttccagg gtcacatcaa cccgatcctg cagctggcga acgttctgta ctctaaaggt     120
ttctctatca ccatcttcca caccaacttc aacaaaccga aacctctaa ctacccgcac      180 ttcaccttcc gtttcatcct ggacaacgac ccgcaggacg aacgtatctc taacctgccg     240
acccacggtc cgctggcggg tatgcgtatc ccgatcatca cgaacacgg tgcggacgaa      300 ctgcgtcgtg aactggaact gctgatgctg cgtctgaag aagacgaaga gttcttgc        360 ctgatcaccg acgcgctgtg gtacttcgcg cagtctgttg cggactctct gaacctgcgt    420
cgtctggttc tgatgacctc ttctctgttc aacttccacg cgcacgtttc tctgccgcag    480
ttcgacgaac tgggttacct ggacccggac acaaaaccc gtctggaaga acaggcgtct    540
ggtttcccga tgctgaaagt taagacatc aaatctgcgt actctaactg gcagatcctg    600
aaagaaatcc tgggtaaaat gatcaaacag accaaagcgt cttctggtgt tatctggaac   660
tctttcaaag aactggaaga atctgaactg gaaaccgtta ccgtgaaat cccggcgccg    720 tctttcctga tcccgctgcc gaaacacctg accgcgtctt cttcttctct gctgaccac    780 gaccgtaccg ttttccagtg gctggaccag cagccgccgt cttctgttct gtacgtttct    840
ttcggttcta cctctgaagt tgacgaaaaa gacttcctgg aaatcgcgcg tggtctggtt    900
gactctaaac agtctttcct gtgggttgtt cgtccgggtt tcgttaaagg ttctacctgg    960
gttgaaccgc tgccggacgg tttcctgggt gaacgtggtc gtatcgttaa atgggttccg   1020
cagcaggaag ttctggcgca cggtgcgatc ggtgcgttct ggacccactc tggttggaac   1080
tctaccctgg aatctgtttg cgaaggtgtt ccgatgatct ctctgactt cggtctggac   1140

```
cagccgctga acgcgcgtta catgtctgac gttctgaaag ttggtgttta cctggaaaac  1200
ggttgggaac gtggtgaaat cgcgaacgcg atccgtcgtg ttatggttga cgaagaaggt  1260
gaatacatcc gtcagaacgc gcgtgttctg aaacagaaag cggacgtttc tctgatgaaa  1320
ggtggttctt cttacgaatc tctggaatct ctggtttctt acatctcttc tctgtaa     1377

<210> SEQ ID NO 17
<211> LENGTH: 704
<212> TYPE: PRT
<213> ORGANISM: Artemisia annua

<400> SEQUENCE: 17

Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
            20                  25                  30

Ser Asn Ile Pro Leu Ala Val Phe Met Glu Asn Arg Glu Leu Leu Met
        35                  40                  45

Ile Leu Thr Thr Ser Val Ala Val Leu Ile Gly Cys Val Val Val Leu
    50                  55                  60

Val Trp Arg Arg Ser Ser Ser Ala Ala Lys Lys Ala Ala Glu Ser Pro
65                  70                  75                  80

Val Ile Val Val Pro Lys Lys Val Thr Glu Asp Glu Val Asp Asp Gly
                85                  90                  95

Arg Lys Lys Val Thr Val Phe Phe Gly Thr Gln Thr Gly Thr Ala Glu
            100                 105                 110

Gly Phe Ala Lys Ala Leu Val Glu Glu Ala Lys Ala Arg Tyr Glu Lys
        115                 120                 125

Ala Val Phe Lys Val Ile Asp Leu Asp Asp Tyr Ala Ala Glu Asp Asp
    130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Glu Lys Gly Glu Trp Leu Asp Lys Leu
            180                 185                 190

Gln Tyr Ala Val Phe Gly Leu Gly Asn Arg Gln Tyr Glu His Phe Asn
        195                 200                 205

Lys Ile Ala Lys Val Val Asp Glu Lys Leu Val Glu Gln Gly Ala Lys
    210                 215                 220

Arg Leu Val Pro Val Gly Met Gly Asp Asp Gln Cys Ile Glu Asp
225                 230                 235                 240

Asp Phe Thr Ala Trp Lys Glu Leu Val Trp Pro Glu Leu Asp Gln Leu
                245                 250                 255

Leu Arg Asp Glu Asp Asp Thr Ser Val Ala Thr Pro Tyr Thr Ala Ala
            260                 265                 270

Val Ala Glu Tyr Arg Val Val Phe His Asp Lys Pro Glu Thr Tyr Asp
        275                 280                 285

Gln Asp Gln Leu Thr Asn Gly His Ala Val His Asp Ala Gln His Pro
    290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
                325                 330                 335
```

Ser Tyr Glu Thr Gly Asp His Val Gly Val Tyr Val Glu Asn Leu Ser
            340                 345                 350

Asp Val Val Asp Glu Ala Glu Lys Leu Ile Gly Leu Pro Pro His Thr
            355                 360                 365

Tyr Phe Ser Val His Ala Asp Asn Glu Asp Gly Thr Pro Leu Gly Gly
370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
            405                 410                 415

Ala Leu Ala Ala His Ala Thr Asp Ser Thr Glu Ala Asp Arg Leu Lys
            420                 425                 430

Phe Leu Ala Ser Pro Ala Gly Lys Asp Glu Tyr Ala Gln Trp Ile Val
            435                 440                 445

Ala Ser His Arg Ser Leu Leu Glu Val Met Glu Ala Phe Pro Ser Ala
            450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Ser Pro Lys Phe Ala Pro Asn Arg
            485                 490                 495

Ile His Val Thr Cys Ala Leu Val Tyr Glu Gln Thr Pro Ser Gly Arg
            500                 505                 510

Val His Lys Gly Val Cys Ser Thr Trp Met Lys Asn Ala Val Pro Met
            515                 520                 525

Thr Glu Ser Gln Asp Cys Ser Trp Ala Pro Ile Tyr Val Arg Thr Ser
530                 535                 540

Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
            565                 570                 575

Ala Gln Lys Glu Ala Gly Thr Glu Leu Gly Thr Ala Ile Leu Phe Phe
            580                 585                 590

Gly Cys Arg Asn Arg Lys Val Asp Phe Ile Tyr Glu Asp Glu Leu Asn
            595                 600                 605

Asn Phe Val Glu Thr Gly Ala Leu Ser Glu Leu Val Thr Ala Phe Ser
610                 615                 620

Arg Glu Gly Ala Thr Lys Glu Tyr Val Gln His Lys Met Thr Gln Lys
625                 630                 635                 640

Ala Ser Asp Ile Trp Asn Leu Leu Ser Glu Gly Ala Tyr Leu Tyr Val
            645                 650                 655

Cys Gly Asp Ala Lys Gly Met Ala Lys Asp Val His Arg Thr Leu His
            660                 665                 670

Thr Ile Val Gln Glu Gln Gly Ser Leu Asp Ser Ser Lys Ala Glu Leu
            675                 680                 685

Tyr Val Lys Asn Leu Gln Met Ala Gly Arg Tyr Leu Arg Asp Val Trp
690                 695                 700

<210> SEQ ID NO 18
<211> LENGTH: 1992
<212> TYPE: DNA
<213> ORGANISM: Artemisia annua

<400> SEQUENCE: 18
atggcgctgg acaaactgga cctgtacgtt atcatcaccc tggttgttgc ggttgcggcg     60

```
tacttcgcga aaaaccgtcg ttcttcttct gcggcgaaaa aagcggcgga atctccggtt    120
atcgttgttc cgaaaaaagt taccgaagac gaagttgacg acggtcgtaa aaaagttacc    180
gttttcttcg gtacccagac cggtaccgcg gaaggtttcg cgaaagcgct ggttgaagaa    240
gcgaaagcgc gttacgaaaa agcggttttc aaagttatcg acctggacga ctacgcggcg    300
gaagacgacg aatacgaaga aaaactgaaa aagaatctc tggcgttctt cttcctggcg     360
acctacggtg acggtgaacc gaccgacaac gcggcgcgtt tctacaaatg gttcaccgaa    420
ggtgaagaaa aaggtgaatg gctggacaaa ctgcagtacg cggttttcgg tctgggtaac    480
cgtcagtacg aacacttcaa caaaatcgcg aaagttgttg acgaaaaact ggttgaacag    540
ggtgcgaaac gtctggttcc ggttggtatg ggtgacgacg accagtgcat cgaagacgac    600
ttcaccgcgt ggaaagaact ggtttggccg gaactggacc agctgctgcg tgacgaagac    660
gacacctctg ttgcgacccc gtacaccgcg gcggttgcgg aataccgtgt tgtttttccac    720 gacaaaccgg aaacctacga ccaggaccag ctgaccaacg tcacgcggt tcacgacgcg    780 cagcacccgt gccgttctaa cgttgcggtt aaaaaagaac tgcactctcc gctgtctgac    840
cgttcttgca cccacctgga attcgacatc tctaacaccg tctgtctta cgaaaccggt    900 gaccacgttg gtgtttacgt tgaaaacctg tctgaagttg ttgacgaagc ggaaaaactg    960
atcggtctgc cgccgcacac ctacttctct gttcacgcgg acaacgaaga cggtacccccg   1020 ctgggtggtg cgtctctgcc gccgccgttc ccgccgtgca ccctgcgtaa agcgctggcg    1080
tcttacgcgg acgttctgtc ttctccgaaa aaatctgcgc tgctggcgct ggcggcgcac    1140
gcgaccgact ctaccgaagc ggaccgtctg aaattcctgg cgtctccggc gggtaaagac    1200
gaatacgcgc agtggatcgt tgcgtctcac cgttctctgc tggaagttat ggaagcgttc    1260
ccgtctgcga aaccgccgct gggtgttttc ttcgcgtctg ttgcgccgcg tctgcagccg    1320
cgttactact ctatctcttc ttctccgcgt ttcgcgccga accgtatcca cgttacctgc    1380
gcgctggttt acgaacagac cccgtctggt cgtgttcaca aaggtgtttg ctctacctgg    1440
atgaaaaacg cggttccgat gaccgaatct caggactgct cttgggcgcc gatctacgtt    1500
cgtacctcta acttccgtct gccgtctgac ccgaaagttc cggttatcat gatcggtccg    1560
ggtaccggtc tggcgccgtt ccgtggtttc ctgcaggaac gtctggcgca gaaagaagcg    1620
ggtaccgaac tgggtaccgc gatcctgttc ttcggttgcc gtaaccgtaa agttgacttc    1680
atctacgaag acgaactgaa caacttcgtt gaaaccggtg cgctgtctga actggttacc    1740
gcgttctctc gtgaaggtgc gaccaaagaa tacgttcagc acaaaatgac ccagaaagcg    1800
tctgacatct ggaacctgct gtctgaaggt gcgtacctgt acgtttgcgg tgacgcgaaa    1860
ggtatggcga aagacgttca ccgtaccctg cacaccatct tcaggaaca gggttctctg    1920 gactcttcta agcggaact gtacgttaaa aacctgcaga tggcgggtcg ttacctgcgt    1980
gacgtttggt aa                                                         1992
```

<210> SEQ ID NO 19
<211> LENGTH: 696
<212> TYPE: PRT
<213> ORGANISM: Phaeosphaeria sp. L487

<400> SEQUENCE: 19

```
Met Ala Gln Leu Asp Thr Leu Asp Ile Val Val Leu Ala Ala Leu Pro
1               5                   10                  15

Leu Gly Thr Val Ala Tyr Phe Thr Lys Gly Thr Tyr Trp Ala Val Ser
```

```
            20                  25                  30
Ala Asp Pro Tyr Ala Asn Pro Leu Thr Asn Ala Asn Gly Ala Ala Arg
            35                  40                  45
Ala Gly Lys Ser Arg Asn Ile Ile Glu Lys Leu Glu Glu Ser Asp Lys
        50                  55                  60
Asn Cys Val Val Phe Tyr Gly Ser Gln Thr Gly Thr Ala Glu Asp Tyr
65                  70                  75                  80
Ala Ser Arg Leu Ser Lys Glu Gly His Ser Arg Phe Gly Leu Asn Thr
                85                  90                  95
Met Val Ala Asp Leu Glu Glu Tyr Asp Phe Asp Asn Leu Asp Ser Phe
                100                 105                 110
Pro Glu Asp Lys Leu Ala Val Phe Val Leu Ala Thr Tyr Gly Glu Gly
                115                 120                 125
Glu Pro Thr Asp Asn Ala Val Glu Phe Tyr Glu Phe Ile Gly Ser Glu
            130                 135                 140
Asp Ile Thr Phe Ser Asp Gly Gly Ser Ile Asp Asp Lys Pro Leu Ser
145                 150                 155                 160
Lys Leu Asn Tyr Val Ala Phe Gly Leu Gly Asn Asn Thr Tyr Glu His
                165                 170                 175
Tyr Asn Ser Met Val Arg Asn Val Asp Lys Tyr Leu Thr Lys Leu Gly
            180                 185                 190
Ala Thr Arg Leu Gly Ser Ala Gly Glu Gly Asp Gly Ala Gly Thr
            195                 200                 205
Met Glu Glu Asp Phe Leu Ala Trp Lys Glu Pro Met Trp Ala Ala Val
        210                 215                 220
Ala Glu Lys Met Asn Leu Glu Glu Arg Glu Ala Glu Tyr Glu Ala Val
225                 230                 235                 240
Phe Glu Val Thr Glu Lys Pro Asp Leu Asn Ala Gln Asp Asp Thr Val
                245                 250                 255
Tyr Leu Gly Glu Pro Asn Lys Asn His Leu Glu Gly Asn Gln Lys Gly
            260                 265                 270
Pro Phe Asn Ala Asn Asn Pro Phe Ile Ala Pro Ile Val Glu Ser His
            275                 280                 285
Glu Leu Phe Thr Thr Lys Glu Arg Asn Cys Leu His Met Glu Ile Ser
        290                 295                 300
Ile Gly Gly Ser Asn Leu Ser Tyr Thr Thr Gly Asp His Ile Ala Ile
305                 310                 315                 320
Trp Pro Asn Asn Ala Gly Lys Glu Val Asp Arg Phe Phe Lys Val Leu
                325                 330                 335
Gly Lys Glu Asp Lys Arg His Thr Val Ile Ala Val Arg Gly Leu Asp
            340                 345                 350
Pro Thr Ala Lys Val Pro Phe Pro Ser Pro Thr Thr Tyr Asp Ala Ala
            355                 360                 365
Val Arg Phe His Leu Glu Ile Gly Ala Ala Val Ser Arg Gln Leu Val
        370                 375                 380
Ser Thr Ile Ala Gln Phe Ala Pro Asn Glu Asp Ile Lys Ala Glu Met
385                 390                 395                 400
Ala Lys Leu Gly Ser Asp Lys Asp Tyr Phe Lys Leu Gln Val Thr Asp
                405                 410                 415
Arg Asn Leu Asn Leu Ala Gln Leu Leu Glu Ile Cys Gly Lys Gly Gln
            420                 425                 430
Pro Trp Thr Lys Ile Pro Phe Ser Phe Met Phe Glu Ser Leu Leu Lys
            435                 440                 445
```

```
Ile Gln Pro Arg Tyr Tyr Ser Ile Ser Ser Ser Leu Val Gln Lys
    450                 455                 460

Asp Lys Val Ser Ile Thr Ala Val Val Glu Ser Leu Glu Arg Pro Gly
465                 470                 475                 480

Ala Pro His Val Leu Lys Gly Val Thr Thr Asn Tyr Leu Leu Ala Leu
                485                 490                 495

Lys Gln Lys Gln His Gly Asp Pro Asn Pro Asp Pro His Gly Leu Asn
            500                 505                 510

Tyr Ala Ile Thr Gly Pro Arg Asn Lys Tyr Asp Gly Ile His Val Pro
        515                 520                 525

Val His Val Arg His Ser Asn Phe Lys Leu Pro Ser Asp Pro Ser Lys
    530                 535                 540

Pro Ile Val Met Val Gly Pro Gly Thr Gly Val Ala Pro Phe Arg Gly
545                 550                 555                 560

Phe Val Gln Glu Arg Ala Ala Gln Ala Lys Ala Gly His Asn Val Gly
                565                 570                 575

Lys Thr Ile Leu Phe Phe Gly Cys Arg Lys Ala Ser Glu Asp Phe Leu
            580                 585                 590

Tyr Gln Asn Glu Trp Ala Gln Tyr Lys Glu Ala Leu Gly Asp Asn Phe
        595                 600                 605

Glu Ile Tyr Thr Ala Phe Ser Arg Asp Gly Pro Lys Lys Val Tyr Val
    610                 615                 620

Gln Asn His Leu Glu Glu His Gly Glu Val Asn Arg Leu Leu Glu
625                 630                 635                 640

Lys Lys Ala Tyr Phe Tyr Val Cys Gly Asp Ala Ala His Met Ala Arg
                645                 650                 655

Asp Val Asn Thr Leu Leu Gly Lys Leu Ile Ser Lys Tyr Arg Asn Val
            660                 665                 670

Ser Glu Thr Lys Gly Glu Glu Ile Val Lys Ala Met Arg Ala Ser Asn
        675                 680                 685

Gln Tyr Gln Glu Asp Val Trp Ser
    690                 695

<210> SEQ ID NO 20
<211> LENGTH: 2091
<212> TYPE: DNA
<213> ORGANISM: Phaeosphaeria sp. L487

<400> SEQUENCE: 20
atggcgcagc tggacaccct ggacatcgtt gttctggcgg cgctgccgct gggtaccgtt      60
gcgtacttca ccaaaggtac ctactgggcg gtttctgcgg acccgtacgc gaacccgctg     120
accaacgcga acggtgcggc gcgtgcgggt aaatctcgta acatcatcga aaaactggaa     180
gaatctgaca aaaactgcgt tgttttctac ggttctcaga ccggtaccgc ggaagactac     240
gcgtctcgtc tgtctaaaga aggtcactct cgtttcggtc tgaacaccat ggttgcggac     300
ctggaagaat acgacttcga acctggac tcttccgg aagacaaact ggcggttttc     360
gttctggcga cctacggtga aggtgaaccg accgacaacg cggttgaatt ctacgaattc     420 atcggtctg aagacatcac cttctctgac ggtggttcta tcgacgacaa accgctgtct     480
aaactgaact acgttgcgtt cggtctgggt aacaacacct acgaacacta caactctatg     540
gttcgtaacg ttgacaaata cctgaccaaa ctgggtgcga cccgtctggg ttctgcgggt     600
gaaggtgacg acggtgcggg taccatggaa gaagacttcc tggcgtggaa agaaccgatg     660
```

```
tgggcggcgg ttgcggaaaa aatgaacctg gaagaacgtg aagcggaata cgaagcggtt    720
ttcgaagtta ccgaaaaacc ggacctgaac gcgcaggacg acaccgttta cctgggtgaa    780
ccgaacaaaa accacctgga aggtaaccag aaaggtccgt tcaacgcgaa caacccgttc    840
atcgcgccga tcgttgaatc tcacgaactg ttcaccacca agaacgtaa  ctgcctgcac    900
atggaaatct ctatcggtgg ttctaacctg tcttacacca ccggtgacca catcgcgatc    960
tggccgaaca acgcgggtaa agaagttgac cgtttcttca agttctggg  taaagaagac   1020
aaacgtcaca ccgttatcgc ggttcgtggt ctggacccga ccgcgaaagt tccgttcccg   1080
tctccgacca cctacgacgc ggcggttcgt ttccacctgg aaatcggtgc ggcggtttct   1140
cgtcagctgg tttctaccat cgcgcagttc gcgccgaacg aagacatcaa agcggaaatg   1200
gcgaaactgg ttctgacaa  agactacttc aaactgcagg ttaccgaccg taacctgaac   1260
ctggcgcagc tgctggaaat ctgcggtaaa ggtcagccgt ggaccaaaat cccgttctct   1320
ttcatgttcg aatctctgct gaaaatccag ccgcgttact actctatctc ttcttcttct   1380
ctggttcaga agacaaagt  ttctatcacc gcggttgttg aatctctgga acgtccgggt   1440
gcgccgcacg ttctgaaagg tgttaccacc aactacctgc tggcgctgaa acagaaacag   1500
cacggtgacc cgaaccccga cccgcacggt ctgaactacg cgatcaccgg tccgcgtaac   1560
aaatacgacg gtatccacgt tccggttcac gttcgtcact ctaacttcaa actgccgtct   1620
gacccgtcta aaccgatcgt tatggttggt ccgggtaccg tgttgcgcc  gttccgtggt   1680
ttcgttcagg aacgtgcggc gcaggcgaaa gcgggtcaca cgttggtaa  aaccatcctg   1740
ttcttcggtt gccgtaaagc gtctgaagac ttcctgtacc agaacgaatg ggcgcagtac   1800
aaagaagcgc tgggtgacaa cttcgaaatc tacaccgcgt ctctcgtga  cggtccgaaa   1860
aaagtttacg ttcagaacca cctggaagaa cacggtgaag aagttaaccg tctgctggaa   1920
aaaaagcgt  acttctacgt ttgcggtgac gcggcgcaca tggcgcgtga cgttaacacc   1980
ctgctgggta aactgatctc taaataccgt aacgttctg  aaaccaaagg tgaagaaatc   2040
gttaaagcga tgcgtgcgtc taaccagtac caggaagacg tttggtctta a            2091
```

<210> SEQ ID NO 21
<211> LENGTH: 881
<212> TYPE: PRT
<213> ORGANISM: Physcomitrella patens

<400> SEQUENCE: 21

```
Met Ala Ser Ser Thr Leu Ile Gln Asn Arg Ser Cys Gly Val Thr Ser
1               5                   10                  15

Ser Met Ser Ser Phe Gln Ile Phe Arg Gly Gln Pro Leu Arg Phe Pro
            20                  25                  30

Gly Thr Arg Thr Pro Ala Ala Val Gln Cys Leu Lys Lys Arg Arg Cys
        35                  40                  45

Leu Arg Pro Thr Glu Ser Val Leu Glu Ser Ser Pro Gly Ser Gly Ser
    50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125
```

-continued

```
Val Gln Met Asn Glu Trp Ile Glu Glu Ile Arg Met Tyr Phe Arg Asn
    130                 135                 140
Met Thr Leu Gly Glu Ile Ser Met Ser Pro Tyr Asp Thr Ala Trp Val
145                 150                 155                 160
Ala Arg Val Pro Ala Leu Asp Gly Ser His Gly Pro Gln Phe His Arg
                165                 170                 175
Ser Leu Gln Trp Ile Ile Asp Asn Gln Leu Pro Asp Gly Asp Trp Gly
            180                 185                 190
Glu Pro Ser Leu Phe Leu Gly Tyr Asp Arg Val Cys Asn Thr Leu Ala
        195                 200                 205
Cys Val Ile Ala Leu Lys Thr Trp Gly Val Gly Ala Gln Asn Val Glu
    210                 215                 220
Arg Gly Ile Gln Phe Leu Gln Ser Asn Ile Tyr Lys Met Glu Glu Asp
225                 230                 235                 240
Asp Ala Asn His Met Pro Ile Gly Phe Glu Ile Val Phe Pro Ala Met
                245                 250                 255
Met Glu Asp Ala Lys Ala Leu Gly Leu Asp Leu Pro Tyr Asp Ala Thr
            260                 265                 270
Ile Leu Gln Gln Ile Ser Ala Glu Arg Glu Lys Met Lys Lys Ile
        275                 280                 285
Pro Met Ala Met Val Tyr Lys Tyr Pro Thr Thr Leu Leu His Ser Leu
    290                 295                 300
Glu Gly Leu His Arg Glu Val Asp Trp Asn Lys Leu Leu Gln Leu Gln
305                 310                 315                 320
Ser Glu Asn Gly Ser Phe Leu Tyr Ser Pro Ala Ser Thr Ala Cys Ala
                325                 330                 335
Leu Met Tyr Thr Lys Asp Val Lys Cys Phe Asp Tyr Leu Asn Gln Leu
            340                 345                 350
Leu Ile Lys Phe Asp His Ala Cys Pro Asn Val Tyr Pro Val Asp Leu
        355                 360                 365
Phe Glu Arg Leu Trp Met Val Asp Arg Leu Gln Arg Leu Gly Ile Ser
    370                 375                 380
Arg Tyr Phe Glu Arg Glu Ile Arg Asp Cys Leu Gln Tyr Val Tyr Arg
385                 390                 395                 400
Tyr Trp Lys Asp Cys Gly Ile Gly Trp Ala Ser Asn Ser Ser Val Gln
                405                 410                 415
Asp Val Asp Asp Thr Ala Met Ala Phe Arg Leu Leu Arg Thr His Gly
            420                 425                 430
Phe Asp Val Lys Glu Asp Cys Phe Arg Gln Phe Phe Lys Asp Gly Glu
        435                 440                 445
Phe Phe Cys Phe Ala Gly Gln Ser Ser Gln Ala Val Thr Gly Met Phe
    450                 455                 460
Asn Leu Ser Arg Ala Ser Gln Thr Leu Phe Pro Gly Glu Ser Leu Leu
465                 470                 475                 480
Lys Lys Ala Arg Thr Phe Ser Arg Asn Phe Leu Arg Thr Lys His Glu
                485                 490                 495
Asn Asn Glu Cys Phe Asp Lys Trp Ile Ile Thr Lys Asp Leu Ala Gly
            500                 505                 510
Glu Val Glu Tyr Asn Leu Thr Phe Pro Trp Tyr Ala Ser Leu Pro Arg
        515                 520                 525
Leu Glu His Arg Thr Tyr Leu Asp Gln Tyr Gly Ile Asp Asp Ile Trp
    530                 535                 540
```

```
Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
            565                 570                 575

Lys Glu Leu Glu Gln Val Ile Lys Trp Asn Ala Ser Cys Gln Phe Arg
        580                 585                 590

Asp Leu Glu Phe Ala Arg Gln Lys Ser Val Glu Cys Tyr Phe Ala Gly
    595                 600                 605

Ala Ala Thr Met Phe Glu Pro Glu Met Val Gln Ala Arg Leu Val Trp
610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
            645                 650                 655

Trp Asn Pro Glu Leu Ile Asn Gly Leu Pro Glu Gln Ala Lys Ile Leu
        660                 665                 670

Phe Met Gly Leu Tyr Lys Thr Val Asn Thr Ile Ala Glu Gly Ala Phe
    675                 680                 685

Met Ala Gln Lys Arg Asp Val His His Leu Lys His Tyr Trp Asp
690                 695                 700

Lys Leu Ile Thr Ser Ala Leu Lys Glu Ala Glu Trp Ala Glu Ser Gly
705                 710                 715                 720

Tyr Val Pro Thr Phe Asp Glu Tyr Met Glu Val Ala Glu Ile Ser Val
            725                 730                 735

Ala Leu Glu Pro Ile Val Cys Ser Thr Leu Phe Phe Ala Gly His Arg
        740                 745                 750

Leu Asp Glu Asp Val Leu Asp Ser Tyr Asp Tyr His Leu Val Met His
    755                 760                 765

Leu Val Asn Arg Val Gly Arg Ile Leu Asn Asp Ile Gln Gly Met Lys
770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
            805                 810                 815

Glu Leu Val Asp Asn Ser Met Gln Gln Leu Thr Tyr Glu Val Leu Arg
        820                 825                 830

Phe Thr Ala Val Pro Lys Ser Cys Lys Arg Ile His Leu Asn Met Ala
    835                 840                 845

Lys Ile Met His Ala Phe Tyr Lys Asp Thr Asp Gly Phe Ser Ser Leu
850                 855                 860

Thr Ala Met Thr Gly Phe Val Lys Lys Val Leu Phe Glu Pro Val Pro
865                 870                 875                 880

Glu

<210> SEQ ID NO 22
<211> LENGTH: 2646
<212> TYPE: DNA
<213> ORGANISM: Physcomitrella patens

<400> SEQUENCE: 22
atggcgtctt ctaccctgat ccagaaccgt tcttgcggtg ttacctcttc tatgtcttct    60
ttccaaattt ttcgtggtca gccgctgcgt tccccgggta cccgtacccc ggcggcggtt   120
cagtgcctga aaaacgtccg ttgcctgcgt ccgaccgaat ctgttctgga atcttctccg   180
```

```
ggttctggtt cttaccgtat cgttaccggt ccgtctggta tcaacccgtc ttctaacggt    240
cacctgcagg aaggttctct gacccaccgt ctgccgatcc cgatggaaaa atctatcgac    300
aacttccagt ctaccctgta cgtttctgac atctggtctg aaaccctgca gcgtaccgaa    360
tgcctgctgc aggttaccga aaacgttcag atgaacgaat ggatcgaaga aatccgtatg    420
tacttccgta acatgaccct gggtgaaatc tctatgtctc cgtacgacac cgcgtgggtt    480
gcgcgtgttc cggcgctgga cggttctcac ggtccgcagt tccaccgttc tctgcagtgg    540
atcatcgaca accagctgcc ggacggtgac tgggtgaac cgtctctgtt cctgggttac    600
gaccgtgttt gcaacaccct ggcgtgcgtt atcgcgctga aacctgggg tgttggtgcg    660 cagaacgttg aacgtggtat ccagttcctg cagtctaaca tctacaaaat ggaagaagac    720
gacgcgaacc acatgccgat cggtttcgaa atcgttttcc cggcgatgat ggaagacgcg    780
aaagcgctgg gtctggacct gccgtacgac gcgaccatcc tgcagcaaat tccgcggaa    840 cgtgaaaaaa aatgaaaaa aatcccgatg gcgatggttt acaaataccc gaccaccctg    900
ctgcactctc tggaaggtct gcaccgtgaa gttgactgga caaactgct gcagctgcag    960 tctgaaaacg gttctttcct gtactctccg gcgtctaccg cgtgcgcgct gatgtacacc   1020
aaagacgtta aatgcttcga ctacctgaac cagctgctga tcaaattcga ccacgcgtgc   1080
ccgaacgttt accggttga cctgttcgaa cgtctgtgga tggttgaccg tctgcagcgt   1140
ctgggtatct ctcgttactt cgaacgtgaa atccgtgact gctgcagta cgtttaccgt   1200 tactggaaag actgcggtat cggttgggcg tctaactctt ctgttcagga cgttgacgac   1260
accgcgatgg cgttccgtct gctgcgtacc cacggtttcg acgttaaaga agactgcttc   1320
cgtcagttct tcaaagacgg tgaattcttc tgcttcgcgg gtcagtcttc tcaggcggtt   1380 accggtatgt тcaacтгтc tcgtgcgtct cagaccctgt tcccgggtga atctctgctg   1440
aaaaaagcgc gtaccttctc tcgtaacttc ctgcgtacca acacgaaaa caacgaatgc   1500

ttcgacaaat ggatcatcac caaagacctg gcgggtgaag ttgaatacaa cctgaccttc   1560
ccgtggtacg cgtctctgcc gcgtctggaa caccgtacct acctggacca gtacggtatc   1620
gacgacatct ggatcggtaa atctctgtac aaaatgccgg cggttaccaa cgaagttttc   1680
ctgaaactgg cgaaagcgga cttcaacatg tgccaggcgc tgcacaaaaa agaactggaa   1740
caggttatca atggaacgc gtcttgccag ttccgtgacc tggaattcgc gcgtcagaaa   1800

tctgttgaat gctacttcgc gggtgcggcg accatgttcg aaccggaaat ggttcaggcg   1860
cgtctggttt gggcgcgttg ctgcgttctg accaccgttc tggacgacta cttcgaccac   1920
ggtaccccgg ttgaagaact gcgtgtttt cgттcaggcgg ttcgtacctg aacccggaa   1980 ctgatcaacg tctgccgga acaggcgaaa atcctgttca tgggtctgta caaaaccgtt   2040
aacaccatcg cggaagaagc gttcatggcg cagaaacgtg acgttcacca ccacctgaaa   2100
cactactggg acaaactgat cacctctgcg ctgaaagaag cggaatgggc ggaatctggt   2160
tacgttccga ccttcgacga atacatggaa gttgcgaaa tctctgttgc gctggaaccg   2220
atcgtttgct ctaccctgtt cttcgcgggt caccgtctgg acgaagacgt tctggactct   2280

tacgactacc cctggttat gcacctgttt aaccgtgttg gtcgtatcct gaacgacatc   2340 caggggтaтga atcgtgaagc gtctcagggt aaaatctctt ctgttcaaat ttatatggaa   2400
gaacacccgt ctgttccgtc tgaagcgatg gcgatcgcgc acctgcagga actggttgac   2460
aactctatga gcagctgac ctacgaagtt ctgcgtttca ccgcggttcc gaaatcttgc   2520
aaacgtatcc acctgaacat ggcgaaaatc atgcacgcgt tctacaaaga caccgacggt   2580
```

-continued

```
ttctcttctc tgaccgcgat gaccggtttc gttaaaaaag ttctgttcga accggttccg   2640
gaataa                                                              2646
```

<210> SEQ ID NO 23
<211> LENGTH: 952
<212> TYPE: PRT
<213> ORGANISM: Gibberella fujikuroi

<400> SEQUENCE: 23

```
Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
            20                  25                  30

Ser His His Ser Tyr Tyr Gly Leu Cys Ser Thr Ser Cys Gln Val Tyr
        35                  40                  45

Asp Thr Ala Trp Val Ala Met Ile Pro Lys Thr Arg Asp Asn Val Lys
    50                  55                  60

Gln Trp Leu Phe Pro Glu Cys Phe His Tyr Leu Leu Lys Thr Gln Ala
65                  70                  75                  80

Ala Asp Gly Ser Trp Gly Ser Leu Pro Thr Thr Gln Thr Ala Gly Ile
                85                  90                  95

Leu Asp Thr Ala Ser Ala Val Leu Ala Leu Leu Cys His Ala Gln Glu
            100                 105                 110

Pro Leu Gln Ile Leu Asp Val Ser Pro Asp Glu Met Gly Leu Arg Ile
        115                 120                 125

Glu His Gly Val Thr Ser Leu Lys Arg Gln Leu Ala Val Trp Asn Asp
    130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
            180                 185                 190

Asp Leu Glu Gln Val Tyr Gly Lys Pro Ser Ser Leu Leu His Ser Leu
        195                 200                 205

Glu Ala Phe Leu Gly Lys Leu Asp Phe Asp Arg Leu Ser His His Leu
    210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Gly Ile Ser Gly Thr
            260                 265                 270

Phe Pro Thr Thr His Phe Glu Cys Ser Trp Ile Ile Ala Thr Leu Leu
        275                 280                 285

Lys Val Gly Phe Thr Leu Lys Gln Ile Asp Gly Asp Gly Leu Arg Gly
    290                 295                 300

Leu Ser Thr Ile Leu Leu Glu Ala Leu Arg Asp Glu Asn Gly Val Ile
305                 310                 315                 320

Gly Phe Ala Pro Arg Thr Ala Asp Val Asp Asp Thr Ala Lys Ala Leu
                325                 330                 335

Leu Ala Leu Ser Leu Val Asn Gln Pro Val Ser Pro Asp Ile Met Ile
            340                 345                 350
```

```
Lys Val Phe Glu Gly Lys Asp His Phe Thr Thr Phe Gly Ser Glu Arg
            355                 360                 365
Asp Pro Ser Leu Thr Ser Asn Leu His Val Leu Leu Ser Leu Leu Lys
        370                 375                 380
Gln Ser Asn Leu Ser Gln Tyr His Pro Gln Ile Leu Lys Thr Thr Leu
385                 390                 395                 400
Phe Thr Cys Arg Trp Trp Gly Ser Asp His Cys Val Lys Asp Lys
                405                 410                 415
Trp Asn Leu Ser His Leu Tyr Pro Thr Met Leu Leu Val Glu Ala Phe
                420                 425                 430
Thr Glu Val Leu His Leu Ile Asp Gly Gly Glu Leu Ser Ser Leu Phe
            435                 440                 445
Asp Glu Ser Phe Lys Cys Lys Ile Gly Leu Ser Ile Phe Gln Ala Val
        450                 455                 460
Leu Arg Ile Ile Leu Thr Gln Asp Asn Asp Gly Ser Trp Arg Gly Tyr
465                 470                 475                 480
Arg Glu Gln Thr Cys Tyr Ala Ile Leu Ala Leu Val Gln Ala Arg His
                485                 490                 495
Val Cys Phe Phe Thr His Met Val Asp Arg Leu Gln Ser Cys Val Asp
            500                 505                 510
Arg Gly Phe Ser Trp Leu Lys Ser Cys Ser Phe His Ser Gln Asp Leu
        515                 520                 525
Thr Trp Thr Ser Lys Thr Ala Tyr Glu Val Gly Phe Val Ala Glu Ala
            530                 535                 540
Tyr Lys Leu Ala Ala Leu Gln Ser Ala Ser Leu Glu Val Pro Ala Ala
545                 550                 555                 560
Thr Ile Gly His Ser Val Thr Ser Ala Val Pro Ser Ser Asp Leu Glu
                565                 570                 575
Lys Tyr Met Arg Leu Val Arg Lys Thr Ala Leu Phe Ser Pro Leu Asp
                580                 585                 590
Glu Trp Gly Leu Met Ala Ser Ile Ile Glu Ser Ser Phe Phe Val Pro
            595                 600                 605
Leu Leu Gln Ala Gln Arg Val Glu Ile Tyr Pro Arg Asp Asn Ile Lys
        610                 615                 620
Val Asp Glu Asp Lys Tyr Leu Ser Ile Ile Pro Phe Thr Trp Val Gly
625                 630                 635                 640
Cys Asn Asn Arg Ser Arg Thr Phe Ala Ser Asn Arg Trp Leu Tyr Asp
                645                 650                 655
Met Met Tyr Leu Ser Leu Leu Gly Tyr Gln Thr Asp Glu Tyr Met Glu
                660                 665                 670
Ala Val Ala Gly Pro Val Phe Gly Asp Val Ser Leu Leu His Gln Thr
            675                 680                 685
Ile Asp Lys Val Ile Asp Asn Thr Met Gly Asn Leu Ala Arg Ala Asn
        690                 695                 700
Gly Thr Val His Ser Gly Asn Gly His Gln His Glu Ser Pro Asn Ile
705                 710                 715                 720
Gly Gln Val Glu Asp Thr Leu Thr Arg Phe Thr Asn Ser Val Leu Asn
                725                 730                 735
His Lys Asp Val Leu Asn Ser Ser Ser Asp Gln Asp Thr Leu Arg
                740                 745                 750
Arg Glu Phe Arg Thr Phe Met His Ala His Ile Thr Gln Ile Glu Asp
            755                 760                 765
Asn Ser Arg Phe Ser Lys Gln Ala Ser Ser Asp Ala Phe Ser Ser Pro
```

```
                770            775              780
Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                805                 810                 815

Leu Leu Gln Gly Lys Asp Ala Phe Pro Ser Gly Thr Gln Lys Tyr Leu
            820                 825                 830

Ile Ser Ser Val Met Arg His Ala Thr Asn Met Cys Arg Met Tyr Asn
                835                 840                 845

Asp Phe Gly Ser Ile Ala Arg Asp Asn Ala Glu Arg Asn Val Asn Ser
850                 855                 860

Ile His Phe Pro Glu Phe Thr Leu Cys Asn Gly Thr Ser Gln Asn Leu
865                 870                 875                 880

Asp Glu Arg Lys Glu Arg Leu Leu Lys Ile Ala Thr Tyr Glu Gln Gly
                885                 890                 895

Tyr Leu Asp Arg Ala Leu Glu Ala Leu Glu Arg Gln Ser Arg Asp Asp
            900                 905                 910

Ala Gly Asp Arg Ala Gly Ser Lys Asp Met Arg Lys Leu Lys Ile Val
            915                 920                 925

Lys Leu Phe Cys Asp Val Thr Asp Leu Tyr Asp Gln Leu Tyr Val Ile
            930                 935                 940

Lys Asp Leu Ser Ser Ser Met Lys
945                 950

<210> SEQ ID NO 24
<211> LENGTH: 2859
<212> TYPE: DNA
<213> ORGANISM: Gibberella fujikuroi

<400> SEQUENCE: 24
atgccgggta aaatcgaaaa cggtaccccg aaagacctga aaaccggtaa cgacttcgtt      60
tctgcggcga aatctctgct ggaccgtgcg ttcaaatctc accactctta ctacggtctg     120
tgctctacct cttgccaggt ttacgacacc gcgtgggttg cgatgatccc gaaaacccgt     180
gacaacgtta acagtggct gttcccggaa tgcttccact acctgctgaa acccaggcg      240 gcggacggtt cttggggttc tctgccgacc acccagaccg cgggtatcct ggacaccgcg     300
tctgcggttc tggcgctgct gtgccacgcg caggaaccgc tgcagatcct ggacgtttct     360
ccggacgaaa tgggtctgcg tatcgaacac ggtgttacct ctctgaaacg tcagctggcg     420
gtttggaacg acgttgaaga caccaaccac atcggtgttg aattcatcat cccggcgctg     480
ctgtctatgc tggaaaaaga actggacgtt ccgtctttcg aattcccgtg ccgttctatc     540
ctggaacgta tgcacggtga aaaactgggt cacttcgacc tggaacaggt ttacggtaaa     600
ccgtcttctc tgctgcactc tctggaagcg ttcctgggta aactggactt cgaccgtctg     660
tctcaccacc tgtaccacgg ttctatgatg gcgtctccgt cttctaccgc ggcgtacctg     720
atcggtgcga ccaaatggga cgacgaagcg gaagactacc tgcgtcacgt tatgcgtaac     780
ggtgcgggtc acggtaacgg tggtatctct ggtaccttcc cgaccaccca cttcgaatgc     840
tcttggatca tcgcgaccct gctgaaagtt ggtttcaccc tgaaacagat cgacggtgac     900
ggtctgcgtg gtctgtctac catcctgctg aagcgctgc gtgacgaaaa cggtgttatc     960
ggtttcgcgc gcgtaccgc ggacgttgac gacaccgcga aagcgctgct ggcgctgtct    1020
ctggttaacc agccggtttc tccggacatc atgatcaaag ttttcgaagg taaagaccac    1080
```

-continued

```
ttcaccacct tcggttctga acgtgacccg tctctgacct ctaacctgca cgttctgctg   1140
tctctgctga aacagtctaa cctgtctcag taccacccgc agatcctgaa aaccaccctg   1200
ttcacctgcc gttggtggtg gggttctgac cactgcgtta aagacaaatg gaacctgtct   1260
cacctgtacc cgaccatgct gctggttgaa gcgttcaccg aagttctgca cctgatcgac   1320
ggtggtgaac tgtcttctct gttcgacgaa tctttcaaat gcaaaatcgg tctgtctatc   1380
ttccaggcgg ttctgcgtat catcctgacc caggacaacg acggttcttg gcgtggttac   1440
cgtgaacaga cctgctacgc gatcctggcg ctggttcagg cgcgtcacgt ttgcttcttc   1500
acccacatgg ttgaccgtct gcagtcttgc gttgaccgtg gtttctcttg gctgaaatct   1560
tgctctttcc actctcagga cctgacctgg acctctaaaa ccgcgtacga agttggtttc   1620
gttgcggaag cgtacaaact ggcggcgctg cagtctgcgt ctctggaagt tccggcggcg   1680
accatcggtc actctgttac ctctgcggtt ccgtcttctg acctggaaaa atacatgcgt   1740
ctggttcgta aaaccgcgct gttctctccg ctggacgaat ggggtctgat ggcgtctatc   1800
atcgaatctt ctttcttcgt tccgctgctg caggcgcagc gtgttgaaat ctacccgcgt   1860
gacaacatca aagttgacga agacaaatac ctgtctatca tcccgttcac ctgggttggt   1920
tgcaacaacc gttctcgtac cttcgcgtct aaccgttggc tgtacgacat gatgtacctg   1980
tctctgctgg gttaccagac cgacgaatac atggaagcgg ttgcgggtcc ggttttcggt   2040
gacgtttctc tgctgcacca gaccatcgac aaagttatcg acaacaccat gggtaacctg   2100
gcgcgtgcga acggtaccgt tcactctggt aacggtcacc agcacgaatc tccgaacatc   2160
ggtcaggttg aagacaccct gacccgtttc accaactctg ttctgaacca caaagacgtt   2220
ctgaactctt cttcttctga ccaggacacc ctgcgtcgtg aattccgtac cttcatgcac   2280
gcgcacatca cccagatcga agacaactct cgtttctcta aacaggcgtc ttctgacgcg   2340
ttctcttctc cggaacagtc ttacttccag tgggttaact ctaccggtgg ttctcacgtt   2400
gcgtgcgcgt actctttcgc gttctctaac tgcctgatgt ctgcgaacct gctgcagggt   2460
aaagacgcgt tcccgtctgg tacccagaaa tacctgatct cttctgttat gcgtcacgcg   2520
accaacatgt gccgtatgta caacgacttc ggttctatcg cgcgtgacaa cgcggaacgt   2580
aacgttaact ctatccactt cccggaattc accctgtgca acggtacctc tcagaacctg   2640
gacgaacgta aagaacgtct gctgaaaatc gcgacctacg aacagggtta cctggaccgt   2700
gcgctggaag cgctggaacg tcagtctcgt gacgacgcgg gtgaccgtgc gggttctaaa   2760
gacatgcgta aactgaaaat cgttaaactg ttctgcgacg ttaccgacct gtacgaccag   2820
ctgtacgtta tcaaagacct gtcttcttct atgaaataa                          2859
```

<210> SEQ ID NO 25
<211> LENGTH: 587
<212> TYPE: PRT
<213> ORGANISM: Bradyrhizobium japonicum

<400> SEQUENCE: 25

```
Met Arg Asn Gly Trp Arg Asn Ser Tyr Ser Gly Pro Thr Arg Ile Cys
1               5                   10                  15

Ser Asn Thr Arg His Ala His Glu Arg Ala Arg Pro His Arg Val Ala
            20                  25                  30

Pro Val Pro Leu Arg Ser Ala Gly Gly Arg Val His Pro Ala Leu Cys
        35                  40                  45

Pro Ser Pro Arg Arg Arg Ser Gln Arg Leu Pro Ala Ala Ala His Val
    50                  55                  60
```

```
Ser Ala Asn Gly Thr Ser Arg Val Asn Ala Leu Ser Glu His Ile Leu
 65                  70                  75                  80

Ser Glu Leu Arg Arg Leu Leu Ser Glu Met Ser Asp Gly Gly Ser Val
                 85                  90                  95

Gly Pro Ser Val Tyr Asp Thr Ala Gln Ala Leu Arg Phe His Gly Asn
            100                 105                 110

Val Thr Gly Arg Gln Asp Ala Tyr Ala Trp Leu Ile Ala Gln Gln Gln
        115                 120                 125

Ala Asp Gly Gly Trp Gly Ser Ala Asp Phe Pro Leu Phe Arg His Ala
    130                 135                 140

Pro Thr Trp Ala Ala Leu Leu Ala Leu Gln Arg Ala Asp Pro Leu Pro
145                 150                 155                 160

Gly Ala Ala Asp Ala Val Gln Thr Ala Thr Arg Phe Leu Gln Arg Gln
                165                 170                 175

Pro Asp Pro Tyr Ala His Ala Val Pro Glu Asp Ala Pro Ile Gly Ala
            180                 185                 190

Glu Leu Ile Leu Pro Gln Phe Cys Gly Glu Ala Ala Ser Leu Leu Gly
        195                 200                 205

Gly Val Ala Phe Pro Arg His Pro Ala Leu Leu Pro Leu Arg Gln Ala
210                 215                 220

Cys Leu Val Lys Leu Gly Ala Val Ala Met Leu Pro Ser Gly His Pro
225                 230                 235                 240

Leu Leu His Ser Trp Glu Ala Trp Gly Thr Ser Pro Thr Thr Ala Cys
                245                 250                 255

Pro Asp Asp Asp Gly Ser Ile Gly Ile Ser Pro Ala Ala Thr Ala Ala
            260                 265                 270

Trp Arg Ala Gln Ala Val Thr Arg Gly Ser Thr Pro Gln Val Gly Arg
        275                 280                 285

Ala Asp Ala Tyr Leu Gln Met Ala Ser Arg Ala Thr Arg Ser Gly Ile
    290                 295                 300

Glu Gly Val Phe Pro Asn Val Trp Pro Ile Asn Val Phe Glu Pro Cys
305                 310                 315                 320

Trp Ser Leu Tyr Thr Leu His Leu Ala Gly Leu Phe Ala His Pro Ala
                325                 330                 335

Leu Ala Glu Ala Val Arg Val Ile Val Ala Gln Leu Asp Ala Arg Leu
            340                 345                 350

Gly Val His Gly Leu Gly Pro Ala Leu His Phe Ala Ala Asp Ala Asp
        355                 360                 365

Asp Thr Ala Val Ala Leu Cys Val Leu His Leu Ala Gly Arg Asp Pro
    370                 375                 380

Ala Val Asp Ala Leu Arg His Phe Glu Ile Gly Glu Leu Phe Val Thr
385                 390                 395                 400

Phe Pro Gly Glu Arg Asn Ala Ser Val Ser Thr Asn Ile His Ala Leu
                405                 410                 415

His Ala Leu Arg Leu Leu Gly Lys Pro Ala Ala Gly Ala Ser Ala Tyr
            420                 425                 430

Val Glu Ala Asn Arg Asn Pro His Gly Leu Trp Asp Asn Glu Lys Trp
        435                 440                 445

His Val Ser Trp Leu Tyr Pro Thr Ala His Ala Val Ala Ala Leu Ala
    450                 455                 460

Gln Gly Lys Pro Gln Trp Arg Asp Glu Arg Ala Leu Ala Ala Leu Leu
465                 470                 475                 480
```

```
Gln Ala Gln Arg Asp Asp Gly Gly Trp Gly Ala Arg Gly Ser Thr
                485                 490                 495

Phe Glu Glu Thr Ala Tyr Ala Leu Phe Ala Leu His Val Met Asp Gly
            500                 505                 510

Ser Glu Glu Ala Thr Gly Arg Arg Ile Ala Gln Val Val Ala Arg
            515                 520                 525

Ala Leu Glu Trp Met Leu Ala Arg His Ala His Gly Leu Pro Gln
            530                 535                 540

Thr Pro Leu Trp Ile Gly Lys Glu Leu Tyr Cys Pro Thr Arg Val Val
545                 550                 555                 560

Arg Val Ala Glu Leu Ala Gly Leu Trp Leu Ala Leu Arg Trp Gly Arg
                565                 570                 575

Arg Val Leu Ala Glu Gly Ala Gly Ala Ala Pro
            580                 585

<210> SEQ ID NO 26
<211> LENGTH: 1764
<212> TYPE: DNA
<213> ORGANISM: Bradyrhizobium japonicum

<400> SEQUENCE: 26
atgcgtaacg gttggcgtaa ctcttactct ggtccgaccc gtatctgctc taacacccgt      60
cacgcgcacg aacgtgcgcg tccgcaccgt gttgcgccgg ttccgctgcg ttctgcgggt     120
ggtcgtgttc acccggcgct gtgccgtctc cgcgtcgtc gttctcagcg tctgccggcg     180
gcggcgcacg tttctgcgaa cggtacctct cgtgttaacg cgctgtctga acacatcctg     240
tctgaactgc gtcgtctgct gtctgaaatg tctgacggtg gttctgttgg tccgtctgtt     300
tacgacaccg cgcaggcgct gcgtttccac ggtaacgtta ccggtcgtca ggacgcgtac     360
gcgtggctga tcgcgcagca gcaggcggac ggtggttggg gttctgcgga cttcccgctg     420
ttccgtcacg cgccgacctg gcggcgctg ctggcgctgc agcgtgcgga cccgctgccg     480
ggtgcggcgg acgcggttca gaccgcgacc cgtttcctgc agcgtcagcc ggacccgtac     540
gcgcacgcgg ttccggaaga cgcgccgatc ggtgcgaaac tgatcctgcc gcagttctgc     600
ggtgaagcgg cgtctctgct gggtggtgtt gcgttccgc gtcacccggc gctgctgccg     660
ctgcgtcagg cgtgcctggt taaactgggt gcggttgcga tgctgccgtc tggtcacccg     720
ctgctgcact cttgggaagc gtggggtacc tctccgacca ccgcgtgccc ggacgacgac     780
ggttctatcg gtatctctcc ggcggcgacc gcggcgtggc gtgcgcaggc ggttacccgt     840
ggttctaccc gcaggttgg tcgtgcggac gcgtacctgc agatggcgtc tcgtgcgacc     900
cgttctggta tcgaaggtgt tttcccgaac gtttggccga tcaacgtttt cgaaccgtgc     960
tggtctctgt acaccctgca cctggcgggt ctgttcgcgc accggcgct ggcggaagcg    1020 gttcgtgtta tcgttgcgca gctggacgcg cgtctgggtg ttcacggtct gggtccggcg    1080
ctgcacttcg cggcggacgc ggacgacacc gcggttgcgc tgtgcgttct gcacctggcg    1140
ggtcgtgacc cggcggttga cgcgctgcgt cacttcgaaa tcggtgaact gttcgttacc    1200
ttcccgggtg aacgtaacgc gtctgttttct accaacatcc acgcgctgca cgcgctgcgt    1260
ctgctgggta aaccggcggc gggtgcgtct cgtacgttga agcgaaccg taacccgcac    1320 ggtctgtggg acaacgaaaa atggcacgtt tcttggctgt acccgaccgc gcacgcggtt    1380
gcggcgctgg cgcagggtaa accgcagtgg cgtgacgaac gtgcgctggc ggcgctgctg    1440
caggcgcagc gtgacgacgg tggttgggt gcgggtcgtg gttctacctt cgaagaaacc    1500
```

```
gcgtacgcgc tgttcgcgct gcacgttatg gacggttctg aagaagcgac cggtcgtcgt    1560
cgtatcgcgc aggttgttgc gcgtgcgctg aatggatgc tggcgcgtca cgcggcgcac     1620
ggtctgccgc agaccccgct gtggatcggt aaagaactgt actgcccgac ccgtgttgtt    1680
cgtgttgcgg aactgcgggg tctgtggctg cgctgcgtt ggggtcgtcg tgttctggcg     1740
gaaggtgcgg gtgcggcgcc gtaa                                           1764
```

<210> SEQ ID NO 27
<211> LENGTH: 300
<212> TYPE: PRT
<213> ORGANISM: Bradyrhizobium japonicum

<400> SEQUENCE: 27

```
Met Ile Gln Thr Glu Arg Ala Val Gln Gln Val Leu Glu Trp Gly Arg
1               5                   10                  15

Ser Leu Thr Gly Phe Ala Asp Glu His Ala Val Glu Ala Val Arg Gly
            20                  25                  30

Gly Gln Tyr Ile Leu Gln Arg Ile His Pro Ser Leu Arg Gly Thr Ser
        35                  40                  45

Ala Arg Thr Gly Arg Asp Pro Gln Asp Glu Thr Leu Ile Val Thr Phe
    50                  55                  60

Tyr Arg Glu Leu Ala Leu Leu Phe Trp Leu Asp Asp Cys Asn Asp Leu
65                  70                  75                  80

Gly Leu Ile Ser Pro Glu Gln Leu Ala Ala Val Glu Gln Ala Leu Gly
                85                  90                  95

Gln Gly Val Pro Cys Ala Leu Pro Gly Phe Glu Gly Cys Ala Val Leu
            100                 105                 110

Arg Ala Ser Leu Ala Thr Leu Ala Tyr Asp Arg Arg Asp Tyr Ala Gln
        115                 120                 125

Leu Leu Asp Asp Thr Arg Cys Tyr Ser Ala Ala Leu Arg Ala Gly His
    130                 135                 140

Ala Gln Ala Val Ala Ala Glu Arg Trp Ser Tyr Ala Glu Tyr Leu His
145                 150                 155                 160

Asn Gly Ile Asp Ser Ile Ala Tyr Ala Asn Val Phe Cys Cys Leu Ser
                165                 170                 175

Leu Leu Trp Gly Leu Asp Met Ala Thr Leu Arg Ala Arg Pro Ala Phe
            180                 185                 190

Arg Gln Val Leu Arg Leu Ile Ser Ala Ile Gly Arg Leu Gln Asn Asp
        195                 200                 205

Leu His Gly Cys Asp Lys Asp Arg Ser Ala Gly Glu Ala Asp Asn Ala
    210                 215                 220

Val Ile Leu Leu Leu Gln Arg Tyr Pro Ala Met Pro Val Val Glu Phe
225                 230                 235                 240

Leu Asn Asp Glu Leu Ala Gly His Thr Arg Met Leu His Arg Val Met
                245                 250                 255

Ala Glu Glu Arg Phe Pro Ala Pro Trp Gly Pro Leu Ile Glu Ala Met
            260                 265                 270

Ala Ala Ile Arg Val Gln Tyr Tyr Arg Thr Ser Thr Ser Arg Tyr Arg
        275                 280                 285

Ser Asp Ala Val Arg Gly Gly Gln Arg Ala Pro Ala
    290                 295                 300
```

<210> SEQ ID NO 28
<211> LENGTH: 903
<212> TYPE: DNA

<213> ORGANISM: Bradyrhizobium japonicum

<400> SEQUENCE: 28

```
atgatccaga ccgaacgtgc ggttcagcag gttctggaat ggggtcgttc tctgaccggt    60
ttcgcggacg aacacgcggt tgaagcggtt cgtggtggtc agtacatcct gcagcgtatc   120
cacccgtctc tgcgtggtac ctctgcgcgt accggtcgtg acccgcagga cgaaaccctg   180
atcgttacct ctaccgtga actggcgctg ctgttctggc tggacgactg caacgacctg   240
ggtctgatct ctccggaaca gctggcggcg gttaacaggg cgctgggtca gggtgttccg   300
tgcgcgctgc cgggtttcga aggttgcgcg gttctgcgtg cgtctctggc gaccctggcg   360
tacgaccgtc gtgactacgc gcagctgctg gacgacaccc gttgctactc tgcggcgctg   420
cgtgcgggtc acgcgcaggc ggttgcggcg aacgttggt cttacgcgga atacctgcac   480
aacggtatcg actctatcgc gtacgcgaac gttttctgct gcctgtctct gctgtggggt   540
ctggacatgg cgaccctgcg tgcgcgtccg gcgttccgtc aggttctgcg tctgatctct   600
gcgatcggtc gtctgcagaa cgacctgcac ggttgcgaca agaccgttc tgcgggtgaa   660
gcggacaacg cggttatcct gctgctgcag cgttacccgg cgatgccggt tgttgagttc   720
ctgaacgacg aactggcggg tcacacccgt atgctgcacc gtgttatggc ggaagaacgt   780
ttcccggcgc cgtggggtcc gctgatcgaa gcgatggcgg cgatccgtgt tcagtactac   840
cgtacctcta cctctcgtta ccgttctgac gcggttcgtg gtggtcagcg tgcgccggcg   900
taa                                                                 903
```

<210> SEQ ID NO 29
<211> LENGTH: 429
<212> TYPE: PRT
<213> ORGANISM: Bradyrhizobium japonicum

<400> SEQUENCE: 29

```
Met Asp Val Gln Glu Thr Thr Ala Ala Cys Arg Asp Ala Phe Ala Glu
1               5                   10                  15

Leu Ala Ser Pro Ala Cys Ile His Asp Pro Tyr Pro Phe Met Arg Trp
            20                  25                  30

Leu Arg Glu His Asp Pro Val His Arg Ala Ala Ser Gly Leu Phe Leu
        35                  40                  45

Leu Ser Arg His Ala Asp Ile Phe Trp Ala Phe Lys Ala Thr Gly Asp
    50                  55                  60

Ala Phe Arg Gly Pro Ala Pro Gly Glu Leu Ala Arg Tyr Phe Ser Arg
65                  70                  75                  80

Ala Ala Thr Ser Pro Ser Leu Asn Leu Leu Ala Ser Thr Leu Ala Met
                85                  90                  95

Lys Asp Pro Pro Thr His Thr Arg Leu Arg Arg Leu Ile Ser Arg Asp
            100                 105                 110

Phe Thr Val Gly Gln Ile Asp Asn Leu Arg Pro Ser Ile Ala Arg Ile
        115                 120                 125

Val Ala Ala Arg Leu Asp Gly Ile Thr Pro Ala Leu Glu Arg Gly Glu
    130                 135                 140

Ala Val Asp Leu His Arg Glu Phe Ala Leu Ala Leu Pro Met Leu Val
145                 150                 155                 160

Phe Ala Glu Leu Phe Gly Met Pro Gln Asp Asp Met Phe Glu Leu Ala
                165                 170                 175

Ala Gly Ile Gly Thr Ile Leu Glu Gly Leu Gly Pro His Ala Ser Asp
            180                 185                 190
```

Pro Gln Leu Ala Ala Asp Ala Ala Ser Ala Arg Val Gln Ala Tyr
        195                 200                 205

Phe Gly Asp Leu Ile Gln Arg Lys Arg Thr Asp Pro Arg Arg Asp Ile
210                 215                 220

Val Ser Met Leu Val Gly Ala His Asp Asp Ala Asp Thr Leu Ser
225                 230                 235                 240

Asp Ala Glu Leu Ile Ser Met Leu Trp Gly Met Leu Leu Gly Gly Phe
                245                 250                 255

Val Thr Thr Ala Ala Ser Ile Asp His Ala Val Leu Ala Met Leu Ala
                260                 265                 270

Tyr Pro Glu Gln Arg His Trp Leu Gln Ala Asp Ala Ala Arg Val Arg
                275                 280                 285

Ala Phe Val Glu Glu Val Leu Arg Cys Asp Ala Pro Ala Met Phe Ser
290                 295                 300

Ser Ile Pro Arg Ile Ala Gln Arg Asp Ile Glu Leu Gly Gly Val Val
305                 310                 315                 320

Ile Pro Lys Asn Ala Asp Val Arg Val Leu Ile Ala Ser Gly Asn Arg
                325                 330                 335

Asp Pro Asp Ala Phe Ala Asp Pro Asp Arg Phe Asp Pro Ala Arg Phe
                340                 345                 350

Tyr Gly Thr Ser Pro Gly Met Ser Thr Asp Gly Lys Ile Met Leu Ser
                355                 360                 365

Phe Gly His Gly Ile His Phe Cys Leu Gly Ala Gln Leu Ala Arg Val
                370                 375                 380

Gln Leu Ala Glu Ser Leu Pro Arg Ile Gln Ala Arg Phe Pro Thr Leu
385                 390                 395                 400

Ala Phe Ala Gly Gln Pro Thr Arg Glu Pro Ser Ala Phe Leu Arg Thr
                405                 410                 415

Phe Arg Thr Leu Pro Val Arg Leu His Ala Gln Gly Ser
                420                 425

<210> SEQ ID NO 30
<211> LENGTH: 1290
<212> TYPE: DNA
<213> ORGANISM: Bradyrhizobium japonicum

<400> SEQUENCE: 30
atggacgttc aggaaaccac cgcggcgtgc cgtgacgcgt tcgcggaact ggcgtctccg      60
gcgtgcatcc acgacccgta cccgttcatg cgttggctgc gtgaacacga cccggttcac     120
cgtgcggcgt ctggtctgtt cctgctgtct cgtcacgcgg acatcttctg ggcgttcaaa     180
gcgaccggtg acgcgttccg tggtccggcg ccgggtgaac tggcgcgtta cttctctcgt     240
gcggcgacct ctccgtctct gaacctgctg gcgtctaccc tggcgatgaa agacccgccg     300
acccacaccc gtctgcgtcg tctgatctct cgtgacttca ccgtgggtca gatcgacaac     360
ctgcgtccgt ctatcgcgcg tatcgttgcg gcgcgtctgg acggtatcac cccggcgctg     420
gaacgtggtg aagcggttga cctgcaccgt gagttcgcgc tggcgctgcc gatgctggtt     480
ttcgcggaac tgttcggtat gccgcaggac gacatgttcg aactggcggc gggtatcggt     540
accatcctgg aaggtctggg tccgcacgcg tctgacccgc agctggcggc ggcggacgcg     600
gcgtctgcgc gtgttcaggc gtacttcggt gacctgatcc agcgtaaacg taccgacccg     660
cgtcgtgaca tcgtttctat gctggttggt gcgcacgacg acgcggga cacccctgtct     720 gacgcggaac tgatctctat gctgtggggt atgctgctgg gtggtttcgt taccaccgcg     780

```
gcgtctatcg accacgcggt tctggcgatg ctggcgtacc cggaacagcg tcactggctg    840
caggcggacg cggcgcgtgt tcgtgcgttc gttgaagaag ttctgcgttg cgacgcgccg    900
gcgatgttct cttctatccc gcgtatcgcg cagcgtgaca tcgaactggg tggtgttgtt    960
atcccgaaaa acgcggacgt tcgtgttctg atcgcgtctg gtaaccgtga cccggacgcg   1020
ttcgcggacc cggaccgttt cgacccggcg cgtttctacg gtacctctcc gggtatgtct   1080
accgacggta aaatcatgct gtctttcggt cacggtatcc acttctgcct gggtgcgcag   1140
ctggcgcgtg ttcagctggc ggaatctctg ccgcgtatcc aggcgcgttt cccgaccctg   1200
gcgttcgcgg gtcagccgac ccgtgaaccg tctgcgttcc tgcgtacctt ccgtaccctg   1260
ccggttcgtc tgcacgcgca gggttcttaa                                    1290
```

<210> SEQ ID NO 31
<211> LENGTH: 525
<212> TYPE: PRT
<213> ORGANISM: Gibberella fujikuroi

<400> SEQUENCE: 31

```
Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
        35                  40                  45

His Val Leu Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Pro Pro
            100                 105                 110

Asn Tyr Ile Asp Glu Val Arg Lys Leu Ser Gln Asp Lys Thr Arg Ser
        115                 120                 125

Val Glu Pro Phe Ile Asn Asp Phe Ala Gly Gln Tyr Thr Arg Gly Met
    130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
        195                 200                 205

Ala Arg Val Phe Leu Gly Pro Glu His Cys Arg Asn Gln Glu Trp Leu
    210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
```

```
                275                 280                 285
Leu Ser Trp Met Arg Asp Ala Ala Thr Gly Glu Glu Lys Gln Ile Asp
    290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Val Gly Ala
            340                 345                 350

Ser Gly Trp Asp Lys Thr Ala Leu Asn Arg Phe His Lys Leu Asp Ser
        355                 360                 365

Phe Leu Lys Glu Ser Gln Arg Phe Asn Pro Val Phe Leu Leu Thr Phe
    370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Pro Thr Glu Phe Asp Gly Phe
            420                 425                 430

Arg Tyr Ser Lys Ile Arg Ser Asp Ser Asn Tyr Ala Gln Lys Tyr Leu
        435                 440                 445

Phe Ser Met Thr Asp Ser Ser Asn Met Ala Phe Gly Tyr Gly Lys Tyr
    450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
            500                 505                 510

Ala Arg Leu Cys Val Arg Lys Arg Ser Leu Arg Asp Glu
        515                 520                 525

<210> SEQ ID NO 32
<211> LENGTH: 1578
<212> TYPE: DNA
<213> ORGANISM: Gibberella fujikuroi

<400> SEQUENCE: 32
atgtctaaat ctaactctat gaactctacc tctcacgaaa ccctgttcca gcagctggtt    60
ctgggtctgg accgtatgcc gctgatggac gttcactggc tgatctacgt tgcgttcggt   120
gcgtggctgt gctcttacgt tatccacgtt ctgtcttctt cttctaccgt taaagttccg   180
gttgttggtt accgttctgt tttcgaaccg acctggctgc tgcgtctgcg tttcgtttgg   240
gaaggtggtt ctatcatcgg tcagggttac aacaaattca agactctat cttccaggtt   300 cgtaaactgg gtaccgacat cgttatcatc ccgccgaact acatcgacga agttcgtaaa   360
ctgtctcagg acaaaacccg ttctgttgaa ccgttcatca cgacttcgc gggtcagtac   420 acccgtggta tggttttcct gcagtctgac ctgcagaacc gttgttatcca gcagcgtctg   480 accccgaaac tggtttctct gaccaaagtt atgaaagaag aactggacta cgcgctgacc   540
aaagaaatgc cggacatgaa aaacgacgaa tgggttgaag ttgacatctc ttctatcatg   600
gttcgtctga tctctcgtat ctctgcgcgt gttttcctgg tccggaaca ctgccgtaac   660 caggaatggc tgaccaccac cgcggaatac tctgaatctc tgttcatcac cggtttcatc   720
```

```
ctgcgtgttg ttccgcacat cctgcgtccg ttcatcgcgc cgctgctgcc gtcttaccgt      780
accctgctgc gtaacgtttc ttctggtcgt cgtgttatcg gtgacatcat ccgttctcag      840
cagggtgacg gtaacgaaga catcctgtct tggatgcgtg acgcggcgac cggtgaagaa      900
aaacagatcg acaacatcgc gcagcgtatg ctgatcctgt ctctggcgtc tatccacacc      960
accgcgatga ccatgaccca cgcgatgtac gacctgtgcg cgtgcccgga atacatcgaa     1020
ccgctgcgtg acgaagttaa atctgttgtt ggtgcgtctg gttgggacaa aaccgcgctg     1080
aaccgtttcc acaaactgga ctctttcctg aaagaatctc agcgtttcaa cccggttttc     1140
ctgctgacct tcaaccgtat ctaccaccag tctatgaccc tgtctgacgg taccaacatc     1200
ccgtctggta cccgtatcgc ggttccgtct cacgcgatgc tgcaggactc tgcgcacgtt     1260
ccgggtccga ccccgccgac cgaattcgac ggtttccgtt actctaaaat ccgttctgac     1320
tctaactacg cgcagaaata cctgttctct atgaccgact cttctaacat ggcgttcggt     1380
tacggtaaat acgcgtgccc gggtcgtttc tacgcgtcta cgaaatgaa actgaccctg     1440 gcgatcctgc tgctgcagtt cgaattcaaa ctgccggacg gtaaaggtcg tccgcgtaac     1500
atcaccatcg actctgacat gatcccggac ccgcgtgcgc gtctgtgcgt tcgtaaacgt     1560
tctctgcgtg acgaataa                                                   1578
```

<210> SEQ ID NO 33
<211> LENGTH: 713
<212> TYPE: PRT
<213> ORGANISM: Gibberella fujikuroi

<400> SEQUENCE: 33

```
Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
            20                  25                  30

Lys Asp Pro Tyr Ala Asn Gly Phe Ala Ala Gly Gly Ala Ser Lys Pro
        35                  40                  45

Gly Arg Thr Arg Asn Ile Val Glu Ala Met Glu Glu Ser Gly Lys Asn
    50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
            100                 105                 110

Ser Asp Asn Ile Val Met Phe Val Leu Ala Thr Tyr Gly Glu Gly Glu
        115                 120                 125

Pro Thr Asp Asn Ala Val Asp Phe Tyr Glu Phe Ile Thr Gly Glu Asp
    130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
            180                 185                 190

Gly Glu Ala Gly Glu Gly Asp Asp Gly Ala Gly Thr Met Glu Glu Asp
        195                 200                 205

Phe Leu Ala Trp Lys Asp Pro Met Trp Glu Ala Leu Ala Lys Lys Met
    210                 215                 220
```

```
Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
            245                 250                 255

Pro Asn Lys Leu His Leu Glu Gly Thr Ala Lys Gly Pro Phe Asn Ser
        260                 265                 270

His Asn Pro Tyr Ile Ala Pro Ile Ala Glu Ser Tyr Glu Leu Phe Ser
    275                 280                 285

Ala Lys Asp Arg Asn Cys Leu His Met Glu Ile Asp Ile Ser Gly Ser
290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
            340                 345                 350

Val Pro Phe Pro Asn Pro Thr Thr Tyr Asp Ala Ile Leu Arg Tyr His
        355                 360                 365

Leu Glu Ile Cys Ala Pro Val Ser Arg Gln Phe Val Ser Thr Leu Ala
370                 375                 380

Ala Phe Ala Pro Asn Asp Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
            420                 425                 430

Ile Pro Phe Ser Ala Phe Ile Glu Gly Leu Thr Lys Leu Gln Pro Arg
        435                 440                 445

Tyr Tyr Ser Ile Ser Ser Ser Leu Val Gln Pro Lys Lys Ile Ser
    450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro Val His Val Arg
        515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590

Trp Gln Glu Tyr Lys Glu Ala Leu Gly Asp Lys Phe Glu Met Ile Thr
        595                 600                 605

Ala Phe Ser Arg Glu Gly Ser Lys Lys Val Tyr Val Gln His Arg Leu
    610                 615                 620

Lys Glu Arg Ser Lys Glu Val Ser Asp Leu Leu Ser Gln Lys Ala Tyr
625                 630                 635                 640
```

```
            Phe Tyr Val Cys Gly Asp Ala Ala His Met Ala Arg Glu Val Asn Thr
                            645                 650                 655

Val Leu Ala Gln Ile Ile Ala Glu Gly Arg Gly Val Ser Glu Ala Lys
                        660                 665                 670

Gly Glu Glu Ile Val Lys Asn Met Arg Ser Ala Asn Gln Tyr Gln Val
                    675                 680                 685

Cys Ser Asp Phe Val Thr Leu His Cys Lys Glu Thr Thr Tyr Ala Asn
                690                 695                 700

Ser Glu Leu Gln Glu Asp Val Trp Ser
            705                 710
```

```
<210> SEQ ID NO 34
<211> LENGTH: 2142
<212> TYPE: DNA
<213> ORGANISM: Gibberella fujikuroi

<400> SEQUENCE: 34
```

| | | | | | |
|---|---|---|---|---|---|
| atggcggaac | tggacaccct | ggacatcgtt | gttctgggtg | ttatcttcct | gggtaccgtt | 60 |
| gcgtacttca | ccaaaggtaa | actgtggggt | gttaccaaag | acccgtacgc | gaacggtttc | 120 |
| gcggcgggtg | gtgcgtctaa | accggtcgt | acccgtaaca | tcgttgaagc | gatggaagaa | 180 |
| tctggtaaaa | actgcgttgt | tttctacggt | tctcagaccg | gtaccgcgga | agactacgcg | 240 |
| tctcgtctgg | cgaaagaagg | taaatctcgt | ttcggtctga | caccatgat | cgcggacctg | 300 |
| gaagactacg | acttcgacaa | cctggacacc | gttccgtctg | acaacatcgt | tatgttcgtt | 360 |
| ctggcgacct | acggtgaagg | tgaaccgacc | gacaacgcgg | ttgacttcta | cgaattcatc | 420 |
| accggtgaag | acgcgtcttt | caacgaaggt | aacgacccgc | cgctgggtaa | cctgaactac | 480 |
| gttgcgttcg | gtctgggtaa | caacacctac | gaacactaca | actctatggt | tcgtaacgtt | 540 |
| aacaaagcgc | tggaaaaact | gggtgcgcac | cgtatcggtg | aagcgggtga | aggtgacgac | 600 |
| ggtgcgggta | ccatggaaga | agacttcctg | gcgtggaaag | acccgatgtg | ggaagcgctg | 660 |
| gcgaaaaaaa | tgggtctgga | agaacgtgaa | gcggtttacg | aaccgatctt | cgcgatcaac | 720 |
| gaacgtgacg | acctgacccc | ggaagcgaac | gaagtttacc | tgggtgaacc | gaacaaactg | 780 |
| cacctggaag | gtaccgcgaa | aggtccgttc | aactctcaca | cccgtacat | cgcgccgatc | 840 |
| gcggaatctt | acgaactgtt | ctctgcgaaa | gaccgtaact | gcctgcacat | ggaaatcgac | 900 |
| atctctggtt | ctaacctgaa | atacgaaacc | ggtgaccaca | tcgcgatctg | gccgaccaac | 960 |
| ccgggtgaag | aagttaacaa | attcctggac | atcctggacc | tgtctggtaa | acagcactct | 1020 |
| gttgttaccg | ttaaagcgct | ggaaccgacc | gcgaaagttc | cgttcccgaa | cccgaccacc | 1080 |
| tacgacgcga | tcctgcgtta | ccacctggaa | atctgcgcgc | cggtttctcg | tcagttcgtt | 1140 |
| tctaccctgg | cggcgttcgc | gccgaacgac | gacatcaaag | cggaaatgaa | ccgtctgggt | 1200 |
| tctgacaaag | actacttcca | cgaaaaaacc | ggtccgcact | actacaacat | cgcgcgtttc | 1260 |
| ctggcgtctg | tttctaaagg | tgaaaaatgg | accaaaatcc | cgttctctgc | gttcatcgaa | 1320 |
| ggtctgacca | aactgcagcc | gcgttactac | tctatctctt | cttcttctct | ggttcagccg | 1380 |
| aaaaaaatct | ctatcaccgc | ggttgttgaa | tctcagcaga | tcccgggtcg | tgacgacccg | 1440 |
| ttccgtggtg | ttgcgaccaa | ctacctgttc | gcgctgaaac | agaaacagaa | cggtgacccg | 1500 |
| aacccggcgc | cgttcggtca | gtcttacgaa | ctgaccggtc | cgcgtaacaa | atacgacggt | 1560 |
| atccacgttc | cggttcacgt | tcgtcactct | aacttcaaac | tgccgtctga | cccgggtaaa | 1620 |
| ccgatcatca | tgatcggtcc | gggtaccggt | gttgcgccgt | tccgtggttt | cgttcaggaa | 1680 |

-continued

```
cgtgcgaaac aggcgcgtga cggtgttgaa gttggtaaaa ccctgctgtt cttcggttgc    1740
cgtaaatcta ccgaagactt catgtaccag aaagaatggc aggaatacaa agaagcgctg    1800
ggtgacaaat tcgaaatgat caccgcgttc tctcgtgaag ttctaaaaa agtttacgtt     1860 cagcaccgtc tgaaagaacg ttctaaagaa gtttctgacc tgctgtctca gaaagcgtac    1920
ttctacgttt gcggtgacgc ggcgcacatg gcgcgtgaag ttaacaccgt tctggcgcag    1980
atcatcgcgg aaggtcgtgg tgtttctgaa gcgaaaggtg aagaaatcgt taaaaacatg    2040
cgttctgcga accagtacca ggtttgctct gacttcgtta ccctgcactg caaagaaacc    2100
acctacgcga actctgaact gcaggaagac gtttggtctt aa                       2142
```

<210> SEQ ID NO 35
<211> LENGTH: 710
<212> TYPE: PRT
<213> ORGANISM: Stevia rebaudiana

<400> SEQUENCE: 35

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Lys Lys Glu Lys Glu Ser Glu
                85                  90                  95

Val Asp Asp Gly Lys Lys Val Ser Ile Phe Tyr Gly Thr Gln Thr
                100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Lys Gly Glu Trp
                180                 185                 190

Leu Lys Lys Leu Gln Tyr Gly Val Phe Gly Leu Gly Asn Arg Gln Tyr
            195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Thr Ser Val Thr Thr Pro
            260                 265                 270

Tyr Thr Ala Ala Val Leu Glu Tyr Arg Val Val Tyr His Asp Lys Pro
    275                 280                 285

Ala Asp Ser Tyr Ala Glu Asp Gln Thr His Thr Asn Gly His Val Val
```

```
                    290                 295                 300
His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                    325                 330                 335

Ile Ser His Thr Gly Leu Ser Tyr Glu Thr Gly Asp His Val Gly Val
                340                 345                 350

Tyr Ser Glu Asn Leu Ser Glu Val Val Asp Glu Ala Leu Lys Leu Leu
            355                 360                 365

Gly Leu Ser Pro Asp Thr Tyr Phe Ser Val His Ala Asp Lys Glu Asp
    370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710
```

<210> SEQ ID NO 36
<211> LENGTH: 2133
<212> TYPE: DNA
<213> ORGANISM: Stevia rebaudiana

<400> SEQUENCE: 36

```
atgcagtctg actctgttaa agtttctccg ttcgacctgg tttctgcggc gatgaacggt      60
aaagcgatgg aaaaactgaa cgcgtctgaa tctgaagacc cgaccaccct gccggcgctg     120
aaaatgctgg ttgaaaaccg tgaactgctg accctgttca ccacctcttt cgcggttctg     180
atcggttgcc tggttttcct gatgtggcgt cgttcttctt ctaaaaaact ggttcaggac     240
ccggttccgc aggttatcgt tgttaaaaaa aagaaaaag aatctgaagt tgacgacggt     300
aaaaaaaag tttctatctt ctacggtacc cagaccggta ccgcgaagg tttcgcgaaa      360
gcgctggttg aagaagcgaa agttcgttac gaaaaaacct ctttcaaagt tatcgacctg     420
gacgactacg cggcggacga cgacgaatac gaagaaaaac tgaaaaaaga atctctggcg     480
ttcttcttcc tggcgaccta cggtgacggt gaaccgaccg acaacgcggc gaacttctac     540
aaatggttca ccgaaggtga cgacaaaggt gaatggctga aaaaactgca gtacggtgtt     600
ttcggtctgg gtaaccgtca gtacgaacac ttcaacaaaa tcgcgatcgt tgttgacgac     660
aaactgaccg aaatgggtgc gaaacgtctg gttccggttg gtctgggtga cgacgaccag     720
tgcatcgaag acgacttcac cgcgtggaaa gaactggttt ggccggaact ggaccagctg     780
ctgcgtgacg aagacgacac ctctgttacc accccgtaca ccgcggcggt tctggaatac     840
cgtgttgttt accacgacaa accggcggac tcttacgcgg aagaccagac ccacaccaac     900
ggtcacgttg ttcacgacgc gcagcacccg tctcgttcta cgttgcgtt caaaaaagaa     960
ctgcacacct ctcagtctga ccgttcttgc acccacctgg aattcgacat ctctcacacc    1020
ggtctgtctt acgaaaccgg tgaccacgtt ggtgtttact ctgaaaacct gtctgaagtt    1080
gttgacgaag cgctgaaact gctgggtctg tctccggaca cctacttctc tgttcacgcg    1140
gacaaagaag acggtacccc gatcggtggt gcgtctctgc cgccgccgtt cccgccgtgc    1200
accctgcgtg acgcgctgac ccgttacgcg gacgttctgt cttctccgaa aaagttgcg    1260
ctgctggcgc tggcggcgca cgcgtctgac ccgtctgaag cggaccgtct gaaattcctg    1320
gcgtctccgg cgggtaaaga cgaatacgcg cagtggatcg ttgcgaacca gcgttctctg    1380
ctggaagtta tgcagtcttt cccgtctgcg aaaccgccgc tgggtgtttt cttcgcggcg    1440
gttgcgccgc gtctgcagcc gcgttactac tctatctctt cttctccgaa aatgtctccg    1500
aaccgtatcc acgttacctg cgcgctggtt tacgaaacca ccccggcggg tcgtatccac    1560
cgtggtctgt gctctaccty gatgaaaaac gcggttccgc tgaccgaatc tccggactgc    1620
tctcaggcgt ctatcttcgt tcgtacctct aacttccgtc tgccggttga cccgaaagtt    1680
ccggttatca tgatcggtcc gggtaccggt ctggcgccgt tcgtggtttt cctgcaggaa    1740
cgtctggcgc tgaaagaatc tggtaccgaa ctgggttctt ctatcttctt cttcggttgc    1800
cgtaaccgta agttgactt catctacgaa gacgaactga caacttcgt tgaaaccggt    1860
gcgctgtctg aactgatcgt tgcgttctct cgtgaaggta ccgcgaaaga atacgttcag    1920
cacaaatgt ctcagaaagc gtctgacatc tggaaactgc tgtctgaagg tgcgtacctg    1980
tacgtttgcg gtgacgcgaa aggtatggcg aaagacttc accgtaccct gcacaccatc    2040
gttcaggaac agggttctct ggactcttct aaagcggaac tgtacgttaa aaacctgcag    2100
```

```
atgtctggtc gttacctgcg tgacgtttgg taa                                    2133
```

<210> SEQ ID NO 37
<211> LENGTH: 509
<212> TYPE: PRT
<213> ORGANISM: Arabidopsis thaliana

<400> SEQUENCE: 37

```
Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
            20                  25                  30

Lys Asn Met Ser Glu Val Ser Thr Leu Pro Ser Val Pro Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365
```

```
Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
                420                 425                 430

Asp Gly Lys Tyr Glu Thr Ser Asp Leu His Lys Thr Met Ala Phe Gly
                435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
                500                 505

<210> SEQ ID NO 38
<211> LENGTH: 1530
<212> TYPE: DNA
<213> ORGANISM: Arabidopsis thaliana

<400> SEQUENCE: 38
atggcgttct tctctatgat ctctatcctg ctgggtttcg ttatctcttc tttcatcttc      60
atcttcttct tcaaaaaact gctgtctttc tctcgtaaaa acatgtctga agtttctacc     120
ctgccgtctg ttccggttgt tccgggtttc ccggttatcg gtaacctgct gcagctgaaa     180
gaaaaaaaac cgcacaaaac cttcacccgt tggtctgaaa tctacggtcc gatctactct     240
atcaaaatgg gttcttcttc tctgatcgtt ctgaactcta ccgaaaccgc gaaagaagcg     300
atggttaccc gtttctcttc tatctctacc cgtaaactgt ctaacgcgct gaccgttctg     360
acctgcgaca atctctatgg tgcgaccctc gactacgacg acttccacaa actggttaaa     420
cgttgcctgc tgaacggtct gctgggtgcg aacgcgcaga acgtaaacg tcactaccgt     480 gacgcgctga tcgaaaacgt ttcttctaaa ctgcacgcgc acgcgcgtga ccacccgcag     540
gaaccggtta acttccgtgc gatcttcgaa acgaactgt tcggtgttgc gctgaaacag     600
gcgttcggta agacgttga atctatctac gttaaagaac tgggtgttac cctgtctaaa     660
gacgaaatct tcaaagttct ggttcacgac atgatggaag gtgcgatcga cgttgactgg     720
cgtgacttct tcccgtacct gaaatggatt ccgaacaaat ctttcgaagc gcgtatccag     780
cagaaacaca aacgtcgtct ggcggttatg aacgcgctga tccaggaccg tctgaaacag     840
aacggttctg aatctgacga cgactgctac ctgaacttcc tgatgtctga agcgaaaacc     900
ctgaccaaag aacagatcgc gatcctggtt tgggaaacca tcatcgaaac gcggacacc     960 accctggtta ccaccgaatg ggcgatctac gaactggcga acacccgtc tgttcaggac    1020 cgtctgtgca agaaatcca gaacgtttgc ggtggtgaaa aattcaaaga agaacagctg    1080
tctcaggttc cgtacctgaa cggtgttttc acgaaaccc tgcgtaaata ctctccggcg    1140
ccgctggttc cgatccgtta cgcgcacgaa gacacccaga tcggtggtta ccacgttccg    1200
gcgggttctg aaatcgcgat caacatctac ggttgcaaca tggacaaaaa acgttgggaa    1260
cgtccggaag actggtggcc ggaacgtttc ctggacgacg gtaaatacga aacctctgac    1320
```

```
ctgcacaaaa ccatggcgtt cggtgcgggt aaacgtgttt gcgcgggtgc gctgcaggcg    1380
tctctgatgg cgggtatcgc gatcggtcgt ctggttcagg aattcgaatg gaaactgcgt    1440
gacggtgaag aagaaaacgt tgacacctac ggtctgacct ctcagaaact gtacccgctg    1500
atggcgatca tcaacccgcg tcgttcttaa                                     1530
```

<210> SEQ ID NO 39
<211> LENGTH: 490
<212> TYPE: PRT
<213> ORGANISM: Arabidopsis thaliana

<400> SEQUENCE: 39

```
Met Thr Ser Ala Tyr Ala Ser Asp Lys Lys Ser Ile Met Gly Thr Asp
1               5                   10                  15

Ser Ser Asp Asp Val Val Val Ile Ala Thr Thr Ser Ala Val Ala Gly
            20                  25                  30

Val Val Trp Lys Lys Thr Thr Ala Asp Arg Ser Gly Lys Met Ile Lys
        35                  40                  45

Ser Met Ala Lys Asp Asp Asp Asp Gly Ser Gly Lys Thr Arg Val
    50                  55                  60

Ser Ile Gly Thr Thr Gly Thr Ala Gly Ala Lys Ala Ser Ile Lys Ala
65                  70                  75                  80

Arg Tyr Lys Ala Ala Val Lys Val Ile Asp Asp Asp Tyr Ala Ala Asp
                85                  90                  95

Asp Asp Tyr Lys Lys Lys Thr Ala Cys Val Ala Thr Tyr Gly Asp Gly
            100                 105                 110

Thr Asp Asn Ala Ala Arg Ser Lys Trp Thr Asn Arg Asp Ile Lys Ala
        115                 120                 125

Tyr Gly Val Ala Gly Asn Arg Tyr His Asn Lys Ile Gly Ile Val Asp
    130                 135                 140

Cys Lys Lys Gly Ala Lys Arg Ile Val Gly Gly Asp Asp Ser Ile
145                 150                 155                 160

Asp Asp Asn Ala Trp Lys Ser Trp Ser Asp Lys Lys Asp Asp Lys
                165                 170                 175

Ser Val Ala Thr Tyr Thr Ala Val Ile Tyr Arg Val Thr His Asp
            180                 185                 190

Arg Thr Thr Lys Ser Met Ser Asn Val Ala Asn Gly Asn Thr Thr Ile
        195                 200                 205

Asp Ile His His Cys Arg Val Asp Val Ala Val Lys His Thr His Ser
    210                 215                 220

Asp Arg Ser Cys Ile His Asp Ile Ser Arg Thr Gly Ile Thr Tyr Thr
225                 230                 235                 240

Gly Asp His Val Gly Val Tyr Ala Asn His Val Ile Val Ala Gly Lys
                245                 250                 255

Gly His Ser Asp Val Ser Ile His Ala Asp Lys Asp Gly Ser Ser Ala
            260                 265                 270

Val Gly Cys Thr Gly Thr Gly Ala Arg Tyr Ala Asp Asn Arg Lys Ser
        275                 280                 285

Ala Val Ala Ala Ala Tyr Ala Thr Ser Ala Lys Lys His Thr Ser Asp
    290                 295                 300

Gly Lys Asp Tyr Ser Trp Ile Val Ala Ser Arg Ser Val Met Ala Ala
305                 310                 315                 320

Ser Ala Lys Gly Val Ala Ala Ile Ala Arg Arg Tyr Tyr Ser Ile Ser
                325                 330                 335
```

```
Ser Cys Asp Trp Ala Ser Arg Val His Val Thr Ser Ala Val Tyr Gly
            340                 345                 350

Thr Thr Gly Arg Ile His Lys Gly Val Cys Ser Thr Trp Met Lys Asn
        355                 360                 365

Ala Val Ala Lys Ser His Cys Ser Gly Ala Ile Ile Arg Ala Ser Asn
    370                 375                 380

Lys Ser Asn Ser Thr Ile Val Met Val Gly Thr Gly Ala Arg Gly
385                 390                 395                 400

Arg Met Ala Lys Asp Gly Gly Ser Ser Gly Cys Arg Asn Arg Met Asp
                405                 410                 415

Ile Tyr Asp Asn Asn Val Asp Gly Val Ile Ser Ile Met Ala Ser Arg
                420                 425                 430

Gly Ala Lys Tyr Val His Lys Met Met Lys Ala Ala Val Trp Asp Ile
            435                 440                 445

Lys Gly Tyr Tyr Val Cys Gly Asp Ala Lys Gly Met Ala Arg Asp Val
            450                 455                 460

His Arg Thr His Thr Ile Val Gly Val Ser Ser Ser Ala Ala Ile Val
465                 470                 475                 480

Lys Lys Thr Gly Arg Tyr Arg Asp Val Trp
                485                 490

<210> SEQ ID NO 40
<211> LENGTH: 1473
<212> TYPE: DNA
<213> ORGANISM: Arabidopsis thaliana

<400> SEQUENCE: 40
```

| | | | | |
|---|---|---|---|---|
| atgacctctg cgtacgcgtc tgacaaaaaa tctatcatgg gtaccgactc ttctgacgac | | | | 60 |
| gttgttgtta tcgcgaccac ctctgcggtt gcgggtgttg tttggaaaaa aaccaccgcg | | | | 120 |
| gaccgttctg gtaaaatgat caaatctatg gcgaaagacg acgacgacga cggttctggt | | | | 180 |
| aaaacccgtg tttctatcgg taccaccggt accgcgggtg cgaaagcgtc tatcaaagcg | | | | 240 |
| cgttacaaag cggcggttaa agttatcgac gacgactacg cggcggacga cgactacaaa | | | | 300 |
| aaaaaaaccg cgtgcgttgc gacctacggt gacggtaccg acaacgcggc gcgttctaaa | | | | 360 |
| tggaccaacc gtgacatcaa agcgtacggt gttgcgggta accgttacca caacaaaatc | | | | 420 |
| ggtatcgttg actgcaaaaa aggtgcgaaa cgtatcgttg tggtgacga cgactctatc | | | | 480 |
| gacgacaacg cgtggaaatc ttggtctgac aaaaaagacg acgacaaatc tgttgcgacc | | | | 540 |
| tacaccgcgg ttatctaccg tgttgttacc cacgaccgta ccaccaaatc tatgtctaac | | | | 600 |
| gttgcgaacg gtaacaccac catcgacatc caccactgcc gtgttgacgt tgcggttaaa | | | | 660 |
| cacacccact ctgaccgttc ttgcatccac gacatctctc gtaccggtat cacctacacc | | | | 720 |
| ggtgaccacg ttggtgttta cgcgaaccac gttatcgttg cgggtaaagg tcactctgac | | | | 780 |
| gtttctatcc acgcggacaa agacggttct tctgcggttg gttgcaccgg taccggtgcg | | | | 840 |
| cgttacgcgg acaaccgtaa atctgcggtt gcggcggcgt acgcgacctc tgcgaaaaaa | | | | 900 |
| cacacctctg acggtaaaga ctactcttgg atcgttgcgt ctcgttctgt tatggcggcg | | | | 960 |
| tctgcgaaag tgttgcggc gatcgcgcgt cgttactact ctatctcttc ttgcgactgg | | | | 1020 |
| gcgtctcgtg ttcacgttac ctctgcggtt tacggtacca ccggtcgtat ccacaaaggt | | | | 1080 |
| gtttgctcta cctggatgaa aaacgcggtt gcgaaatctc actgctctgg tgcgatcatc | | | | 1140 |
| cgtgcgtcta acaaatctaa ctctaccatc gttatggttg tggtaccgg tgcgcgtggt | | | | 1200 |
| cgtatggcga agacggtgg ttcttctggt tgccgtaacc gtatggacat ctacgacaac | | | | 1260 |

```
aacgttgacg gtgttatctc tatcatggcg tctcgtggtg cgaaatacgt tcacaaaatg    1320
atgaaagcgg cggtttggga catcaaaggt tactacgttt gcggtgacgc gaaaggtatg    1380
gcgcgtgacg ttcaccgtac ccacaccatc gttggtgttt cttcttctgc ggcgatcgtt    1440
aaaaaaaccg gtcgttaccg tgacgtttgg taa                                 1473
```

<210> SEQ ID NO 41
<211> LENGTH: 432
<212> TYPE: PRT
<213> ORGANISM: Starmerella bombicola

<400> SEQUENCE: 41

```
Met Ala Ile Glu Lys Pro Val Ile Val Ala Cys Ala Cys Pro Leu Ala
1               5                   10                  15

Gly His Val Gly Pro Val Leu Ser Leu Val Arg Gly Leu Leu Asn Arg
            20                  25                  30

Gly Tyr Glu Val Thr Phe Val Thr Gly Asn Ala Phe Lys Glu Lys Val
        35                  40                  45

Ile Glu Ala Gly Cys Thr Phe Val Pro Leu Gln Gly Arg Ala Asp Tyr
    50                  55                  60

His Glu Tyr Asn Leu Pro Glu Ile Ala Pro Gly Leu Leu Thr Ile Pro
65                  70                  75                  80

Pro Gly Leu Glu Gln Thr Gly Tyr Ser Met Asn Glu Ile Phe Val Lys
                85                  90                  95

Ala Ile Pro Glu Gln Tyr Asp Ala Leu Gln Thr Ala Leu Lys Gln Val
            100                 105                 110

Glu Ala Glu Asn Lys Ser Ala Val Val Ile Gly Glu Thr Met Phe Leu
        115                 120                 125

Gly Val His Pro Ile Ser Leu Gly Ala Pro Gly Leu Lys Pro Gln Gly
    130                 135                 140

Val Ile Thr Leu Gly Thr Ile Pro Cys Met Leu Lys Ala Glu Lys Ala
145                 150                 155                 160

Pro Gly Val Pro Ser Leu Glu Pro Met Ile Asp Thr Leu Val Arg Gln
                165                 170                 175

Gln Val Phe Gln Pro Gly Thr Asp Ser Glu Lys Glu Ile Met Lys Thr
            180                 185                 190

Leu Gly Ala Thr Lys Glu Pro Glu Phe Leu Leu Glu Asn Ile Tyr Ser
        195                 200                 205

Ser Pro Asp Arg Phe Leu Gln Leu Cys Pro Pro Ser Leu Glu Phe His
    210                 215                 220

Leu Thr Ser Pro Pro Gly Phe Ser Phe Ala Gly Ser Ala Pro His
225                 230                 235                 240

Val Lys Ser Ala Gly Leu Ala Thr Pro Pro His Leu Pro Ser Trp Trp
                245                 250                 255

Pro Asp Val Leu Ser Ala Lys Arg Leu Ile Val Val Thr Gln Gly Thr
            260                 265                 270

Ala Ala Ile Asn Tyr Glu Asp Leu Leu Ile Pro Ala Leu Gln Ala Phe
        275                 280                 285

Ala Asp Glu Glu Asp Thr Leu Val Val Gly Ile Leu Gly Val Lys Gly
    290                 295                 300

Ala Ser Leu Pro Asp Ser Val Lys Val Pro Ala Asn Ala Arg Ile Val
305                 310                 315                 320

Asp Tyr Phe Pro Tyr Asp Glu Leu Leu Pro His Ala Ser Val Phe Ile
                325                 330                 335
```

```
Tyr Asn Gly Gly Tyr Gly Gly Leu Gln His Ser Leu Ser His Gly Val
            340                 345                 350

Pro Val Ile Ile Gly Gly Met Leu Val Asp Lys Pro Ala Val Ala
        355                 360                 365

Ser Arg Ala Val Trp Ala Gly Val Gly Tyr Asp Leu Gln Thr Leu Gln
        370                 375                 380

Ala Thr Ser Glu Leu Val Ser Thr Ala Val Lys Glu Val Leu Ala Thr
385                 390                 395                 400

Pro Ser Tyr His Glu Lys Ala Met Ala Val Lys Lys Glu Leu Glu Lys
                405                 410                 415

Tyr Lys Ser Leu Asp Ile Leu Glu Ser Ala Ile Ser Glu Leu Ala Ser
            420                 425                 430

<210> SEQ ID NO 42
<211> LENGTH: 1299
<212> TYPE: DNA
<213> ORGANISM: Starmerella bombicola

<400> SEQUENCE: 42
atggccatcg agaaaccagt gatagttgct tgtgcctgcc cactagcggg gcacgtgggc      60
ccagtgctca gcctggtccg cggtctactc aatagaggat atgaggtgac tttcgtaaca     120
gggaacgcat tcaaggagaa agttattgag gcaggatgca ctttcgtccc tctccaagga     180
cgagctgact accatgaata caatctccct gaaatcgctc aggattgct cacgattcct      240 ccaggccttg agcagaccgg ttactcaatg aatgagattt tgtgaaggc gattcctgag      300 cagtacgatg cacttcaaac tgctctaaaa caggttgagg ctgaaaataa atcagctgtg     360
gtgattggcg agaccatgtt tctaggggtg catccgattt cactgggtgc ccaggtctc     420 aagccccaag gcgtaatcac gttaggaact attccgtgca tgctgaaagc agagaaggcg     480
cctggagttc ctagtcttga gccaatgatt gatactttag tgcggcaaca agtatttcaa     540
ccaggaactg actctgagaa ggagatcatg aagacgctcg gggccacgaa ggagcccgaa     600
tttctcctgg agaatatata cagcagccct gacagatttt tgcaactgtg ccctccatct     660
cttgaatttc acttgacttc gcctcctcct ggcttctcgt tcgctggtag tgcaccgcat     720
gtaaagtctg ctggattagc aactccacct cacctgccgt cttggtggcc tgatgtgctg     780
agtgcgaagc gtctgattgt tgttacacaa ggaacagcag ccatcaacta tgaggatctg     840
ctcattccag cattgcaggc ctttgctgac gaagaagaca ctctcgtagt tggtatattg     900
ggcgtcaaag gggcgtcact tcctgatagc gttaaagttc ctgcaaacgc tcgaattgtt     960 gattatttc cttacgatga gctactaccg catgcctctg ttttcatata caacggtgga    1020
tacgagggtc tgcagcacag tttgagccat ggcgttcccg tcatcatcgg aggaggaatg    1080
ttggtagaca agccagctgt tgcttcacga gctgtatggg ctggtgttgg ttatgatctt    1140
caaaccttgc aggcaacttc tgagctagtc tccacggccg ttaaggaggt gttggctact    1200
ccctcgtatc acgagaaagc catggcagtc aagaaagagc ttgaaaaata caagtctctt    1260
gatattctgg agtcggcaat tagtgaatta gcttcttaa                           1299

<210> SEQ ID NO 43
<211> LENGTH: 522
<212> TYPE: PRT
<213> ORGANISM: Stevia rebaudiana

<400> SEQUENCE: 43
```

-continued

```
Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Ser Phe Ile Tyr Lys
            20                  25                  30

Thr Ser Lys Lys Thr Cys Thr Pro Pro Lys Ala Ser Gly Glu His Pro
        35                  40                  45

Ile Thr Gly His Leu Asn Leu Leu Ser Gly Ser Ser Gly Leu Pro His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
                100                 105                 110

Tyr Leu Ala Ala Lys Ile Leu Gly Phe Asn Tyr Val Ser Phe Ser Phe
            115                 120                 125

Ala Pro Tyr Gly Pro Tyr Trp Val Gly Ile Arg Lys Ile Ile Ala Thr
    130                 135                 140

Lys Leu Met Ser Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190

Trp Glu Leu Asn Met Asn Ile Val Leu Arg Thr Val Ala Gly Lys Gln
                195                 200                 205

Tyr Thr Gly Thr Val Asp Asp Ala Asp Ala Lys Arg Ile Ser Glu Leu
    210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255

Glu Leu Val Ala Ser Arg Leu Asp Ser Met Val Ser Lys Trp Leu Asp
                260                 265                 270

Glu His Arg Lys Lys Gln Ala Asn Asp Lys Lys Glu Asp Met Asp
            275                 280                 285

Phe Met Asp Ile Met Ile Ser Met Thr Glu Ala Asn Ser Pro Leu Glu
            290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
                325                 330                 335

Leu Leu Leu Asn Asn Arg Asp Thr Leu Lys Lys Ala Gln Glu Glu Leu
            340                 345                 350

Asp Met Cys Val Gly Lys Gly Arg Gln Val Asn Glu Ser Asp Leu Val
            355                 360                 365

Asn Leu Ile Tyr Leu Glu Ala Val Leu Lys Glu Ala Leu Arg Leu Tyr
    370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
                405                 410                 415

Trp Lys Leu His Arg Asp Pro Asn Ile Trp Ser Asp Pro Cys Glu Phe
```

```
                420             425             430
Lys Pro Glu Arg Phe Leu Thr Pro Asn Gln Lys Asp Val Asp Val Ile
            435                 440                 445

Gly Met Asp Phe Glu Leu Ile Pro Phe Gly Ala Gly Arg Arg Tyr Cys
        450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
                485                 490                 495

Met Thr Ala Ser Val Gly Met Thr Asn Ala Lys Ala Ser Pro Leu Glu
                500                 505                 510

Val Leu Leu Ser Pro Arg Val Lys Trp Ser
            515                 520

<210> SEQ ID NO 44
<211> LENGTH: 1569
<212> TYPE: DNA
<213> ORGANISM: Stevia rebaudiana

<400> SEQUENCE: 44
atgggtctgt tcccgctgga agactcttac gcgctggttt cgaaggtct ggcgatcacc      60 ctggcgctgt actacctgct gtctttcatc tacaaaacct ctaaaaaaac ctgcaccccg     120
ccgaaagcgt ctggtgaaca cccgatcacc ggtcacctga acctgctgtc tggttcttct    180
ggtctgccgc acctggcgct ggcgtctctg gcggaccgtt gcggtccgat cttcaccatc    240
cgtctgggta tccgtcgtgt tctggttgtt tctaactggg aaatcgcgaa agaaatcttc    300
accacccacg acctgatcgt ttctaaccgt ccgaaatacc tggcggcgaa atcctgggt    360 ttcaactacg tttctttctc tttcgcgccg tacggtccgt actgggttgg tatccgtaaa    420
atcatcgcga ccaaactgat gtcttcttct cgtctgcaga actgcagttc gttcgtgtt    480 ttcgaactgg aaaactctat gaaatctatc cgtgaatctt ggaaagaaaa aaaagacgaa    540
gaaggtaaag ttctggttga atgaaaaaa tggttctggg aactgaacat gaacatcgtt    600
ctgcgtaccg ttgcgggtaa acagtacacc ggtaccgttg acgacgcgga cgcgaaacgt    660
atctctgaac tgttccgtga atggttccac tacaccggtc gtttcgttgt tggtgacgcg    720
ttcccgttcc tgggttggct ggacctgggt ggttacaaaa aaccatggaa actggttgcg    780
tctcgtctgg actctatggt ttctaaatgg ctggacgaac cgtaaaaaa acaggcgaac    840 gacgacaaaa aagaagacat ggacttcatg gacatcatga tctctatgac cgaagcgaac    900
tctccgctgg aaggttacgg taccgacacc atcatcaaaa ccacctgcat gaccctgatc    960
gtttctggtg ttgacaccac ctctatcgtt ctgacctggg cgctgtctct gctgctgaac   1020
aaccgtgaca ccctgaaaaa agcgcaggaa gaactggaca tgtgcgttgg taaaggtcgt   1080
caggttaacg aatctgacct ggttaacctg atctacctgg aagcggttct gaaagaagcg   1140
ctgcgtctgt acccggcggc gttcctgggt ggtccgcgtg cgttcctgga agactgcacc   1200
gttgcgggtt accgtatccc gaaaggtacc tgcctgctga tcaacatgtg gaaactgcac   1260
cgtgacccga catctggtc tgacccgtgc gaattcaaac cggaacgttt cctgaccccg   1320
aaccagaaag acgttgacgt tatcggtatg gacttcgaac tgatcccgtt cggtgcgggt   1380
cgtcgttact gcccgggtac ccgtctggcg ctgcagatgc tgcacatcgt tctggcgacc   1440
ctgctgcaga acttcgaaat gtctaccccg aacgacgcgc cggttgacat gaccgcgtct   1500
gttggtatga ccaacgcgaa agcgtctccg ctggaagttc tgctgtctcc gcgtgttaaa   1560
``` tggtcttaa 1569

<210> SEQ ID NO 45
<211> LENGTH: 361
<212> TYPE: PRT
<213> ORGANISM: Stevia rebaudiana

<400> SEQUENCE: 45

| Met | Ala | Leu | Val | Asn | Pro | Thr | Ala | Leu | Phe | Tyr | Gly | Thr | Ser | Ile | Arg |
|---|---|---|---|---|---|---|---|---|---|---|---|---|---|---|---|
| 1 | | | | 5 | | | | | 10 | | | | | 15 | |

Thr Arg Pro Thr Asn Leu Leu Asn Pro Thr Gln Lys Leu Arg Pro Val
            20                  25                  30

Ser Ser Ser Ser Leu Pro Ser Phe Ser Ser Val Ser Ala Ile Leu Thr
                35                  40                  45

Glu Lys His Gln Ser Asn Pro Ser Glu Asn Asn Leu Gln Thr His
 50                  55                  60

Leu Glu Thr Pro Phe Asn Phe Asp Ser Tyr Met Leu Glu Lys Val Asn
65                  70                  75                  80

Met Val Asn Glu Ala Leu Asp Ala Ser Val Pro Leu Lys Asp Pro Ile
                85                  90                  95

Lys Ile His Glu Ser Met Arg Tyr Ser Leu Leu Ala Gly Gly Lys Arg
                100                 105                 110

Ile Arg Pro Met Met Cys Ile Ala Ala Cys Glu Ile Val Gly Gly Asn
            115                 120                 125

Ile Leu Asn Ala Met Pro Ala Ala Cys Ala Val Glu Met Ile His Thr
        130                 135                 140

Met Ser Leu Val His Asp Asp Leu Pro Cys Met Asp Asn Asp Asp Phe
145                 150                 155                 160

Arg Arg Gly Lys Pro Ile Ser His Lys Val Tyr Gly Glu Glu Met Ala
                165                 170                 175

Val Leu Thr Gly Asp Ala Leu Leu Ser Leu Ser Phe Glu His Ile Ala
                180                 185                 190

Thr Ala Thr Lys Gly Val Ser Lys Asp Arg Ile Val Arg Ala Ile Gly
            195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300

Lys Asp Leu Leu Thr Asp Lys Thr Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Ala Pro Leu Ile Ala Leu
            340                 345                 350

Ala Asn Tyr Asn Ala Tyr Arg Gln Asn
        355                 360

<210> SEQ ID NO 46
<211> LENGTH: 1086
<212> TYPE: DNA
<213> ORGANISM: Stevia rebaudiana

<400> SEQUENCE: 46

```
atggcgctgg ttaacccgac cgcgctgttc tacggtacct ctatccgtac ccgtccgacc      60
aacctgctga acccgaccca gaaactgcgt ccggtttctt cttcttctct gccgtctttc     120
tcttctgttt ctgcgatcct gaccgaaaaa caccagtcta accgtctga aacaacaac      180
ctgcagaccc acctggaaac cccgttcaac ttcgactctt acatgctgga aaagttaac     240
atggttaacg aagcgctgga cgcgtctgtt ccgctgaaag acccgatcaa atccacgaa     300
tctatgcgtt actctctgct ggcgggtggt aaacgtatcc gtcgatgat gtgcatcgcg     360
gcgtgcgaaa tcgttggtgg taacatcctg aacgcgatgc cggcggcgtg cgcggttgaa     420
atgatccaca ccatgtctct ggttcacgac gacctgccgt gcatggacaa cgacgacttc     480
cgtcgtggta aaccgatctc tcacaaagtt tacggtgaag aaatggcggt tctgaccggt     540
gacgcgctgc tgtctctgtc tttcgaacac atcgcgaccg cgaccaaagg tgtttctaaa     600
gaccgtatcg ttcgtgcgat cggtgaactg gcgcgttctg ttggttctga aggtctggtt     660
gcgggtcagg ttgttgacat cctgtctgaa ggtgcggacg ttggtctgga ccacctggaa     720
tacatccaca tccacaaaac cgcgatgctg ctggaatctt ctgttgttat cggtgcgatc     780
atgggtggtg ttctgaccag cagatcgaa aaactgcgta aattcgcgcg ttctatcggt     840
ctgctgttcc aggttgttga cgacatcctg gacgttacca atctaccga gaactgggt     900
aaaaccgcgg gtaaagacct gctgaccgac aaaaccacct acccgaaact gctgggtatc     960
gaaaaatctc gtgaattcgc ggaaaaactg aacaaagaag cgcaggaaca gctgtctggt    1020
ttcgaccgtc gtaaagcggc gccgctgatc gcgctggcga actacaacgc gtaccgtcag    1080
aactaa                                                                1086
```

<210> SEQ ID NO 47
<211> LENGTH: 525
<212> TYPE: PRT
<213> ORGANISM: Arabidopsis thaliana

<400> SEQUENCE: 47

```
Met Glu Ser Leu Val Val His Thr Val Asn Ala Ile Trp Cys Ile Val
  1               5                  10                  15

Ile Val Gly Ile Phe Ser Val Gly Tyr His Val Tyr Gly Arg Ala Val
                 20                  25                  30

Val Glu Gln Trp Arg Met Arg Arg Ser Leu Lys Leu Gln Gly Val Lys
             35                  40                  45

Gly Pro Pro Pro Ser Ile Phe Asn Gly Asn Val Ser Glu Met Gln Arg
         50                  55                  60

Ile Gln Ser Glu Ala Lys His Cys Ser Gly Asp Asn Ile Ile Ser His
 65                  70                  75                  80

Asp Tyr Ser Ser Ser Leu Phe Pro His Phe Asp His Trp Arg Lys Gln
                 85                  90                  95

Tyr Gly Arg Ile Tyr Thr Tyr Ser Thr Gly Leu Lys Gln His Leu Tyr
                100                 105                 110

Ile Asn His Pro Glu Met Val Lys Glu Leu Ser Gln Thr Asn Thr Leu
            115                 120                 125
```

Asn Leu Gly Arg Ile Thr His Ile Thr Lys Arg Leu Asn Pro Ile Leu
130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190

Met Val Lys Arg Gly Gly Met Gly Cys Asp Ile Arg Val Asp Glu
        195                 200                 205

Asp Leu Lys Asp Val Ser Ala Asp Val Ile Ala Lys Ala Cys Phe Gly
210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Ile Glu Cys Lys Asp Thr His Lys Lys Asp Leu Met Gln Leu
290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
        355                 360                 365

Ser Ser Cys Lys Asn Gly Ile Pro Asp Ala Glu Ser Ile Pro Asn Leu
370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
        435                 440                 445

Glu Arg Phe Ser Glu Gly Ile Ser Lys Ala Cys Lys Tyr Pro Gln Ser
450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525

<210> SEQ ID NO 48
<211> LENGTH: 1578
<212> TYPE: DNA

<213> ORGANISM: Arabidopsis thaliana

<400> SEQUENCE: 48

```
atggaatctc tggttgttca caccgttaac gcgatctggt gcatcgttat cgttggtatc      60
ttctctgttg gttaccacgt ttacggtcgt gcggttgttg aacagtggcg tatgcgtcgt     120
tctctgaaac tgcagggtgt taaaggtccg ccgccgtcta tcttcaacgg taacgtttct     180
gaaatgcagc gtatccagtc tgaagcgaaa cactgctctg gtgacaacat catctctcac     240
gactactctt cttctctgtt cccgcacttc gaccactggc gtaaacagta cggtcgtatc     300
tacacctact ctaccggtct gaaacagcac ctgtacatca accacccgga aatggttaaa     360
gaactgtctc agaccaacac cctgaacctg gtcgtatca cccacatcac caaacgtctg     420
aacccgatcc tgggtaacgg tatcatcacc tctaacggtc cgcactgggc gcaccagcgt     480
cgtatcatcg cgtacgaatt cacccacgac aaaatcaaag gtatggttgg tctgatggtt     540
gaatctgcga tgccgatgct gaacaaatgg gaagaaatgg ttaaacgtgg tggtgaaatg     600
ggttgcgaca tccgtgttga cgaagacctg aaagacgttt ctgcggacgt tatcgcgaaa     660
gcgtgcttcg gttcttcttt ctctaaaggt aaagcgatct tctctatgat ccgtgacctg     720
ctgaccgcga tcaccaaacg ttctgttctg ttccgtttca cggtttcac cgacatggtt     780
ttcggttcta aaaaacacgg tgacgttgac atcgacgcgc tggaaatgga actggaatct     840
tctatctggg aaaccgttaa agaacgtgaa atcgaatgca agacaccca caaaaaagac     900
ctgatgcagc tgatcctgga aggtgcgatg cgttcttgcg acggtaacct gtgggacaaa     960
tctgcgtacc gtcgtttcgt tgttgacaac tgcaaatcta tctacttcgc gggtcacgac    1020
tctaccgcgg tttctgtttc ttggtgcctg atgctgctgg cgctgaaccc gtcttggcag    1080
gttaaaatcc gtgacgaaat cctgtcttct tgcaaaaacg gtatcccgga cgcggaatct    1140
atcccgaacc tgaaaaccgt taccatggtt atccaggaaa ccatgcgtct gtacccgccg    1200
gcgccgatcg ttggtcgtga agcgtctaaa gacatccgtc tgggtgacct ggttgttccg    1260
aaaggtgttt gcatctggac cctgatcccg cgctgcacc gtgacccgga atctggggt    1320
ccggacgcga cgacttcaa accggaacgt ttctctgaag gtatctctaa agcgtgcaaa    1380
taccgcagt cttacatccc gttcggtctg ggtccgcgta cctgcgttgg taaaaacttc    1440
ggtatgatgg aagttaaagt tctggttct ctgatcgttt ctaaattctc tttcaccctg    1500
tctccgacct accagcactc tccgtctcac aaactgctgg ttgaaccgca gcacggtgtt    1560
gttatccgtg ttgttttga                                                 1578
```

<210> SEQ ID NO 49
<211> LENGTH: 532
<212> TYPE: PRT
<213> ORGANISM: Arabidopsis thaliana

<400> SEQUENCE: 49

```
Met Glu Asn Phe Met Val Glu Met Ala Lys Thr Ile Ser Trp Ile Val
  1               5                  10                  15

Val Ile Gly Val Leu Gly Leu Gly Ile Arg Val Tyr Gly Lys Val Met
                 20                  25                  30

Ala Glu Gln Trp Arg Met Arg Arg Lys Leu Thr Met Gln Gly Val Lys
             35                  40                  45

Gly Pro Pro Pro Ser Leu Phe Arg Gly Asn Val Pro Glu Met Gln Lys
         50                  55                  60

Ile Gln Ser Gln Ile Met Ser Asn Ser Lys His Tyr Ser Gly Asp Asn
```

```
            65                   70                  75                  80
Ile Ile Ala His Asp Tyr Thr Ser Ser Leu Phe Pro Tyr Leu Asp His
                85                  90                  95
Trp Arg Lys Gln Tyr Gly Arg Val Tyr Thr Tyr Ser Thr Gly Val Lys
               100                 105                 110
Gln His Leu Tyr Met Asn His Pro Glu Leu Val Lys Glu Leu Asn Gln
               115                 120                 125
Ala Asn Thr Leu Asn Leu Gly Lys Val Ser Tyr Val Thr Lys Arg Leu
               130                 135                 140
Lys Ser Ile Leu Gly Arg Gly Val Ile Thr Ser Asn Gly Pro His Trp
145                150                 155                 160
Ala His Gln Arg Arg Ile Ile Ala Pro Glu Phe Phe Leu Asp Lys Val
               165                 170                 175
Lys Gly Met Val Gly Leu Val Val Glu Ser Ala Met Pro Met Leu Ser
               180                 185                 190
Lys Trp Glu Glu Met Met Lys Arg Glu Gly Glu Met Val Cys Asp Ile
               195                 200                 205
Ile Val Asp Glu Asp Leu Arg Ala Ala Ser Ala Asp Val Ile Ser Arg
210                215                 220
Ala Cys Phe Gly Ser Ser Phe Ser Lys Gly Lys Glu Ile Phe Ser Lys
225                230                 235                 240
Leu Arg Cys Leu Gln Lys Ala Ile Thr His Asn Asn Ile Leu Phe Ser
               245                 250                 255
Leu Asn Gly Phe Thr Asp Val Val Phe Gly Thr Lys Lys His Gly Asn
               260                 265                 270
Gly Lys Ile Asp Glu Leu Glu Arg His Ile Glu Ser Leu Ile Trp Glu
               275                 280                 285
Thr Val Lys Glu Arg Glu Arg Glu Cys Val Gly Asp His Lys Lys Asp
               290                 295                 300
Leu Met Gln Leu Ile Leu Glu Gly Ala Arg Ser Ser Cys Asp Gly Asn
305                310                 315                 320
Leu Glu Asp Lys Thr Gln Ser Tyr Lys Ser Phe Val Val Asp Asn Cys
               325                 330                 335
Lys Ser Ile Tyr Phe Ala Gly His Glu Thr Ser Ala Val Ala Val Ser
               340                 345                 350
Trp Cys Leu Met Leu Leu Ala Leu Asn Pro Ser Trp Gln Thr Arg Ile
               355                 360                 365
Arg Asp Glu Val Phe Leu His Cys Lys Asn Gly Ile Pro Asp Ala Asp
               370                 375                 380
Ser Ile Ser Asn Leu Lys Thr Val Thr Met Val Ile Gln Glu Thr Leu
385                390                 395                 400
Arg Leu Tyr Pro Pro Ala Ala Phe Val Ser Arg Glu Ala Leu Glu Asp
               405                 410                 415
Thr Lys Leu Gly Asn Leu Val Val Pro Lys Gly Val Cys Ile Trp Thr
               420                 425                 430
Leu Ile Pro Thr Leu His Arg Asp Pro Glu Ile Trp Gly Ala Asp Ala
               435                 440                 445
Asn Glu Phe Asn Pro Glu Arg Phe Ser Glu Gly Val Ser Lys Ala Cys
               450                 455                 460
Lys His Pro Gln Ser Phe Val Pro Gly Leu Gly Thr Arg Leu Cys
465                470                 475                 480
Leu Gly Lys Asn Phe Gly Met Met Glu Leu Lys Val Leu Val Ser Leu
               485                 490                 495
```

```
Ile Val Ser Arg Phe Ser Phe Thr Leu Ser Pro Thr Tyr Gln His Ser
            500                 505                 510

Pro Val Phe Arg Met Leu Val Glu Pro Gln His Gly Val Val Ile Arg
        515                 520                 525

Val Leu Arg Gln
    530

<210> SEQ ID NO 50
<211> LENGTH: 1599
<212> TYPE: DNA
<213> ORGANISM: Arabidopsis thaliana

<400> SEQUENCE: 50
atggaaaact tcatggttga aatggcgaaa accatctctt ggatcgttgt tatcggtgtt      60
ctgggtctgg gtatccgtgt ttacggtaaa gttatggcgg aacagtggcg tatgcgtcgt     120
aaactgacca tgcagggtgt taaaggtccg ccgccgtctc tgttccgtgg taacgttccg     180
gaaatgcaga aaatccagtc tcagatcatg tctaactcta acactactc tggtgacaac     240 atcatcgcgc acgactacac ctcttctctg ttcccgtacc tggaccactg gcgtaaacag     300
tacggtcgtg tttacaccta ctctaccggt gttaaacagc acctgtacat gaaccacccg     360
gaactggtta agaactgaa ccaggcgaac accctgaacc tgggtaaagt ttcttacgtt     420
accaaacgtc tgaaatctat cctgggtcgt ggtgttatca cctctaacgg tccgcactgg     480
gcgcaccagc gtcgtatcat cgcgccggaa ttcttcctgg acaaagttaa aggtatggtt     540
ggtctggttt tgaatctgc gatgccgatg ctgtctaaat gggaagaaat gatgaaacgt     600
gaaggtgaaa tggtttgcga catcatcgtt gacgaagacc tgcgtgcggc gtctgcggac     660
gttatctctc gtgcgtgctt cggttcttct ttctctaaag gtaaagaaat cttctctaaa     720
ctgcgttgcc tgcagaaagc gatcacccac aacaacatcc tgttctctct gaacggtttc     780
accgacgttg ttttcggtac caaaaaacac ggtaacggta aaatcgacga actggaacgt     840
cacatcgaat ctctgatctg ggaaaccgtt aaagaacgtg aacgtgaatg cgttggtgac     900
cacaaaaaag acctgatgca gctgatcctg gaaggtgcgc gttcttcttg cgacggtaac     960
ctggaagaca aaacccagtc ttacaaatct ttcgttgttg acaactgcaa atctatctac    1020
ttcgcgggtc acgaaacctc tgcggttgcg gtttcttggt gcctgatgct gctggcgctg    1080
aacccgtctt ggcagacccg tatccgtgac gaagttttcc tgcactgcaa aaacggtatc    1140
ccggacgcgg actctatctc taacctgaaa accgttacca tggttatcca ggaaaccctg    1200
cgtctgtacc cgccggcggc gttcgtttct cgtgaagcgc tggaagacac caaactgggt    1260
aacctggttg ttccgaaagg tgtttgcatc tggaccctga tcccgaccct gcaccgtgac    1320
ccggaaatct ggggtgcgga cgcgaacgaa ttcaacccgg aacgtttctc tgaaggtgtt    1380
tctaaagcgt gcaaacaccc gcagtctttc gttccgttcg gtctgggtac ccgtctgtgc    1440
ctgggtaaaa acttcggtat gatggaactg aaagttctgg tttctctgat cgtttctcgt    1500
ttctctttca ccctgtctcc gacctaccag cactctccgg ttttccgtat gctggttgaa    1560
ccgcagcacg tgttgttat ccgtgttctg cgtcagtaa                             1599

<210> SEQ ID NO 51
<211> LENGTH: 459
<212> TYPE: PRT
<213> ORGANISM: Ipomoea batatas

<400> SEQUENCE: 51
```

```
Met Gly Ser Gln Ala Thr Thr His His Met Ala Met Tyr Pro Trp Phe
1               5                   10                  15
Gly Val Gly His Leu Thr Ala Phe Phe Arg Leu Ala Asn Lys Leu Ala
            20                  25                  30
Ser Lys Gly His Arg Ile Ser Phe Leu Ile Pro Lys Asn Thr Gln Ser
        35                  40                  45
Lys Leu Ala Ser Phe Asn Leu His Pro His Leu Val Ser Phe Val Pro
    50                  55                  60
Ile Thr Val Pro Ser Ile Pro Gly Leu Pro Pro Gly Ala Glu Thr Thr
65                  70                  75                  80
Ser Asp Val Pro Phe Ser Ser Thr His Leu Leu Met Glu Ala Met Asp
                85                  90                  95
Lys Thr Gln Thr Asp Ile Glu Ile Ile Leu Lys Asn Leu Glu Val Asp
                100                 105                 110
Val Val Phe Phe Asp Phe Thr His Trp Leu Pro Gly Leu Ala Arg Lys
            115                 120                 125
Ile Gly Ile Lys Ser Val Phe Tyr Ser Thr Ile Ser Pro Leu Met His
        130                 135                 140
Gly Phe Ala Leu Ser Pro Glu Arg Arg Val Ala Gly Lys Gln Leu Thr
145                 150                 155                 160
Glu Ala Asp Met Met Lys Ala Pro Ala Ser Phe Pro Asp Pro Ser Ile
                165                 170                 175
Lys Leu His Ala His Glu Ala Arg Gly Phe Thr Ala Arg Thr Val Met
                180                 185                 190
Lys Phe Gly Gly Asp Ile Thr Phe Phe Asp Arg Ile Phe Thr Ala Val
            195                 200                 205
Ser Glu Ser Asp Gly Leu Ala Tyr Ser Thr Cys Arg Glu Ile Glu Gly
        210                 215                 220
Gln Phe Cys Asp Tyr Ile Glu Thr Gln Phe Lys Lys Pro Val Leu Leu
225                 230                 235                 240
Ala Gly Pro Ala Leu Pro Val Pro Ser Lys Ser Thr Met Glu Gln Lys
                245                 250                 255
Trp Ser Asp Trp Leu Gly Lys Phe Lys Glu Gly Ser Val Ile Tyr Cys
                260                 265                 270
Ala Phe Gly Ser Glu Cys Thr Leu Arg Lys Glu Gln Phe Gln Glu Leu
            275                 280                 285
Leu Trp Gly Leu Glu Leu Thr Gly Met Pro Phe Phe Ala Ala Leu Lys
        290                 295                 300
Ala Pro Phe Gly Thr Asp Ser Ile Glu Ala Ala Ile Pro Glu Glu Leu
305                 310                 315                 320
Arg Glu Lys Ile His Gly Lys Gly Ile Val His Gly Gly Trp Val Gln
                325                 330                 335
Gln Gln Leu Phe Leu Gln His Pro Ser Val Gly Cys Phe Val Ser His
                340                 345                 350
Cys Gly Trp Ala Ser Leu Ser Glu Ala Leu Val Asn Asp Cys Gln Ile
            355                 360                 365
Val Leu Leu Pro Gln Val Gly Asp Gln Ile Ile Asn Ala Arg Ile Met
        370                 375                 380
Ser Val Ser Leu Lys Val Gly Val Glu Val Glu Lys Gly Glu Glu Asp
385                 390                 395                 400
Gly Val Phe Ser Arg Glu Ser Val Cys Lys Ala Val Lys Ala Val Met
                405                 410                 415
```

-continued

Asp Glu Lys Ser Glu Ile Gly Arg Glu Val Arg Gly Asn His Asp Lys
        420                 425                 430

Leu Arg Gly Phe Leu Leu Asn Ala Asp Leu Asp Ser Lys Tyr Met Asp
    435                 440                 445

Ser Phe Asn Gln Lys Leu Gln Asp Leu Leu Gly
    450                 455

<210> SEQ ID NO 52
<211> LENGTH: 1377
<212> TYPE: DNA
<213> ORGANISM: Ipomoea batatas

<400> SEQUENCE: 52

```
atgggttctc aggcgaccac ccaccacatg gcgatgtacc cgtggttcgg tgttggtcac      60
ctgaccgcgt tcttccgtct ggcgaacaaa ctggcgtcta aggtcaccg tatctctttc     120
ctgatcccga aaacaccca gtctaaactg gcgtctttca acctgcaccc gcacctggtt     180
tctttcgttc cgatcaccgt tccgtctatc ccgggtctgc cgccgggtgc ggaaaccacc     240
tctgacgttc cgttctcttc tacccacctg ctgatggaag cgatggacaa acccagacc     300
gacatcgaaa tcatcctgaa aaacctggaa gttgacgttg ttttcttcga cttcacccac     360
tggctgccgg gtctggcgcg taaaatcggt atcaaatctg ttttctactc taccatctct     420
ccgctgatgc acggtttcgc gctgtctccg aacgtcgtg ttgcgggtaa acagctgacc     480
gaagcggaca tgatgaaagc gccggcgtct ttcccggacc cgtctatcaa actgcacgcg     540
cacgaagcgc gtggtttcac cgcgcgtacc gttatgaaat cggtggtga catcaccttc     600
ttcgaccgta tcttcaccgc ggtttctgaa tctgacggtc tggcgtactc tacctgccgt     660
gaaatcgaag tcagttctg cgactacatc gaaacccagt tcaaaaaacc ggttctgctg     720
gcgggtccgg cgctgccggt tccgtctaaa tctaccatgg aacagaaatg gtctgactgg     780
ctgggtaaat tcaaagaagg ttctgttatc tactgcgcgt tcggttctga atgcaccctg     840
cgtaaagaac agttccagga actgctgtgg ggtctggaac tgaccggtat gccgttcttc     900
gcggcgctga agcgccgttt cggtaccgac tctatcgaag cggcgatcc ggaagaactg     960
cgtgaaaaaa tccacggtaa aggtatcgtt cacggtggtt gggttcagca gcagctgttc    1020
ctgcagcacc cgtctgttgg ttgcttcgtt tctcactgcg gttgggcgtc tctgtctgaa    1080
gcgctggtta acgactgcca gatcgttctg ctgccgcagg ttggtgacca gatcatcaac    1140
gcgcgtatca tgtctgtttc tctgaaagtt ggtgttgaag ttgaaaaagg tgaagaagac    1200
ggtgtttct ctcgtgaatc tgtttgcaaa gcggttaaag cggttatgga cgaaaaatct    1260
gaaatcggtc gtgaagttcg tggtaaccac gacaaactgc gtggtttcct gctgaacgcg    1320
gacctggact ctaaatacat ggactctttc aaccagaaac tgcaggacct gctgggt      1377
```

<210> SEQ ID NO 53
<211> LENGTH: 39
<212> TYPE: DNA
<213> ORGANISM: Artificial Sequence
<220> FEATURE:
<223> OTHER INFORMATION: dxs-F Primer

<400> SEQUENCE: 53

```
catgccatgg gcatgagttt tgatattgcc aaatacccg                              39
```

<210> SEQ ID NO 54
<211> LENGTH: 30
<212> TYPE: DNA

```
<213> ORGANISM: Artificial Sequence
<220> FEATURE:
<223> OTHER INFORMATION: dxs-R Primer

<400> SEQUENCE: 54
cggaattcac tagtttatgc cagccacctt                                         30

<210> SEQ ID NO 55
<211> LENGTH: 36
<212> TYPE: DNA
<213> ORGANISM: Artificial Sequence
<220> FEATURE:
<223> OTHER INFORMATION: ispD-F Primer

<400> SEQUENCE: 55
catgccatgg gcatggcaac cactcatttg gatgtt                                  36

<210> SEQ ID NO 56
<211> LENGTH: 39
<212> TYPE: DNA
<213> ORGANISM: Artificial Sequence
<220> FEATURE:
<223> OTHER INFORMATION: ispD-R Primer

<400> SEQUENCE: 56
cggaattcac tagtttatgt attctcctga tggatggtt                               39

<210> SEQ ID NO 57
<211> LENGTH: 34
<212> TYPE: DNA
<213> ORGANISM: Artificial Sequence
<220> FEATURE:
<223> OTHER INFORMATION: ispF-F Primer

<400> SEQUENCE: 57
catgccatgg gcatgcgaat tggacacggt tttg                                    34

<210> SEQ ID NO 58
<211> LENGTH: 38
<212> TYPE: DNA
<213> ORGANISM: Artificial Sequence
<220> FEATURE:
<223> OTHER INFORMATION: ispF-R Primer

<400> SEQUENCE: 58
cggaattcac tagttcattt tgttgcctta atgagtag                                38

<210> SEQ ID NO 59
<211> LENGTH: 36
<212> TYPE: DNA
<213> ORGANISM: Artificial Sequence
<220> FEATURE:
<223> OTHER INFORMATION: idi-F Primer

<400> SEQUENCE: 59
catgccatgg gcatgcaaac ggaacacgtc atttta                                  36

<210> SEQ ID NO 60
<211> LENGTH: 31
<212> TYPE: DNA
<213> ORGANISM: Artificial Sequence
<220> FEATURE:
<223> OTHER INFORMATION: idi-R - Primer

<400> SEQUENCE: 60
cggaattctt atttaagctg ggtaaatgca g                                       31
```

-continued

```
<210> SEQ ID NO 61
<211> LENGTH: 7
<212> TYPE: PRT
<213> ORGANISM: Artificial Sequence
<220> FEATURE:
<223> OTHER INFORMATION: Active fragment of the bifunctional CPS/KS
      enzyme having CDPS and KS activities
<220> FEATURE:
<221> NAME/KEY: misc_feature
<222> LOCATION: (6)..(6)
<223> OTHER INFORMATION: Xaa can be any naturally occurring amino acid

<400> SEQUENCE: 61

Tyr Asp Thr Ala Trp Xaa Ala
1               5

<210> SEQ ID NO 62
<211> LENGTH: 4
<212> TYPE: PRT
<213> ORGANISM: Artificial Sequence
<220> FEATURE:
<223> OTHER INFORMATION: Active fragment of the bifunctional CPS/KS
      enzyme having CDPS and KS activities
<220> FEATURE:
<221> NAME/KEY: misc_feature
<222> LOCATION: (2)..(2)
<223> OTHER INFORMATION: Xaa can be any naturally occurring amino acid

<400> SEQUENCE: 62

Asp Xaa Asp Asp
1

<210> SEQ ID NO 63
<211> LENGTH: 5
<212> TYPE: PRT
<213> ORGANISM: Artificial Sequence
<220> FEATURE:
<223> OTHER INFORMATION: Active fragment of the bifunctional CPS/KS
      enzyme having CDPS and KS activities
<220> FEATURE:
<221> NAME/KEY: misc_feature
<222> LOCATION: (3)..(4)
<223> OTHER INFORMATION: Xaa can be any naturally occurring amino acid

<400> SEQUENCE: 63

Asp Asp Xaa Xaa Asp
1               5

<210> SEQ ID NO 64
<211> LENGTH: 7
<212> TYPE: PRT
<213> ORGANISM: Artificial Sequence
<220> FEATURE:
<223> OTHER INFORMATION: Active fragment of the bifunctional CPS/KS
      enzyme having CDPS and KS activities
<220> FEATURE:
<221> NAME/KEY: misc_feature
<222> LOCATION: (6)..(6)
<223> OTHER INFORMATION: Xaa can be any naturally occurring amino acid

<400> SEQUENCE: 64

Tyr Asp Thr Ala Trp Xaa Ala
1               5

<210> SEQ ID NO 65
<211> LENGTH: 4
<212> TYPE: PRT
<213> ORGANISM: Artificial Sequence
<220> FEATURE:
<223> OTHER INFORMATION: Active fragment of the bifunctional CPS/KS
      enzyme having CDPS and KS activities
```

```
<220> FEATURE:
<221> NAME/KEY: misc_feature
<222> LOCATION: (2)..(2)
<223> OTHER INFORMATION: Xaa can be any naturally occurring amino acid

<400> SEQUENCE: 65

Asp Xaa Asp Asp
1

<210> SEQ ID NO 66
<211> LENGTH: 5
<212> TYPE: PRT
<213> ORGANISM: Artificial Sequence
<220> FEATURE:
<223> OTHER INFORMATION: Active fragment of the bifunctional CPS/KS
      enzyme having CDPS and KS activities
<220> FEATURE:
<221> NAME/KEY: misc_feature
<222> LOCATION: (3)..(4)
<223> OTHER INFORMATION: Xaa can be any naturally occurring amino acid

<400> SEQUENCE: 66

Asp Glu Xaa Xaa Glu
1               5

<210> SEQ ID NO 67
<211> LENGTH: 5
<212> TYPE: PRT
<213> ORGANISM: Artificial Sequence
<220> FEATURE:
<223> OTHER INFORMATION: Active fragment of the UGTB1
      glycosyltransferase

<400> SEQUENCE: 67

Gly His Val Gly Pro
1               5

<210> SEQ ID NO 68
<211> LENGTH: 6
<212> TYPE: PRT
<213> ORGANISM: Artificial Sequence
<220> FEATURE:
<223> OTHER INFORMATION: Active fragment of the UGTB1
      glycosyltransferase

<400> SEQUENCE: 68

Asn Gly Gly Tyr Gly Gly
1               5
```